US009186418B2

(12) United States Patent
Cohen

(10) Patent No.: US 9,186,418 B2
(45) Date of Patent: Nov. 17, 2015

(54) METHOD OF IDENTIFYING TUMOR ASSOCIATED ANTIGENS

(75) Inventor: Edward P. Cohen, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 130 days.

(21) Appl. No.: 13/324,856

(22) Filed: Dec. 13, 2011

(65) Prior Publication Data

US 2012/0164180 A1 Jun. 28, 2012

Related U.S. Application Data

(63) Continuation of application No. 11/909,251, filed as application No. PCT/US2006/011575 on Mar. 28, 2006, now abandoned.

(60) Provisional application No. 60/697,334, filed on Jul. 7, 2005, provisional application No. 60/733,663, filed on Nov. 4, 2005.

(51) Int. Cl.
| C07K 14/47 | (2006.01) |
| A61K 48/00 | (2006.01) |
| A61K 38/19 | (2006.01) |
| A61K 38/20 | (2006.01) |
| A61K 39/00 | (2006.01) |
| A61K 39/39 | (2006.01) |
| A61K 35/12 | (2015.01) |

(52) U.S. Cl.
CPC .............. *A61K 48/00* (2013.01); *A61K 38/193* (2013.01); *A61K 38/204* (2013.01); *A61K 38/208* (2013.01); *A61K 38/2013* (2013.01); *A61K 38/2026* (2013.01); *A61K 39/0011* (2013.01); *A61K 39/39* (2013.01); *A61K 35/12* (2013.01); *A61K 2039/5154* (2013.01); *A61K 2039/5156* (2013.01); *A61K 2039/53* (2013.01); *A61K 2039/55522* (2013.01); *A61K 2039/55527* (2013.01)

(58) Field of Classification Search
CPC .............. C07K 14/4748; C07K 16/32; C07K 2317/34; C07K 16/18; C07K 14/47; C07K 16/30; A61K 39/0011; A61K 39/00; A61K 2039/5154; A61K 2039/5156; A61K 2039/5158; C12Q 1/6886; C12Q 2600/136; G01N 33/574
USPC ......................................................... 435/325
See application file for complete search history.

(56) References Cited

U.S. PATENT DOCUMENTS

| 5,674,486 A | 10/1997 | Sobol et al. |
| 5,750,102 A | 5/1998 | Eisenbach et al. |
| 5,759,535 A | 6/1998 | Cohen |
| 6,022,538 A | 2/2000 | Santoli et al. |
| 6,187,307 B1 * | 2/2001 | Cohen .................. 424/93.21 |
| 6,228,357 B1 | 5/2001 | Maudsley |
| 6,277,368 B1 | 8/2001 | Hiserodt et al. |
| 6,805,869 B2 | 10/2004 | Guo |
| 7,060,802 B1 | 6/2006 | Trakht et al. |
| 7,402,306 B1 | 7/2008 | Cohen |
| 7,670,611 B2 | 3/2010 | Cohen |
| 2002/0058041 A1 | 5/2002 | Belldegrun et al. |
| 2002/0085997 A1 | 7/2002 | Schmidt et al. |

FOREIGN PATENT DOCUMENTS

| EP | 0569678 | 11/1993 |
| WO | 93/07906 | 4/1993 |
| WO | 98/11202 | 3/1998 |
| WO | 98/14205 | 4/1998 |

OTHER PUBLICATIONS

Lewis et al, Int Rev Immunol, 2003, 22:81-112.*
Conway et al, Cancer Res, 2000, 60:6236-6242.*
Wilson et al, American Journal of Pathology, 2002, 161:1171-1185.*
Makela et al, Environmental Health Perspectives, 1994, 102:572-578.*
Hodgson, "Patent Update. Biologicals & Immunologicals. Advances in vector systems for gene therapy," Exp. Opin. Ther. Patents 5(5):459-468 (1995).
Orkin et al., "Report and Recommendations of the Panel to Assess the NIH Investment in Research on Gene Therapy," NIH, pp. 1-37, Dec. 7, 1995.
Marshall, "Gene Therapy's Growing Pains," Science, 269:1050-1055 (1995).
Miller et al., "Targeted vectors for gene therapy," FASEB J., 9:190-199 (1995).
Culver et al., "Gene therapy for cancer," TIG, 19(5):174-179 (1994).
Blankenstein T., et al., "Tumor Suppression after Tumor Cell-targeted Tumor Necrosis Factor alpha Gene Transfer," J. Exp. Med., 173:1047-1052 (1991).
Colombu, M. et al., "Granulocyte Coony-stimulating Factor Gene Transfer Suppresses Tumorigenicity of a Murine Adenocarcinoma in Vivo," J. Exp. Med., 173:889-897 (1991).
Dranoff, G. et al., "Vaccination with irradiated tumor cells engineered to secret murine granulocyte-macrophage colony-stimulating factor stimulates potent, specific, and long-lasting anti-tumor immunity," Proc. Natl. Acad. Sci. USA, 90:3539-3543 (1993).
Fearon, E.R. et al., "Interleukin-2 Productions by Tumor Cells Bypasses T Helper Function in the Generation of an Anti-tumor Response," Cell, 60:397-403 (1990).
Ferrantini M., alpha 1-Interferon Gene Transfer into Metastatic Friend Leukemia Cells Abrogated Tumorigenicity in Immunocompetent Mice; Antitumor Therapy by Means of Interferon-producing Cells, Cancer Res., 53:1107-1112 (1993).

(Continued)

*Primary Examiner* — Michael Wilson
(74) *Attorney, Agent, or Firm* — McDonnell Boehnen Hulbert & Berghoff LLP

(57) ABSTRACT

Compositions and methods of producing improved cancer vaccines are described. In addition, methods of identifying tumor associated antigens are also described.

11 Claims, 26 Drawing Sheets

(56) References Cited

OTHER PUBLICATIONS

Golumbeck, P., "Treatment of Established Renal Cancer by Tumor Cells Engineered to Secrete Interleukin-4," Science, 254:713-716 (1991).

Karp S.E., et al., "Cytokin Secretion by Genetically Modified Nonimmunogenic Murine Fibrosarcoma," J. Immunol., 150:896-908 (1993).

Kim et al., "Immunity to melanoma in mice immunized with transfected allogeneic mouse fibroblasts expressing melanoma-associated antigens," Cancer Immunol. Immunother., 34:163-168 (1991).

Kim et al., "Interleukin-2-secreting-Mouse Fibroblasts Transfected with Genomic DNA from Murine Melanoma Cells Prolong the Survival of Mice with Melanoma," Cancer Research, 54:2531-2535 (1994).

Kim T., et al., "Immunity to B16 Melanoma in Mice Immunized with IL-2 Secreting Allogeneic Mouse Fibroblasts Expressing Melanoma-Associated Antigens," Int. J. Cancer., vol. 51, pp. 283-289 (1992).

Schmidt W. et al., "Transloading of Tumor Cells with Foreign Major Histocompatibility Complex Class I Peptide Ligand: A Novel General Strategy for the Generation of Potent Cancer Vaccines," Proc. Natl. Acad. Sci. USA, vol. 93, pp. 9759-9763 (1996).

Shawler D.L. et al., "Gene Therapy Approaches to Enhance Antitumor Immunity," Advances in Pharmacology, 40:309-337 (1997).

Boon T. et al., "Identification of Tumour Rejection Antigens Recognized by T-Lymphocytes," Cancer Surveys 13:23-27 (1992).

Boon T., "Tumor Antigens Recognized by Cytolytic T Lymphocytes: Present Perspectives for Specific Immunotherapy," Int. J. Cancer, 54:177-180 (1993).

Boon T., "Toward a Genetic Analysis of Tumor Rejection Antigens," Advances in Cancer Research, 58:177-209 (1992).

Vieweg J. et al., "Considerations for the Use of Cytokine-Secreting Tumor Cell Preparations for Cancer Treatment," Cancer Investigation, 13(2): 193-201 (1995).

Hui K.M. et al., "Tumor Rejection Mediated by Transfection with Allogeneic Class I Histocompatibility Gene," The Journal of immunology, 143(11):3835-3843 (1989).

Ostrand-Rosenberg S. et al., "Tumor-Specific Immunity Can Be Enhanced by Transfection of Tumor Cells with Syngeneic MHC-Class-II Genes or Allogeneic MHC-Class-I Genes," Int. J. Cancer, 6 (Supp.):61-68 (1991).

Roth J.A. et al., "Gene Therapy for Cancer: What Have We Done and Where Are We Going?" Journal of the National Cancer Institute, 89(1):21-39 (1997).

Kim T.S. et al., "MHC Antigen Expression by Melanomas Recovered From Mice Treated with allogeneic Mouse Fibroblasts Genetically Modified for Interleukin-2 Secretion and the Expression of Melanoma-associated Antigens," Cancer Immunol. Immunother., 38:185-193 (1994).

Cohen E.P. et al., "Neoplastic Cells That Express Low Levels of MHC Class I Determinants Escape Host Immunity," Seminars in Cancer Biology, 5:419-428 (1994).

Itaya T. et al., "Xenogenization of a Mouse Lung Carcinoma (3LL) by Transfection With An Allogeneic Class I Major Histocompatibility Complex Gene (H-2-Ld)," Cancer Research, 47:3136-3140 (1987).

Lichtor T. et al., "Prolonged Survival of Mice with Glioma Injected Intracerebrally With Double Cytokine-secreting Cells," J. Neurosurg., 83:1038-1044 (1995).

van der Bruggen P. et al., "A Gene Encoding an Antigen Recognized by Cytolytic T Lymphocytes on a Human Melanoma," Science 254:1643-1647 (1991).

Toffaletti D.L. et al., "Augmentation of Syngeneic Tumor-specific Immunity by Semiallogeneic Cells Hydbrids," The Journal of Immunology, 130(6):2982-2986 (1983).

Colnaghi Mi., "Histocompatibility Antigens Acting as Helper Determinants for Tumor-associated Antigens of Murine Lymphosarcoma," Eur. J. Immunol., 5:241-245 (1975).

Xu W. et al., "Co-expression fo Immunogenic Determinants by the Same Cellular Immunogen is Required for the Optimum Immunotherapeutic Benefit in Mice with Melanoma," Cancer Immunol. Immunother., 45:217-224 (1998).

Wang D.R. et al., "Leukemia x Fibroblast Hybrid Cells Prolong the Lives of Leukemic Mice," Eur. J. Cancer Clin. Oncol., 21(5):637-645 (1985).

Liang et al., "Resistance to Murine Leukemia in Mice Rejecting Syngeneic Somatic Hybrid Cells," The Journal of Immunology, 116(3):623-626 (1976).

Liang et al., "Activation of Specific Cellular Immunity Toward Murine Leukemia in Mice Rejecting Syngeneic Somatic Hybrid Cells," The Journal of Immunology, 119(3):1054-1060 (1977).

Kim B.S. et al., "Tumor-specific Immunity Induced by Somatic Hybrids," The Journal of Immunology, 123(2):733-738 (1979).

Garber et al., "Persistence of the Immunoprotective Effects of Leukemia x Fibroblast Hybrid Cells Toward Leukemia in Histocompatible Mice," Leukemia Research 8(2):255-266 (1984).

Slomski R. et al., "Surface Antigens of Immunoprotective Leukaemia x Fibroblast Hybrid Cells Which Have Lost Malignant Properties in Histocompatible Mice Differ From the Malignant Parental Cells," Immunology, 52:281-290 (1984.

Liang W. et al., "Resistance to Murine Leukemia in Mice Receiving Simultaneous Injections of Syngeneic Hybrid and Parental Neoplastic Cells," The Journal of immunology, 118(3):903-908 (1977).

Jami et al., "Tumor-associated Transplantation Antigens in Immune Rejection of Mouse Malignant Cell Hybrids," Proc. Nat. Acad. Sci. USA 72(6):2130-2134 (1975).

Jami J. et al., "Nonmalignancy of Hybrids Derived from Two House Malignant Cells. I. Hybrids Between L1210 Leukemia Cells and Malignant L. Cells," Journal of the National Cancer Institute, 51(5):1647-1653 (1973).

Karp S.E. et al., "Cytokine Secretion by Genetically Modified Nonimmunogeneic Murine Fibrosarcoma Tumor Inhibition oby IL-2 but Not Tumor Necrosis Factor," The Journal of Immunology, 150(3):896-908 (1993).

Kim T.S. et al., "Independent Cell Types Are Involved in the Induction of Antimelanoma Responses in C57BL/6 Mice Immunized with INterleukin-2-secreteing Allogeneic Mouse Fibroblasts Expressing Melanoma-associated Antigens," Journal of Immunotherapy, 14:298-304 (1993).

Kim T.S. et al., "Immunization with Interleukin-2-secreting Allogeneic Mouse Fibroblasts Expressing Melanoma-associated Antigens Prolongs the Survival of Mice With Melanoma," Int. J. Cancer, 55:865-872 (1993).

Pardoll D.M., "Cancer Vaccines," Immunology Today, 14(6):310-316 (1993).

Pardoll D., "New Strategies for Active Immunotherapy with Genetically Engineered Tumor Cells," Current Opinion in Immunology, 4:619-623 (1992).

Porgador A. et al., "Antimetastatic Vaccination of Tumor-bearing Mice with Two Types of IFN-λ Gene-inserted Tumor Cells," The Journal of Immunology, 150(4):1458-1470 (1993).

Porgador A. et al., "Antimetastatic Vaccination of Tumor-bearing Mice with IL-2-Gene-inserted Tumor Cells," Int. J. Cancer, 53:471-477 (1993).

Porgador A. et al., "Interleukin 6 Gene Transfection into Lewis Lung Carcinoma Tumor Cells Suppresses the Malignant Phenotype and Confers Immunotherapeutic Competence Against Parental Metastatic Cells," Cancer Research, 52:3679-3686 (1992).

Rosenberg S.A., "The Immunotherapy and Gene Therapy of Cancer," Journal of Clinical Oncology, 10(2):180-189 (1992).

Russell S.J. et al., "Decreased Tumorigenicity of a Transplantable Rat Sarcoma Following Transfer and Expression of an IL-2 cDNA," Int. J. Cancer, 47:244-251 (1991).

Weber et al., "Modulation of Murine Tumor Major Histocompatibility Antigens by Cytokines in Vivo and in Vitro," Cancer Research, 48:5818-5824 (1988).

Yamada et al., "Retroviral Expression of the Human IL-2 Gene in a Murine T-Cell Line Results in Cell Growth Autonomy and Tumorigenicity," The EMBO Journal, 6(9):2705-2709 (1987).

(56) References Cited

OTHER PUBLICATIONS

Zoller M. et al., "Interferon-gamma Treatment of B16 Melanoma Cells: Opposing Effects for Non-adaptive and Adaptive Immune Defense and its Reflection by Metastatic Spread," Int. J. Cancer, 41:256-266 (1988).
Kasai M. et al., "A Glycolipid on the Surface of Mouse Natural Killer Cells," Eur. J. Immunol., 10:175-180 (1980).
Oettgen H.F. et al., "Serologic Analysis of Human Cancer," Immunol. Allergy Clin. North. Am., 10(4):607-637 (1990).
Sarmiento M. et al., "IgG or IgM Monoclonal Antibodies Reactive With Different Determinants on the Molecular Complex Bearing LYT 2 Antigen Block T Cell-mediated Cytolysis in the Absence of Complement," J. Immunol., 125 (6):2665-2672 (1985).
Sugden B. et al., "A Vector That Replicates as a Plasmid and Can Be Efficiently Selected in B-Lymphoblasts Transformed by Epstein-Barr Virus," Mol. Cell. Biol. 5(2):410-413 (1985).
Traversari C. et al., "A Nonapeptide Encoded by Human Gene MAGE-1 Is Recognized on HLA-A1 by Cytolytic T Lymphocytes Directed Against Tumor Antigen MZ2-E," J. Exp. Med., 176:1453-1457 (1992).
Vile R.G. et al., "In Vitro and in Vivo Targeting of Gene Expression to Melanoma Cells," Cancer Res., 52:962-967 (1993).
Wigler et al., "Biochemical Transfer of Single-copy Eucaryotic Genes Using Total Cellular DNA as Donor," Cell, 14:725-731 (1978).
Young H.E. et al., "Mesenchymal Stem Cells Reside Within the Connective Tissues of Many Organs," Dev. Dynamics, 202:137-144 (1995).
Newton D.A. et al. "Melanoma Cell Hybrids as Cancer Vaccines," Proceedings of the Annual Meeting of the American Association for Cancer Research, 38:398 (1997).
Toffaletti et al., "Augmentation of Syngeneic Tumor-specific Immunity by Semiallogeneic Cell Hybrids," Journal of Immunology, 130(6):2982-2986 (1983).
Payelle et al., "Adoptive Transfer of Immunity Induced by Semi-allogeneic Hybrid Cells Against Murine Firbrosarcoma," Int. J. Cancer, 27:783-788 (1981).
Mandelboim et al., "Expression of two H-2K genes, syngeneic and allogeneic, as a strategy for potentiating immune recognition of tumor cells," Gene Therapy,2 :757-765 (1995).
Sun T. et al., "Interleukin-2-secreting mouse fibroblasts transfected with genomic DNA from murine meoplasms induce tumor-specific immune responses that prolong the lives of tumor-bearing mice," Cancer Gene Therapy, 2(3):183-190 (1995).
Weiner L.M., Seminars Oncology, "An Overview of Monoclonal Antibody Therapy of Cancer," 26(4) Supp. 12, 41-50 (1999).
Bellone et al., "Cancer immunotherapy: synthetic and natural peptides in the balance," Immunology Today, 20(10):457-462 (1999).
Gura, "Systems for Identifying New Drugs are Often Faulty," Science, 278:1041-1042 (1997).
Lappin MB et al., "The Th1-Th2 classification of cellular immune responses: concepts, current thinking and applications in haematological malignancy," Blood Reviews, 14:228-239 (2000).
Roitt et al., Immunology 4th Ed., 11.7-11.14 (1998).
Evans et al., "Vaccine therapy for cancer—fact or fiction?" Quart. J. Med., 92:299-307 (1999).
Whiteside et al., "Human tumor-derived genomic DNA transduced into a recipient cell induces tumor-specific immune responses ex vivo", Proc Natl Acad Sci U.S.A., 99(14): 9415-20 (2002).

\* cited by examiner

Analysis by limiting dilution of spleen cells from mice immunized with sub-pools of transfected cells Immunity to breast cancer in mice immunized with immuno $^{high}$ and immuno $^{low}$ sub-pools of transfected cells Staining of immuno $^{high}$ and immuno $^{low}$ cells for Muc-1

Comparison of gene expression in immuno high and immuno low pools of transfected cells Number of genes over expressed in
immuno $^{high}$ and immuno $^{low}$ pools Frequency of antigen-positive cells in
immuno ʰⁱᵍʰ sub pools of transfected cells

SEQUENCE LISTING

<160> NUMBER OF SEQ ID NOS: 1

<210> SEQ ID NO 1
<211> LENGTH: 2235
<212> TYPE: DNA
<213> ORGANISM: Mus musculus

<400> SEQUENCE: 1

```
ccacctcaca cacggagcgc cagccttgag tttgttttct agccccttcc cgcctgttca        60
ccaccaccat gaccccgggc attcgggctc ctttcttcct gctgctactt ctagcaagtc       120
taaaaggttt tcttgccctt ccaagtgagg aaaacagtgt cacctcatct caggacacca       180
gcagttcctt agcatcgact accactccag tccacagcag caactcagac ccagccacca       240
gacctccagg ggactccacc agctctccag tccagagtag cacctcttct ccagccacca       300
gagctcctga agactctacc agtactgcag tcctcagtgg cacctcctcc ccagccacca       360
cagctccagt gaactccgcc agctctccag tagcccatgg tgacacctct tccccagcca       420
ctagcctttc aaaagactcc aacagctctc cagtagtcca cagtggcacc tcttcagctc       480
cggccaccac agctccagtg gattccacca gctctccagt agtccacggt ggtacctcgt       540
ccccagccac cagccctcca ggggactcca ccagctctcc agaccatagt agcacctctt       600
ctccagccac cagagctccc gaagactcta ccagtactgc agtcctcagt ggcacctcct       660
ccccagccac cacagctcca gtggactcca ccagctctcc agtagcccat gatgacacct       720
cttccccagc cactagcctt tcagaagact ccgccagctc tccagtagcc acggtggca       780
cctcttctcc agccaccagc cctctaaggg actccaccag ttctccagtc cacagtagtg       840
cctccatcca aaacatcaag actacatcag acttagctag cactccagac cacaatggca       900
cctcagtcac aactaccagc tctgcactgg gctcagccac cagtccagac cacagtggta       960
cctcaactac aactaacagc tctgaatcag tcttggccac cactccagtt tacagtagca      1020
tgccattctc tactaccaaa gtgacgtcag gctcagctat cattccagac cacaatggct      1080
cctcggtgct acctaccagt tctgtgttgg gctcagctac cagtcagtc tataatacct      1140
ctgcaatagc tacaactcca gtcagcaatg gcactcagcc ttcagtgcca agtcaatacc      1200
ctgtttctcc taccatggcc accacctcca gccacagcac tattgccagc agctcttact      1260
atagcacagt accatttct accttctcca gtaacagttc accccagttg tctgttgggg       1320
tctccttctt cttcttgtct ttttacattc aaaaccaccc atttaattct tctctggaag      1380
accccagctc caactactac caagaactga agaggaacat ttctggattg tttctgcaga      1440
tttttaacgg agattttctg gggatctcta gcatcaagtt caggtcaggc tccgtggtgg      1500
tagaatcgac tgtggttttc cgggagggta cttttagtgc ctctgacgtg aagtcacagc      1560
ttatacagca taagaaggag gcagatgact ataatctgac tatttcagaa gtcaaagtga      1620
atgagatgca gttccctccc tctgcccagt cccggccggg ggtaccaggc tggggcattg      1680
ccctgctggt gctggtctgt attttggttg ctttggctat cgtctattc cttgccctgg      1740
cagtgtgcca gtgccgccga agagctatg ggcagctgga catctttcca acccaggaca      1800
cctaccatcc tatgagtgaa taccctacct accacactca cggacgctac gtgccccctg      1860
gcagtaccaa gcgtagcccc tatgaggagt ttcggcagg taatggcagt agcagtctct      1920
cttataccaa cccagctgtg gtgaccactt ctgccaactt gtaggagcaa gtcacccac       1980
ccacttgggg cagctttggc ggtctgctcc ctcagtggtc actgccagac ccctgcactc      2040
tgatctgggc tggtgagcca ggacttctgg taggctgttc atgcccttg tcaagcgcct       2100
caactacgta agcctggtga agcccagccc tgccctgggg gacactgggg cagttagtgg      2160
tggctctcag aaggactggc ctggaaaact ggagacaggg atgggaaccc aaacatagct      2220
gaataaaaga tggcc                                                       2235
```

US 9,186,418 B2

METHOD OF IDENTIFYING TUMOR ASSOCIATED ANTIGENS

PRIORITY CLAIM

This application is a continuation application of U.S. Ser. No. 11/909,251, filed May 2, 2009, which is a §371 U.S. National Phase Application based on International Application PCT/US06/11575, filed Mar. 28, 2006, which in turn claims priority from US provisional patent applications 60/697,334 filed Jul. 7, 2005; and 60/733,663 filed Nov. 4, 2005; the disclosures of which are incorporated by reference herein in their entirety.

STATEMENT REGARDING FEDERALLY SPONSORED RESEARCH AND DEVELOPMENT

This invention was made with Government support under Grant Number DE13970 awarded by the National Institutes of Health. The Government has certain rights in this invention.

FIELD OF THE INVENTION

The present invention relates to vaccines and methods for treating a disease, such as cancer. More specifically, the present invention relates to immunogenic cells which act to stimulate and induce an immunogenic response to an antigen, such as a tumor associate antigen (TAA).

The present invention also concerns treatment of cancer using a genomic DNA-based vaccine. In addition, the present invention concerns the use of a genomic DNA-based vaccine in combination with a chemotherapeutic agent for the treatment of cancer.

DESCRIPTION OF RELATED ART

The frequency of cancer in humans has increased in the developed world as the population has aged. For some types of cancers and stages of disease at diagnosis, morbidity and mortality rates have not improved significantly in recent years in spite of extensive research. During the progression of cancer, tumor cells become more and more independent of negative regulatory controls as a result of mutated or dysregulated genes. The mutated or overexpressed proteins of cancer cells may result in the cancer cell becoming antigenecally distinct from normal cells. Such proteins are referred to as tumor-associated antigens (TAAs), since they may be recognized as foreign and may be attacked by a patient's immune system (Sibille et al., J. Ex. Med, 172:35-45, 1990). Tumor associated antigens have been identified for a number of tumors, including melanoma, breast adenocarcinoma, prostate adenocarcinoma, esophageal cancer, lymphoma, and many others. Based on such antigenic differences between malignant and non-malignant cells, immunotherapy has been suggested as a reasonable means of treating cancer.

Current immunotherapeutic approaches to cancer treatment include cancer vaccines based on tumor cell lysates, apoptotic tumor-cell bodies or defined antigens. To this point, cancer vaccines have typically been weakly immunogenic. Thus, there is a long-felt need in the art to identify new TAAs of sufficient immunogenicity to serve as part of cancer vaccines.

The potential benefits of immunotherapy as an adjunct to conventional forms of cancer treatment are under active investigation (Yu B, Clin Cancer Res 2003; 9:285-94; Chang S Y, Int J Cancer 2004; 111:86-95; Dsis M L, J Clin Oncol 2004; 22:1916-25; Avigan D, Clin Cancer Res 2004; 10:4699-708). Activated cytotoxic T lymphocytes (CTLs) capable of recognizing and destroying cancer cells are generated in immunized mice, and patients. The immunity is directed toward unique MHC class I restricted TAAs expressed by the malignant cells (Boon T, Curr Opin in Immunol 2003; 15:129-130; Banchereau J, Cancer Res 2001; 61:6451-8; Gajewski T F, Clin Cancer Res 2001; 7: S895-S901; Marchand M, Eur 3 Cancer 2003; 39:70-7).

Although experimental immunotherapy protocols in mice are revealing the potential of this form of treatment, effective vaccination strategies in cancer patients are wanting. One possible explanation is that even though the immune system can adversely affect diffuse and smaller tumors, it cannot effectively destroy large, established neoplasms. An immunotherapeutic strategy that would allow treatment at an early stage of the disease could have significant benefits.

Efforts to increase immunogenicity of TAA-based vaccines have ranged from using adjuvants or cytokines to genetically modified tumor cells (Offring a et al., Curr. Opin. Immunol. 12:576-58.3, 2000). Additional types of modified cell lines for use as a vaccine include transferring tumor DNA into highly immunogenic cell lines (Whiteside et al., Proc Natl Acad Sci U.S.A. 99:9415-20, 2002).

Tumor cells are the richest source of tumor antigens. Immunization with malignant cells modified to secrete immune-augmenting cytokines such as IL-2 (Fearon E R, Cell 1990; 60:397-403; Cavallo F, Cancer Res 199.3; 53:5067-70; Connor J, J Exp Med 1993; 177:1127-34.), GM-CSF (Dranoff G, Proc Natl Acad Sci (USA) 1993; 90:3539-43), IL-4 (Golumbek P T, Science 1991; 254:713-6), IL-6 (Mullen Calif., Cancer Res 1992; 52:6020-4) and IL-12 (Chen L, J Immunol 1997; 59:351-9; Tahara H, Cancer Res 1994; 54:182-9) resulted in rejection of the cytokine-secreting cells and the induction of T cell mediated immunity toward the neoplastic cells. In some instances, the induced immunity was sufficient to prolong the lives of mice with established neoplasms. However, the direct modification of cancer cells from a primary neoplasm is technically challenging. It requires the establishment of a tumor cell line, which cannot always be accomplished. This is especially the case for breast cancer in patients.

SUMMARY OF THE INVENTION

The present invention is directed to compositions comprising a combination of a chemotherapeutic agent and a genomic DNA-based vaccine. The present invention is also directed to compositions comprising a combination of a chemotherapeutic agent and a c-DNA-based vaccine. The chemotherapeutic agent may be selected from taxane, camptothecin, vinca alkaloid, anthracycline, antibiotic, antimetabolite, platinum, or alkylating agent, paclitaxel, docetaxel, vincristine, vinblastine, vinorelbine, innotecan, topotecan, etoposide, methotrexate, 5-fluorouracil, cyclophosphamide, ifosphamide, melphalan, chlorambucil, BCNU, CCNU, decarbazine, procarbazine, busulfan, thiotepa, daunorubicin, doxorubicin, idarubicin, epirubicin, or mitoxantrone, as well as other chemotherapeutic agents known to one of skill in the art. A genomic DNA-based vaccine useful as compositions of the instant invention comprises an antigen-presenting cell modified to express an allogeneic MHC-determinant, and transfected with genomic DNA isolated from a tumor of a mammal in need of cancer treatment.

A c-DNA-based vaccine useful as compositions of the instant invention comprises an antigen-presenting cell modified to express an allogeneic MHC-determinant, and transfected with c-DNA isolated from a tumor of a mammal in need of cancer treatment. A c-DNA-based vaccine and a genomic DNA-based vaccine of the invention can be used either alone or in combination with a chemotherapeutic agent.

Genomic DNA used in compositions of the instant invention can be isolated from any neoplasm cancer, including melanoma, lymphoma, plasmacytoma, sarcoma, glioma, thymoma, leukemias, breast cancer, prostate cancer, colon cancer, esophageal cancer, brain cancer, lung cancer, ovarian cancer, cervical cancer, hepatoma or any other solid or hematological cancer cells.

C-DNA used in compositions of the instant invention can be isolated from any neoplasm cancer, including melanoma, lymphoma, plasmacytoma, sarcoma, glioma, thymoma, leukemias, breast cancer, prostate cancer, colon cancer, esophageal cancer, brain cancer, lung cancer, ovarian cancer, cervical cancer, hepatoma or any other solid or hematological cancer cells.

Antigen-presenting cells used in compositions of the instant invention can be further modified to express a cytokine. For example, an antigen-presenting cell can be modified to express any of the following cytokines: IL-2, granulocyte macrophage colony stimulating factor (GM-CSF), IL-4, IL-6 or IL-12.

The present invention is also related to a method of enriching populations of immunogenic cells capable of inducing an immune response to a target cell in a patient by providing a population of immunogenic cells capable of inducing an immune response to a target cell in a patient; incubating the immunogenic cells in growth medium; diluting the immunogenic cells either before or after incubating the immunogenic cells; and optionally repeating these steps, whereby an enriched population of immunogenic cells is produced. The enriched population of immunogenic cells may be polyclonal or monoclonal. The population of immunogenic cells may be produced by introducing DNA derived from a cancer cell into a recipient cell that is syngeneic, semi-allogeneic, or allogeneic.

The present invention is also related to a method of screening immunogenic cells for the ability to induce an immune response. The ability to induce an immune response may be the in vitro or in vivo stimulation of T cells.

The present invention is also related to a method of identifying a tumor associated antigen by providing a recipient cell and an immunogenic cell capable of inducing an immune response to a tumor cell and comparing nucleic acid of the recipient cell and the immunogenic cell and identifying the nucleic acid with increased expression in the immunogenic cell as the nucleic acid encoding for a tumor associated antigen.

The present invention is also related to a method of identifying a tumor associated antigen by providing a recipient cell and an immunogenic cell capable of inducing an immune response to a tumor cell and comparing the expressed proteins of the immunogenic cell and the recipient cell and determining that the protein with increased expression in the immunogenic cell as a tumor associated antigen.

DETAILED DESCRIPTION

Figure 1:
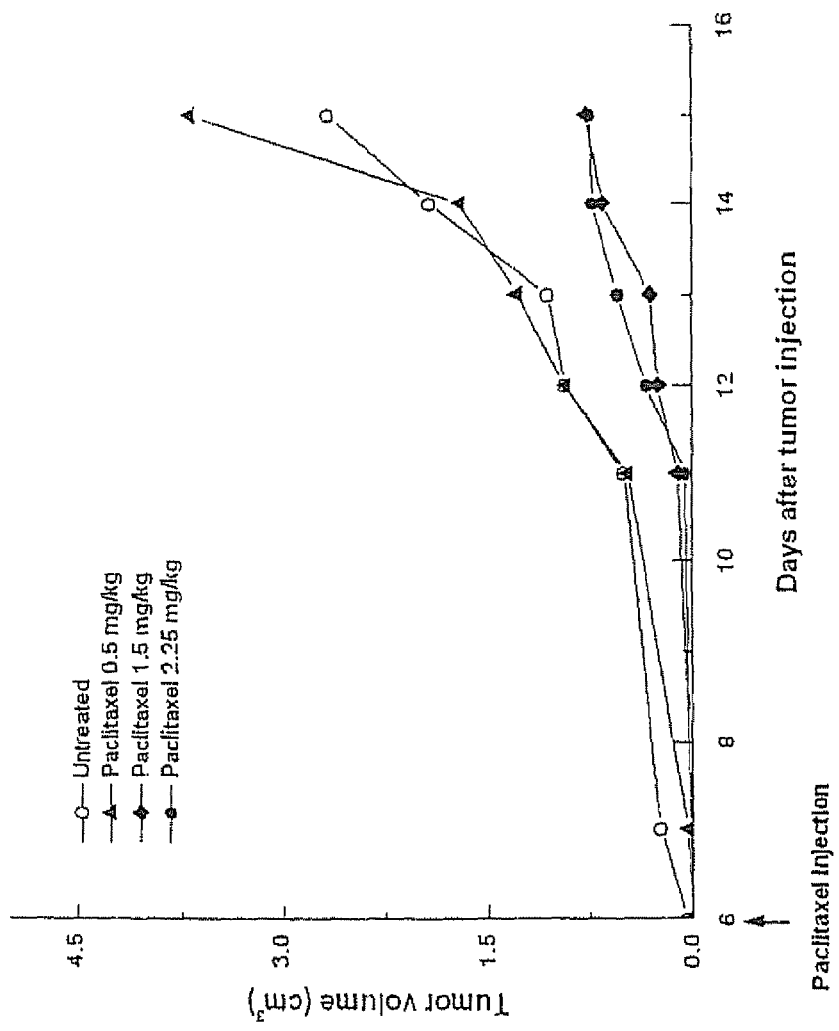
FIG. 1 depicts the effect of the paclitaxel on the growth of breast cancer cells in C3H/He mice.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and the include plural referents unless the context clearly dictates otherwise.

As used herein, "administer" includes single or multiple administrations.

As used herein, "allogeneic" refers to at least one class I or class II MHC allele of a first cell coding for an HLA specificity that is unmatched and immunologically incompatible with respect to at least one class I or class II MHC allele of a second cell.

As used herein, "semi-allogeneic" refers to at least one class I or class II MHC determinant expressed by a first cell is syngeneic with respect to a second cell and at least one class I or class II MHC determinant expressed by the first cell is allogeneic with respect to the second cell.

As used herein, "syngeneic" refers to an MHC allele coding for an HLA specificity of a first cell that matches and is immunologically compatible with a second cell.

As used herein, "treat" or "treating" when referring to protection of an animal from a condition, means preventing, suppressing, repressing, or eliminating the condition. Preventing the condition involves administering a composition of the present invention to an animal prior to onset of the condition. Suppressing the condition involves administering a composition of the present invention to an animal after induction of the condition but before its clinical appearance. Repressing the condition involves administering a composition of the present invention to an animal after clinical appearance of the condition such that the condition is reduced or prevented from worsening. Eliminating the condition involves administering a composition of the present invention to an animal after clinical appearance of the condition such that the animal no longer suffers the condition.

In mice, it was possible to treat breast cancer by immunization with a vaccine prepared by transfer of sheared total genomic DNA-fragments from various murine neoplasms, including adenocarcinoma of the breast, into a highly immunogenic, mouse fibroblast cell line (de Zoeten E, J Immunol 1999; 162:6934-41; Kim T S, Cancer Res 1994; 54:2531-5; Sun T, Cancer Gene Therapy 1998; 5:110-8). Because the transferred DNA was integrated and replicated as the recipient cells divide, the vaccine could be prepared from DNA derived from relatively small numbers of tumor cells. Sufficient DNA could be recovered from as few as 10 million cancer cells. (A tumor of 4 mm contains an equivalent number of cells.) The vaccine was readily prepared from primary neoplasms. Furthermore, since the DNA was not fractionated before transfer, it was likely that multiple mutant/dysregulated genes in the breast cancer cells specifying an array of unidentified weakly immunogenic TAAs were expressed by the transfected cells.

Several groups reported that immunization of tumor-bearing mice with the DNA-based vaccine alone was unable to successfully control the growth of the highly aggressive breast cancer (de Zoeten E, J Immunol 1999; 162:6934-41; Kim T S, Cancer Res 1994; 54:2531-5; Sun T, Cancer Gene Therapy 1998; 5:110-8).

In an attempt to improve the therapeutic outcome for patients with highly aggressive cancers, compositions and methods of the instant invention were developed. The compositions include a combination of a chemotherapeutic agent and immunization with a DNA-based vaccine such as described in and made by methods disclosed in U.S. Pat. Nos. 5,759,535 and 6,187,307 and U.S. patent application Ser. No. 09/522,716; incorporated herein by reference. The chemotherapeutic agent may be a taxane, camptothecin, vinca alkaloid, anthracycline, antibiotic, antimetabolite, platinum, or alkylating agent, and may be selected from the group consisting of paclitaxel, docetaxel, vincristine, vinblastine, vinorelbine, irinotecan, topotecan, etoposide, methotrexate, 5-fluorouracil, cyclophosphamide, ifosphamide, melphalan, chlorambucil, BCNU, CCNU, decarbazine, procarbazine, busulfan, thiotepa, daunorubicin, doxorubicin, idarubicin, epirubicin, mitoxantrone, as well as other chemotherapeutic agents known to one of skill in the art.

The present invention is also directed to compositions comprising a chemotherapeutic agent and a vaccine derived from genomic DNA taken from neoplasms and transfected into immunogenic fibroblast cells or any other antigen-presenting cells for the treatment of cancer. The present invention is also directed to compositions comprising a chemotherapeutic agent and a vaccine derived from a c-DNA obtained from neoplasms and transfected into immunogenic fibroblast cells or any other antigen-presenting cells for the treatment of cancer. According to methods of the invention, the c-DNA can be obtained by any of the methods known to a person skilled in the relevant art. These methods include, but not limited to, Polymerase Chain Reaction (PCR) on RNA templates isolated from a neoplasm with subsequent subcloning into a suitable vector as well as PCR reactions on total genomic DNA isolated from a neoplasm with subsequent subcloning into a suitable vector. Alternatively, any other techniques for isolating a gene or a portion thereof from a neoplasm can be used to obtain c-DNA of the invention. In some instances, the isolated from a neoplasm c-DNA can be cloned into a suitable vector such as a plasmid, bacteriophage, virus or an artificial chromosome.

Antigen-presenting cells may be human fibroblasts derived from donors who share identity with the cancer patient at one or more MHC class I alleles. The fibroblasts may be modified to provide immunologic specificity for cancer antigens expressed by the patient's own neoplasm.

The present invention is also directed to methods of preparation a DNA vaccine for the treatment of cancer. The vaccine can be prepared from small amounts of tumor tissue. Preferably, the vaccine is prepared using the patient's tumor tissue.

The present invention is further directed to immunization of a patient with a DNA vaccine for the treatment of cancer. Preferably, the treatment of immunization may occur in combination with treatment by one or more chemotherapeutic agents.

The vaccine can be prepared by transfer of sheared genomic DNA-fragments derived from an aggressive cancer into a highly immunogenic mouse fibroblast cell line. This unique approach was an application of classic studies indicating that the introduction of high molecular weight total genomic DNA from one cell type into another results in stable integration of the transferred DNA and alteration of both the genotype and the phenotype of the cells that incorporate the exogenous DNA (Hsu C, Nature 1984; 312:68-9; Kavathas P, Proc Natl Acad Sci (USA) 1983; 80:524-8).

Because the transferred DNA is integrated and replicated when the recipient cells divide, the number of vaccine cells can be expanded as required for multiple rounds of immunization. Thus, the vaccine could be prepared by transfer of microgram amounts of total genomic DNA derived from small quantities of tumor tissue.

Dendritic cells and fibroblasts are efficient antigen presenting cells (Kundig T M, Science 1995; 268:1343-5; Buenafe A C, J Neuroimmunol 2001; 112:12106-14; Wassenaar A, Clin Exp Immunol 1997; 110:277-84). However, other antigen presenting cells such as B cells and macrophages, may also be used in the present methods.

The fibroblasts may express MHC class I-determinants and co-stimulatory molecules required for T cell activation. The use of a fibroblast cell line enables the cells to be modified in advance of DNA transfer to augment their immunogenic properties. The fibroblasts can be modified to secrete a Th-1 cytokine (IL-2) and to express foreign (allogeneic) MHC-determinants.

In addition to their important adjuvant properties, the presence of allogeneic determinants ensures that the vaccine of the instant invention would be rejected. Thus, possible toxic effects (a tumor derived from the vaccine itself or the appearance of an autoimmune disease) are eliminated.

Human fibroblasts (derived from donors who share identity with the cancer patient at one or more MHC class I alleles) may be readily modified to provide immunologic specificity for cancer antigens expressed by the patient's own neoplasm. The technique allows the vaccine to be prepared from quite small amounts of tumor tissue, providing an opportunity to treat patients at an early stage of the disease. Immunization at an appropriate interval following chemotherapy may result in an enhanced anti tumor immune response.

Using the methods of the instant invention, tumor cells are obtained from a patient; total or whole genomic DNA from the tumor cells is then isolated by any of the methods for total genomic DNA isolation known in the art. The DNA may then be fragmented, preferably into 25 kb fragments. The vaccine may then be prepared by transferring genomic DNA-fragments (25 kb) into fibroblast cells by methods well known in the art, modified to enhance cells' immunogenic properties.

While the genomic DNA vaccine is in preparation, the patient may be undergoing chemotherapy with anti-cancer drugs such as paclitaxel, docetaxel, vincristine, vinblastine, vinorelbine, irinotecan, topotecan, etoposide, methotrexate, 5-fluorouracil, cyclophosphamide, ifosphamide, melphalan, chlorambucil, BCNU, CCNU, decarbazine, procarbazine, busulfan, thiotepa, daunorubicin, doxorubicin, idarubicin, epirubicin, or mitoxantrone or any other chemotherapeutic agent. At about 5 to 20 days after the chemotherapy is completed and when the patient regains immune competence, the patient receives an injection of genomic DNA vaccine. The injection can be repeated preferably as many times as needed. The patient may then be monitored for developing cellular immunity against his or her cancer.

The present invention is also related to the discovery that immunogenic cells expressing tumor associated antigens may be expanded and enriched into more or less highly immunogenic populations. The ability to expand immunogenic cells expressing tumor associated antigens allows immunogenic cells to be prepared using tumor DNA from a very small amount of tissue. According to the methods of the invention, murine immunogenic cells expressing tumor associated antigens may be enriched for different populations of immunogenic cells with differences in antigenicity. By enriching for immunogenic cells expressing tumor associated antigens, a more effective vaccine may be prepared. In addition, a vaccine may be prepared comprising immunogenic cells expressing a defined tumor associated antigen or combinations of defined tumor antigens. The ability to enrich immunogenic cells also allows for the identification of particular tumor associated antigens.

The present invention is also directed to an immunogenic cell expressing a tumor associated antigen. The immunogenic cell may be prepared by transfecting a recipient cell with DNA derived from a tumor cell, preferably the target tumor cell. The transfer of tumor-derived DNA may alter the phenotype of the recipient cell by expressing a tumor associated antigen. The tumor associated antigen may induce an immune response in a patient to a target tumor cell.

Tumor cells may be obtained from any source including, but not limited to, a tumor cell line or from a patient to be treated with the vaccine. The tumor cells may be selected for their general, nonspecific, immune-augmenting properties, and the range of expressed tumor associated antigens that characterize the tumor, including antigens that may be present on only a small proportion of the tumor cells.

The tumor cells may be obtained from tumors during surgery. Alternatively, the tumor cells may be obtained from a biopsy as described in Heo et al., Cancer Res. 49: 5167-5175, 1989. The tumor cells may be obtained from primary tumors or from metastases.

The cancer cells may be obtained from any cancer type including, but not limited to, carcinomas, melanoma, lymphoma, plasmacytoma, sarcoma, glioma, thymoma, leukemias, breast cancer, prostate cancer, colon cancer, esophageal cancer, brain cancer, lung cancer, ovarian cancer, cervical cancer, or hepatoma. The isolated tumor cells may be cultured and propagated using standard techniques.

The tumor-derived DNA used to produce the immunogenic cell may be derived from any form of nucleic acid of the tumor cell including, but not limited to, total genomic DNA, cDNA and RNA. The nucleic acid of the tumor cell may be isolated using standard techniques. For methods of isolating nucleic acid, see Current Protocols in Molecular Biology, Editors John Wiley & Sons, 2003. The tumor-derived DNA is then preferably mechanically sheared or cut with an appropriate restriction enzyme to render high molecular weight DNA fragments of preferably about 20-25 Kb.

The tumor-derived DNA may be used to transfect the recipient cell using methods including, but not limited to, lipofection, calcium phosphate, cationic liposome-mediated transfection, electroporation, and ballistomagnetic gene delivery as described in Wittig et al., Hum. Gene Ther. 12:267-278, 2001. Representative methodologies for transfecting recipient cells are discussed in Example 4.

Recipient cells may be co-transfected with sheared genomic DNA isolated from tumor cells and plasmid DNA with a selectable marker, such as an antibiotic-resistance marker. The selectable marker allows for the selection of recipient cells that have taken up the tumor-derived DNA. Representative examples of plasmids with selectable markers include, but are not limited to hygromycin B phosphotransferase, which confers resistance to hygromycin.

The recipient cell may be any cell that is capable of being transformed with the tumor-derived DNA and capable of expressing the genes encoded by the tumor-derived DNA. The recipient cell is preferably an antigen presenting cell including, but not limited to fibroblasts, macrophages, dendritic cells, B cells, monocytes, marginal zone Kupffer cells, microglia, Langerhans' cells, interdigitating dendritic cells, follicular dendritic cells, B cells, and T cells. Antigen presenting cells preferably express MHC, thereby allowing presentation of the tumor associated antigens for inducing an immune response by binding with a T-cell with the appropriate receptor. The recipient cell may be selected based on the expression of defined MHC determinants.

The recipient cell may be isolated or derived from a patient to be administered the vaccine. In such a case, the immunogenic cells may be used to produce an autologous vaccine. The use of an autologous vaccine may be advantageous to minimize the induction of an immune response to antigens other than the tumor associated antigens. The recipient cell may also be isolated or derived from a source other than the patient to be administered the vaccine. In such a case, the immunogenic cells may be used to produce a heterologous vaccine, which may be syngeneic, semi-allogeneic, or allogeneic. The use of a heterologous vaccine may be useful to induce a stronger immune response to the tumor associated antigens by using heterologous antigens as an adjuvant.

The use of semi-allogenic cells as recipient cells provides a mechanism through the expression of syngeneic MHC determinants for the direct presentation of tumor associated antigens to T cells. The presence of allogeneic MHC determinants provides an adjuvant stimulus to the immune system and ensures that the vaccine, like any other foreign tissue graft, will be rejected.

When the tumor associated antigen is expressed into the cytoplasm, the recipient cell preferably expresses MHC Class I. MHC Class I activates cytotoxic T cells and is expressed on most nucleated cells. The recipient cell may also be fed to a secondary recipient cell. In such a case, the recipient cell may first be induced to undergo apoptosis, as described in (Whiteside et al., Proc Natl Acad Sci USA. 99:9415-20, 2002). By feeding the recipient cell to the secondary recipient cell, the tumor associated antigens expressed by the recipient cell may become localized in acid vesicles of the secondary recipient cell. In such a case, the secondary recipient cell preferably expresses MHC Class IL MI-IC Class II activates helper T cells and is constitutively expressed on cells including, but not limited to, B lymphocytes, dendritic cells and thymic epithelial cells, but expression may be induced in other cells by using activating factors, such as IFN-γ. The use of "recipient cell" herein is intended to also encompass "secondary recipient cell," unless the context dictates otherwise.

Representative examples of recipient cells include, but are not limited to, dendritic cells, fibroblasts, bone marrow cells (e.g., lymphocytes including B cells), adipocytes, muscle cells and endothelial cells. Fibroblasts may be isolated from a patient to be treated with a vaccine. Fibroblasts may also be isolated from donors including, but not limited to, foreskin of circumcised neonatals.

The recipient cell may be modified to secrete immune-augmenting cytokines or to express co-stimulatory molecules. The use of recipient cells secreting cytokines or expressing co-stimulatory molecules may be used to increase the immune response of a vaccine. Representative examples of such cytokines include, but are not limited to, interleukin-1, interleukin-2, interleukin-3, interleukin-4, interleukin-5, interleukin-6, interleukin-7, interleukin-8, interleukin-9, interleukin-10, interleukin-11, interleukin-12, interleukin 18, interferon-α, interferon-γ, tumor necrosis factor, granulocyte macrophage colony stimulating factor, and granulocyte colony stimulating factor. The recipient cell may be modified to express a desired cytokine using standard methods including, but not limited to, those described in U.S. Pat. No. 6,187,307, the contents of which are incorporated herein by reference.

The present invention is also related to methods of screening for immunogenic cells capable of inducing an immune response to a target cell in a patient. The immunogenic recipient cells may induce an immune response to different tumor associated antigens. As a result, screening for certain immunogenic recipient cells may allow the production of a vaccine capable of inducing a more robust or effective immune response against the target cell.

Immunogenic recipient cells may be screened for the ability to induce an immune response to tumor cells, preferably the tumor cells that provided the tumor-derived DNA. The immunogenic cells may be incubated with T-cells from a patient, or T-cells representative of a patient. The stimulated T-cells may then be incubated with a target antigen or target cell expressing a tumor associated antigen. T-cells capable of responding to a particular target antigen or target cell expressing a tumor associated antigen may be identified by methods including, but not limited to, $^{51}Cr$, release assay or by ELISPOT, as described in Asai et al., Clin. Diagn. Lab, Immunol. 7: 145-154, 2000. Screening using ELISPOT also allows for distinction of allo- from tumor-specific responses by blocking with MHC class I or class II antibodies.

Immunogenic recipient cells may also be screened by the ability to inhibit tumor formation. The immunogenic cells may be administered to a test animal that has also been administered the same tumor cells that provided the tumor DNA. After a sufficient period of time for tumors to develop in control animals that do not receive immunogenic recipient cells, the test animals are checked for tumor formation, and the size of any tumors measured. Representative examples of screening for immunogenic cells by the ability to inhibit tumor formation are shown in Example 10 and Example 12.

The present invention is also related to the enrichment of immunogenic cells expressing a tumor associated antigen capable of inducing an immune response. Not every transfected recipient cell will be immunogenic. For example, not every recipient cell will be transfected with DNA encoding a tumor associated antigen. Alternatively, the tumor associated antigen may not be sufficiently presented by the recipient cell to induce an immune response, or T cells may be tolerant to a particular combination of MHC and bound tumor associated peptide. By enriching for immunogenic cells expressing a tumor associated antigen capable of inducing an immune response, the immunogenic cells may be used to produce a more effective vaccine. Enrichment of immunogenic cells also allows the production of a vaccine using small amounts of starting material, because the recipient cells may replicate the transferred DNA encoding tumor associated antigens as they divide.

According to the present invention, populations of immunogenic cells prepared by the methods of the present invention may be enriched by providing a composition comprising a plurality of immunogenic recipient cells. The immunogenic recipient cells may be diluted into growth medium and allowed to expand. The immunogenic cells may then be, in any order, divided into pools and screened for the ability to induce an immune response. The steps of dilution and expansion may be repeated as often as desired in order to obtain a desired number of immunogenic recipient cells or to obtain a desired clonal population of immunogenic recipient cells. The present invention is also related to an enriched population of immunogenic recipient cells. The enriched population of immunogenic recipient cells may be polyclonal or monoclonal.

The present invention is also related to the identification of tumor associated antigens. Immunogenic recipient cells capable of inducing an immune response may be analyzed to determine the tumor associated antigen giving rise to the immune response. The tumor associated antigen may be determined by comparing the genomic DNA, mRNA or expressed proteins of the immunogenic recipient cell to an untransfected recipient cell. The additional genomic DNA, mRNA or expressed protein of the immunogenic recipient cell will correlate to the tumor associated antigen. Differences in mRNA levels may be determined by methods including, but not limited, the use of Affymetrix Genome Gene-Chips as described in U.S. Pat. No. 6,344,316, the contents of which are incorporated by reference. Differences in protein levels may be determined according to methods of proteomics known in the art.

The present invention is also related to a vaccine comprising enriched immunogenic recipient cells. The vaccine may be more effective at inducing an immune response to a target tumor cell than previously used vaccines. The immunogenic recipient cells of the vaccine many polyclonal or monoclonal. A monoclonal vaccine may be used to induce an immune response to a single tumor associated antigen. A polyclonal vaccine may be used to induce an immune response to multiple epitopes of one or more tumor associated antigens. The polyclonal vaccine may be prepared by pooling multiple clonal or polyclonal populations of enriched recipient cells.

The vaccine may comprise a therapeutically acceptable carrier. As used herein, a therapeutically acceptable carrier includes any and all solvents, including water, dispersion media, culture from cell media, isotonic agents and the like that are non-toxic to the host. Preferably, it is an aqueous isotonic buffered solution. The use of such media and agents in therapeutic compositions is well known in the art. Except insofar as any conventional media or agent is incompatible with the immunogenic recipient cells, the use of such conventional media or agent in the vaccine is contemplated. Supplementary active ingredients can also be incorporated into the vaccine.

The vaccine may be administered to an animal in need thereof. The vaccine may be administered for inducing an immune response in an animal in need of such response. The animal may be administered an immunologically effective amount of immunogenic recipient cells. The precise amount of "an immunologically effective amount" of immunogenic recipient cells may be determined by a physician with consideration of individual differences in age, weight, tumor size, extent of infection or metastasis, and condition of the animal.

The vaccine may be administered to treat a cancer in an animal. The cancers which may be treated by the vaccine include, but are not limited to, melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, hepatoma, and other neoplasms known in the art, such as those described by Shawler et al. (1997).

The immune response induced in the animal by administering the vaccine may include cellular immune responses mediated primarily by cytotoxic T cells, capable of killing tumor cells, as well as humoral immune responses mediated primarily by helper T cells, capable of activating B cells thus leading to antibody production. A variety of techniques may be used for analyzing the type of immune responses induced by the immunogenic recipient cells, which are well described in the art; e.g., Coligan et al. Current Protocols in Immunology, John Wiley & Sons Inc. (1994).

The vaccine may be administered at a dosage of from about $1 \times 10^3$ to about $5 \times 10^9$ cells per administration. The vaccine may be administered to an animal in any convenient manner including, but not limited to, aerosol inhalation, injection, ingestion, transfusion, implantation or transplantation. Preferably, the vaccine is administered by subcutaneous (s.c.), intraperitoneal (i.p.), intra-arterial (i.a.), or intravenous (i.v.) injection.

Throughout this application, where publications are referenced, the disclosures of these publications in their entireties are hereby incorporated by reference into this application in order to more fully describe the state of the art to which this invention pertains.

When evaluating results of the treatment, the following statistical analysis may be used. Kaplan-Meier log rank analyses may be used and was used in the examples of this application to determine the statistical differences between the survival of mice in the various experimental and control groups. A p value less than 0.05 is considered significant. Student t test one-way Anova may be used and was used in the examples of this application to determine statistical difference between experimental and control groups in the in vitro experiments.

The present invention has multiple aspects, illustrated by the following non-limiting examples.

Example 1

Cytokine-Secretion by LM Mouse Fibroblasts

Among other advantages, the use of a fibroblast cell line as the recipient of genomic DNA from the breast cancer cells enables the recipient cells to be modified in advance of DNA-transfer to augment their nonspecific immunogenic properties. In this instance, the fibroblasts were modified to secrete IL-2 and to express allogeneic MHC class I-determinants. IL-2 is a growth and maturation factor for CTLs.

A replication-defective retroviral vector (pZipNeoSVIL-2) was used to modify the fibroblasts used as DNA-recipients to secrete IL-2 (pZipNeoSV-IL-2; from M. K. L. Collins, University College, London, England) specifying human IL-2 was used for this purpose. The IL-2-specifying vector was packaged in GP-1-env AM 12 cells (from A. Bank, Columbia University, New York, N.Y.). The vector also included a neo$^r$ gene under control of the Moloney leukemia virus long terminal repeat. The neo$^r$ gene conferred resistance to the aminoglycoside antibiotic neomycin-derivative, G418 (Gibco BRL), used for selection.

Virus-containing supernatants of GP+env AM12 cells transduced with pZipNeoSV-IL-2 were added to the fibroblasts, followed by overnight incubation at 37° in growth medium containing polybrene (Sigma; 5 mg/ml, final concentration). The cells were maintained for 14 days in growth medium containing 400 µg/ml G418 (Gibco BRL). One hundred percent of non-transduced cells died in medium supplemented with G418 during this period. Colonies of cells proliferating in the G418-containing growth medium were pooled and maintained as modified cell lines for later use in the experiments. An ELISA (BioSource, Camarillo, Calif.) was used to determine the quantity of IL-2 secreted by the transduced fibroblasts (LM-IL-2 cells) which indicated that $10^6$ retrovirally-transduced cells formed 196 pg IL-2/ml/48 hrs.

The culture supernatants of LM fibroblasts transduced with the IL-2 negative vector pZipNeoSV(X), like that of non-transduced LM cells, failed to form detectable quantities of IL-2. Every third passage, the transduced cells were placed in medium containing 600 µg/ml G418. Under these circumstances, equivalent quantities of IL-2 were detected in the culture supernatants of cells transduced with pZipNeoSVIL-2 for more than six months of continuous culture. The generation time of transduced and non-transduced fibroblasts, approximately 24 hrs in each instance, were equivalent. The introduction of DNA from the breast cancer cells into the IL-2-secreting cells did not affect the quantity of IL-2-secreted (these data are not presented).

Example 2

Modification of the Cytokine-Secreting Fibroblasts to Express H-2K$^b$-Class Determinants Allogeneic class I-determinants are strong immune adjuvants (Conte P F, Cancer 2004; 101:704-12; Hammerling G J, J Immunogen 1986; 13:15-157; Hui K M, J Immunol 1989; 143:3835-43; Ostrand-Rosenberg S, J Immunol 1990; 144: 4068-71). To further augment their immunogenic properties, the fibroblasts were modified to express MHC H-2K$^b$-determinants, allogeneic in C3H/He mice. A plasmid (pBR327H-2K$^b$) (Biogen Research Corp., Cambridge, Mass.) encoding H-2K$^b$-determinants was used. Ten g of pBR327H-2K$^b$ and 1 g of pBabePuro (from M. K. L. Collins), a plasmid specifying a gene that confers resistance to puromycin, were mixed with Lipofectin (Gibco BRL), and added to $1 \times 10^6$ cytokine-secreting fibroblasts in 10 ml of DMEM, without FBS. (A 10:1 ratio of tumor-DNA to plasmid DNA was used to increase the likelihood that cells converted to puromycin-resistance took up tumor-DNA as well.)

The IL-2-secreting fibroblasts were incubated under standard cell culture conditions for 18 hr at 37° in growth medium. After incubation, the cell cultures were divided and replated in complete growth medium supplemented with 3.0 µg/ml puromycin (Sigma; St. Louis, Mo.), followed by incubation at 37° for 7 additional days. The surviving colonies were pooled and maintained as a cell line for later use (LM-IL-2K$^b$ cells). One hundred percent of non-transduced cells maintained in growth medium containing equivalent amounts of puromycin died during the seven-day period of incubation.

Quantitative immunofluorescence staining with FITC-labeled mAbs for mouse H-2Kb determinants was used to measure expression of the class I-determinants. The following protocol was followed for the staining. The measurements were performed in an Epic V flow cytofluorograph (Coulter Electronics, Hialeah, Fla.) equipped with a multiparameter data-acquisition and display system (MDADS). For the analysis, 0.1 mM EDTA in PBS was used to disassociate the monolayer cultures from plastic cell culture flasks. The cell-suspensions were washed with PBS containing 0.2% sodium azide and 0.5% FBS. Afterward, FITC-conjugated H-2K$^k$, H-2K$^b$, I-Ak, B7.1, B7.2 or ICAM-1 mAbs (Pharmingen, San Diego, Calif.) were added to the cell-cultures, followed by incubation at 4° for 1 hr. The cells were then washed with PBS containing 0.5% FBS and 0.2% sodium azide. Background staining was determined by substituting FITC-conjugated IgG2a isotype serum (DAKO, Carpenteria, Calif.) for the specific mAbs. One-parameter fluorescence histograms were generated by analyzing at least $1 \times 10^4$ cells in each instance.

As a control, aliquots of the puromycin-resistant cell suspension were incubated with FITC-conjugated IgG2a isotype serum. As an additional control, spleen cells from C57BL/5 mice (H-2$^b$) were substituted for the transduced fibroblasts. After incubation, the cells were washed and analyzed for fluorescent staining by flow cytofluorometry. The dark-shaded area indicates transduced cells stained with PE-conjugated anti-H-2K$^b$ mAbs. The light line indicates transduced cells incubated with PE-conjugated isotype serum. The dark line indicates spleen cells from C57BL/6 mice (H-2$^b$).

Figure 2:
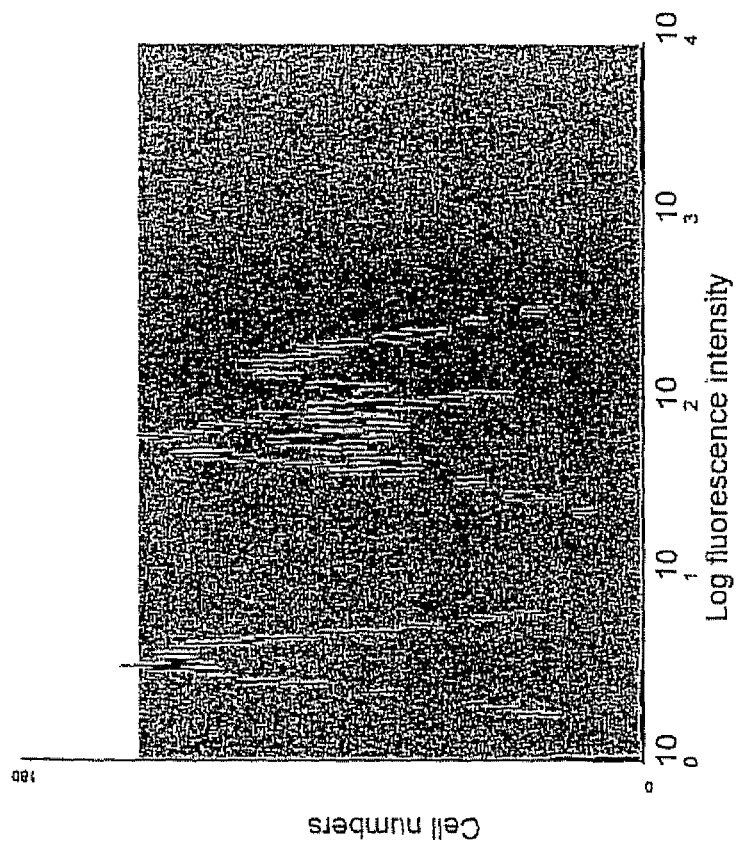
FIG. 2 depicts expression of MHC class I H-2K$^b$-determinants by LM fibroblasts transduced with the plasmid vector pBR327H-2K$^b$.

The results of procedure (FIG. 2) indicated that more than 99 percent of the transduced fibroblasts stained positively (mean fluorescence index (MFI) at least ten fold greater than cells stained with FITC-conjugated isotype serum, taken as background). Under similar conditions, non-transduced fibroblasts or fibroblasts incubated with FITC-conjugated isotype serum failed to stain. The expression of H-2Kb-determinants by the transduced cells was a stable property. The staining intensity was essentially unchanged after three months of continuous culture.

An analogous procedure was used to further characterize the cells used as DNA-recipients. The modified fibroblasts were stained with FITC-labeled mAbs for H-2Kk class I-determinants, FITC-labeled I-Ak or with FITC-labeled mAbs for the co-stimulatory/cell adhesion molecules B7.1, B7.2 and ICAM-1. The results indicated that 99 percent of the fibroblasts, derived from C3H/He mice, expressed H-2Kk and B7.1 determinants constitutively (mean fluorescence index five fold greater than the control (substitution of FITC-labeled isotype serum for the mAbs, taken as background), Cells incubated with FITC-labeled ICAM-1, B7.2 or I-Ak mAbs failed to stain above background (these data are not presented.) The expression of MHC class I-determinants and the co-stimulatory molecule by LM cells was consistent with various reports indicating that fibroblasts, like dendritic cells, are efficient antigen presenting cells (Kundig T M, Science 1995; 268:1343-5; Buenafe A C, J Neuroimmunol 2001; 112:12106-14; Wassenaar A, Clin Exp Immunol 1997; 110: 277-84; Chesney J, Proc Natl Acad Sci (USA) 1997; 94; 6307-12).

Example 3

Paclitaxel Inhibited the Growth of Breast Cancer Cells in C3H/He Mice

Paclitaxel is a potent inhibitor of cell division (Ross J L, Proc Natl Acad Sci (USA) 2004; 101:12910-5; Nettles J H, Science 2004; 305:866-9; Gaitanos T N, Cancer Res 2004; 64:5063-7). It blocks cells in the G2/M phase of replication through its effect on the formation and function of microtubules within the cell. To determine if paclitaxel affected the growth of the breast cancer cells used in the experiments described here, naïve C3H/He mice were injected into the fat pad of the breast with 1×10⁵ of the malignant cells (SB5b cells). Six days after injection of the cancer cells, the mice received a single i.p. injection of varying amounts of paclitaxel (range=0.5 to 2.25 mg/kg). The effect of paclitaxel on the growth of SB5b cells was determined by measurements of tumor volume at varying times afterward (FIG. 1).

Mean tumor volumes were determined by the equation 0.5 l×w² where l=length and w=width. The dimensions of the tumor were obtained with a dial caliper. There were three mice in each group.

The results (FIG. 1) indicated that tumor growth occurred at the injection site in each instance, including that of mice treated with the highest dose of paclitaxel tested.

Paclitaxel is highly toxic. Since mounting an effective immune response requires robust cell proliferation following antigen administration, peripheral white blood counts were measured at varying times after an injection of paclitaxel. The objective was to administer the vaccine when the white blood count returned at least to its pre injection value. The results indicated that six days after a single injection of 2.25 mg/kg paclitaxel, the white blood count had returned to pre-injection levels, consistent with a full recovery from the toxic effects of the drug (these data are not presented).

Example 4

Isolation of Total Genomic DNA from Cancer Cells and Preparation of Vaccine

Eight to 10 week old pathogen-free C3H/HeJ female mice and DBA/2 female mice (H-$2^d$) were from the Jackson Laboratory (Bar Harbor, Me.). The animals, between 10 to 14 weeks old when used in the experiments, were maintained according to NIH Guidelines for the Care and Use of Laboratory Animals. SB5b cells were a short-term passage adenocarcinoma of the breast cell line derived from a breast neoplasm that arose spontaneously in a C3H/He mouse in our animal colony. B16 cells, a melanoma cell line of C57BL/6 origin, were obtained originally from I. Fidler (M. D. Anderson, Houston, Tex.). The cells were maintained by serial passage in histocompatible C3H/HeJ or C57BL6J mice respectively, or at 37° in a humidified 7% $CO_2$/air atmosphere in Dulbecco's modified Eagle's medium (DMEM) (Gibco BRL, Grand Island, N.Y.) supplemented with 10% heat inactivated fetal bovine serum (FBS) (Sigma, St. Louis, Mo.) and antibiotics (Gibco BRL) (growth medium).

KLN205 cells, a squamous carcinoma cell line derived from a lung neoplasm that arose spontaneously in a DBA/2 mouse, were from the American Type Culture Collection (ATCC). LM cells, a fibroblast cell line of C3H/He mouse origin, were also from the ATCC. KLN205 cells were maintained by serial passage in histocompatible DBA/2 mice, or at 37° in a humidified 7% CO2/air atmosphere in DMEM (Gibco BRL, Grand Island, N.Y.) supplemented with 10% heat inactivated fetal bovine serum (FBS) (Sigma, St. Louis, Mo.) and antibiotics (Gibco BRL) (growth medium). LM cells were maintained in growth medium under the same conditions. mAbs for CD8+, CD4+ and NK1.1 determinants were from Pharmingen, (San Diego, Calif.). Low tox rabbit complement (C) was from Pel Freeze, (Rogers, Ark.).

A DNeasy isolation kit (Qiagen, Valencia, Calif.) was used to obtain genomic DNA from the breast cancer cells or KLN205 cells, according to the manufacturer's instructions. In brief, 1×10⁷ actively proliferating plastic adherent breast cancer cells from in vitro culture were disassociated from the plastic by treatment with EDTA ($10^{-4}$ M). The cell suspension was centrifuged at 300×g for 5 min. Afterward, the cell pellet was re suspended in 200 µl PBS followed by the addition of 400 µg RNase A and incubation at RT for 2 min. After incubation, 12 mAU proteinase K and 200 l lysis buffer containing guanidine HCl were added, followed by further incubation at 70° for 10 min. Afterward, 200 µl of 100% ethanol was added. The extracted DNA was loaded onto the DNeasy spin column, and eluted after two washes with buffer. The $A_{260}/A_{280}$ ratio of the isolated DNA was greater than 1.8 in each instance. The molecular size of the extracted DNA was approximately 25 kb, as determined by agarose gel electrophoresis. The same procedure was followed to isolate DNA from B16 cells, a melanoma cell line.

The vaccine was prepared by transfer of sheared, unfractionated total genomic DNA-fragments from SB5b breast cancer cells or KLN205 cells into LM fibroblasts, which had been modified to secrete IL-2 and to express $H-2K^b$-determinants. The method described by Wigler et al. (Wigler M, Proc Natl Acad Sci (USA) 1979; 76:1373-6) was used, as modified. In brief, 50 µg of sheared (25 kb) genomic DNA derived from approximately 1×107 breast cancer cells was mixed with 5 µg pHyg (from L, Lau, University of Illinois at Chicago), a plasmid that encoded the E. Coli enzyme hygromycin B phosphotransferase gene, conferring resistance to hygromycin B, used for selection. The sheared DNA and pHyg were mixed with Lipofectin, according to the manufacturer's instructions (Gibco BRL) and added to 1×10⁷ modified fibroblasts divided 24 hrs previously into ten 100 mm plastic cell culture plates. Eighteen hrs after the addition of the DNA/Lipofectin mixture to the cells, the growth medium was replaced with fresh growth medium containing sufficient quantities of hygromycin (500 µg/ml; Boehringer Mannheim, Indianapolis, Ind.) to kill 100 percent of the non-transfected cells. For use as a control, 5 µg of pHyg alone mixed with Lipofectin was added to an equivalent number of the modified fibroblasts. For use as a control, the same procedure was followed except that DNA from B16 melanoma cells was substituted for DNA from SB5b cells. In each instance, the cells were maintained for 14 days in growth medium containing 500 µg/ml hygromycin B. None of the non-transfected cells maintained in the selection medium were viable by the end of this period. The remaining colonies (at least 2×10⁴) were pooled and maintained as cell lines for use in the experiments (LM-IL-2Kb/SB5b cells and LM-IL-2Kb/B16 cells respectively).

Alternatively to lipofection, genomic DNA can be delivered into recipient cells by other methods such as calcium phosphate precipitation or ballistomagnetic gene delivery. If phosphate precipitation was used, then tumor-derived DNA (10-100 µg) was diluted with water, mixed with 2M $CaCl_2$ and 2× Hanks' balanced salt solution by bubbling. The DNA solution was then added to semiconfluent monolayers of recipient cells in transfection medium (DMEM plus 10% FCS containing 25 µM chloroquine; Sigma). The cells were then incubated at 37° C. in a humidified atmosphere of 5% $CO_2$ in air for 10 h before selection.

When ballistomagnetic gene delivery was used, gold particles (0.8-1.6 µm; ABCR, Karlsruhe, Germany) were coated with tumor-derived DNA and superparamagnetic beads (65 nm; Miltenyi Biotec, Auburn, Calif.) at the ratio of 1:3. The particles were then propelled at 1,550 psi into recipient cells in 30-mm² dishes using modified ballistic system (PDS-1000/He; Bio-Rad). Immediately after DNA transfer, fresh medium was added and the cells were incubated for 24 or 48 h before microscopic examination.

Example 5

Immunity to Breast Cancer in Mice Immunized with LM-IL-2K$^b$/SB5b Cells

C3H/He mice are highly susceptible to the growth of SB5b cells. The survival time of untreated mice injected into the fat pad of the breast with as few as $1 \times 10^5$ SB5b cells is 20-30 days.

To determine if the vaccine induced immunity to breast cancer in tumor-free C3H/He mice, (inhibition of tumor growth and survival), naïve mice received a single s.c. injection of $5 \times 10^6$ LM-IL-2Kb/SB5b cells. Fourteen days later, the mice were injected into the fat pad of the breast with $1 \times 10^5$ SB5b cells. As a control, naïve C3H/He mice were injected into the fat pad of the breast with an equivalent number of SB5b cells. To determine if paclitaxel augmented the vaccine's therapeutic effect, the same protocol was followed except that the mice were injected with the drug two days before the injection of the vaccine.

Figure 3:
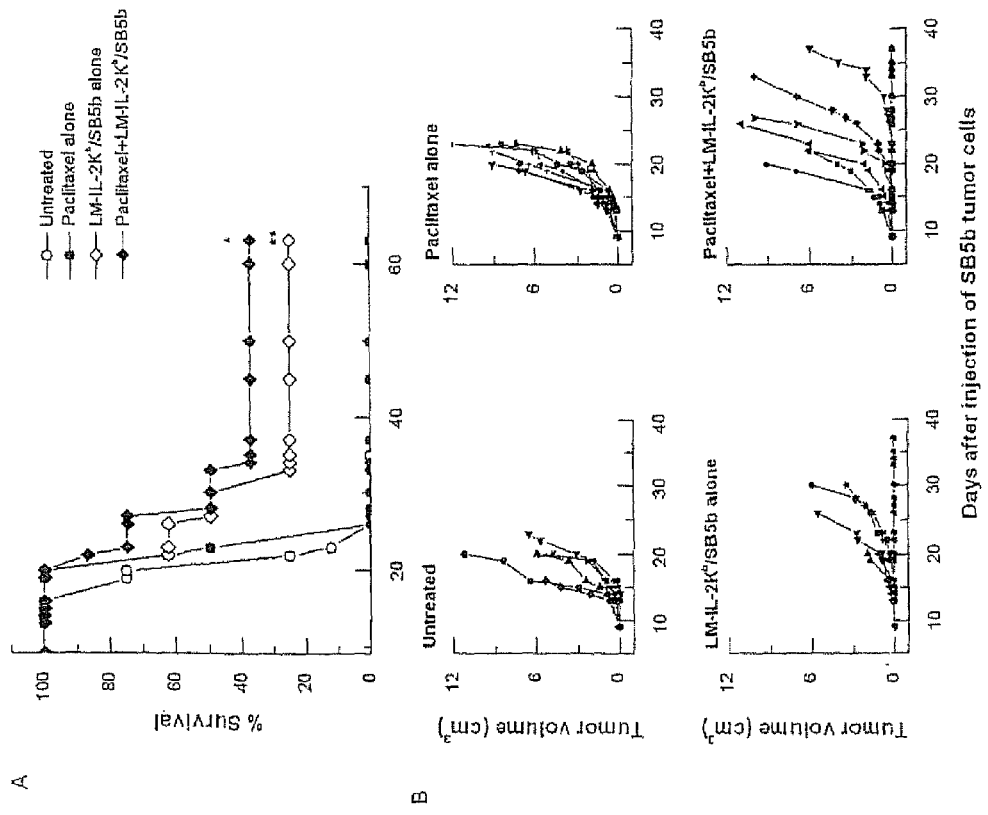
FIG. 3 depicts that immunization with LM-IL-2K$^b$/SB5b cells inhibits the growth of SB5b breast cancer cells in C3H/He mice.

In FIG. 3(A), C3H/He mice (10 mice per group) received a single i.p. injection of (2.25 mg/kg) paclitaxel. Two days later, the mice were injected s.c. with $5 \times 10^6$ LM-IL-2K$^b$/SB5b cells (vaccine). Fourteen days afterward, the mice were injected into the fat pad of the breast with $1 \times 10^5$ SB5b cells. As controls, the mice were injected according to the same schedule with an equivalent number of SB5b tumor cells alone, with paclitaxel and SB5b cells, or with LM-IL-2K$^b$/SB5b cells and SB5b cells. The experiment was terminated at day 63. Mean survival time±SE: injected with SB5b cells alone 20±1 days; injected with paclitaxel and SB5b cells, 22±1 days, injected with LM-IL2K$^b$/SB5b cells 14 days before the injection of SB5b cells, 30±3 days, injected with paclitaxel two days before the injection of LM-IL-2K$^b$/SB5b cells, followed by the injection of SB5b cells 14 days later, 35±3 days* p<0.001 for the difference in survival of mice injected with paclitaxel and LM-IL-2K$^b$/SB5b cells or LM-IL-2K$^b$/SB5b cells alone followed by SB5b cells, and mice injected with SB5b cells alone, or mice injected with paclitaxel alone followed by SB5b cells.

In FIG. 3(B), C3H/He mice were injected i.p. with 2.25 mg/kg paclitaxel. Two days afterward, the mice were injected s.c. with $5 \times 10^6$ LM-IL-2K$^b$/SB5b cells. Fourteen days later, the mice were injected into fat pad of the breast with $1 \times 10^5$ SB5b cells. As controls, the mice were injected according to the same schedule with paclitaxel followed by SB5b cells, with the vaccine alone followed by SB5b cells or with SB5b cells alone. The experiment was terminated at day 38. Tumor volumes were determined by $0.5 \, l \times w^2$. Length and width were obtained with the aid of a dial caliper.

The results (FIG. 3A) indicated that one hundred percent of the animals in the control groups injected with SB5b cells alone or with SB5b cells and paclitaxel alone died within 27 days. In contrast, mice injected with the vaccine, followed by the injection of SB5b cells survived for significantly longer periods than naïve mice in the control groups (p<0.001).

Two of 10 mice immunized with LM-IL-2Kb/SB5b cells, followed by the challenging injection of SB5b cells, appeared to have rejected the breast cancer cells. They survived indefinitely (more than 62 days). Paclitaxel had no significant effect. The survival of mice injected with paclitaxel, followed by immunization with LM-IL-2Kb/SB5b cells before the injection of SB5b cells, was essentially the same as that of mice injected with the vaccine alone (FIG. 3A).

Measurements of tumor growth in the preimmunized mice injected with the breast cancer cells were consistent with the vaccine's immunoprotective properties (FIG. 3B). Tumor growth was inhibited both in mice immunized with the vaccine and in mice injected with paclitaxel and the vaccine before the injection of the breast cancer cells.

To further investigate the vaccine's immunogenic properties, spleen cells from C3H/HeJ mice immunized with LM-IL-2Kb/SB5b cells in vitro and were then tested in $^{51}$Cr-release cytotoxicity assays. For this test, spleen cell suspensions were obtained from mice that had received a single subcutaneous injection of $5 \times 10^6$ LM-IL-2Kb/SB5b cells 14 days previously. After washing, the cells were co-incubated under standard cell culture conditions for 5 days with (mitomycin C-treated) SB5b cells. The incubation medium consisted of RPMI-1640 medium (Gibco BRL) supplemented with 100 U/ml human IL-2, 10% FBS, $5 \times 10^{-2}$ mmol 2-mercaptoethanol, 15 mmol HEPES, 0.5 mmol sodium pyruvate and penicillin/streptomycin (Gibco). The ratio of spleen cells to mitomycin-C-treated breast cancer cells during the co-incubation was 30:1. At the end of the 5 day incubation period, the population that failed to adhere to the plastic cell culture flasks was collected and used as the source of effector cells for the cytotoxicity determinations.

For the cytotoxicity assay, $5 \times 10^6$ SB5b cells were labeled with $^{51}$Cr during a 1 hr incubation period at 37° in growth medium containing 100 µCi Na$^2$ $^{51}$Cr$_{O4}$ (Amersham, Arlington Heights, Ill.) After three washes with DMEM, $1 \times 10^4$ $^{51}$Cr-labeled cells were incubated for 4 hrs at 37° with the effector cell-population. The quantity of isotope released was measured in a gamma counter (Beckman, Palo Alto, Calif.). The percent specific cytolysis was calculated as: Experimental $^{51}$Cr release minus Spontaneous $^{51}$Cr release divided by Maximum $^{51}$Cr release minus Spontaneous $^{51}$Cr release and multiplied by one hundred. The spontaneous release of $^{51}$Cr was less than 15% of the total release in each instance.

Figure 4:
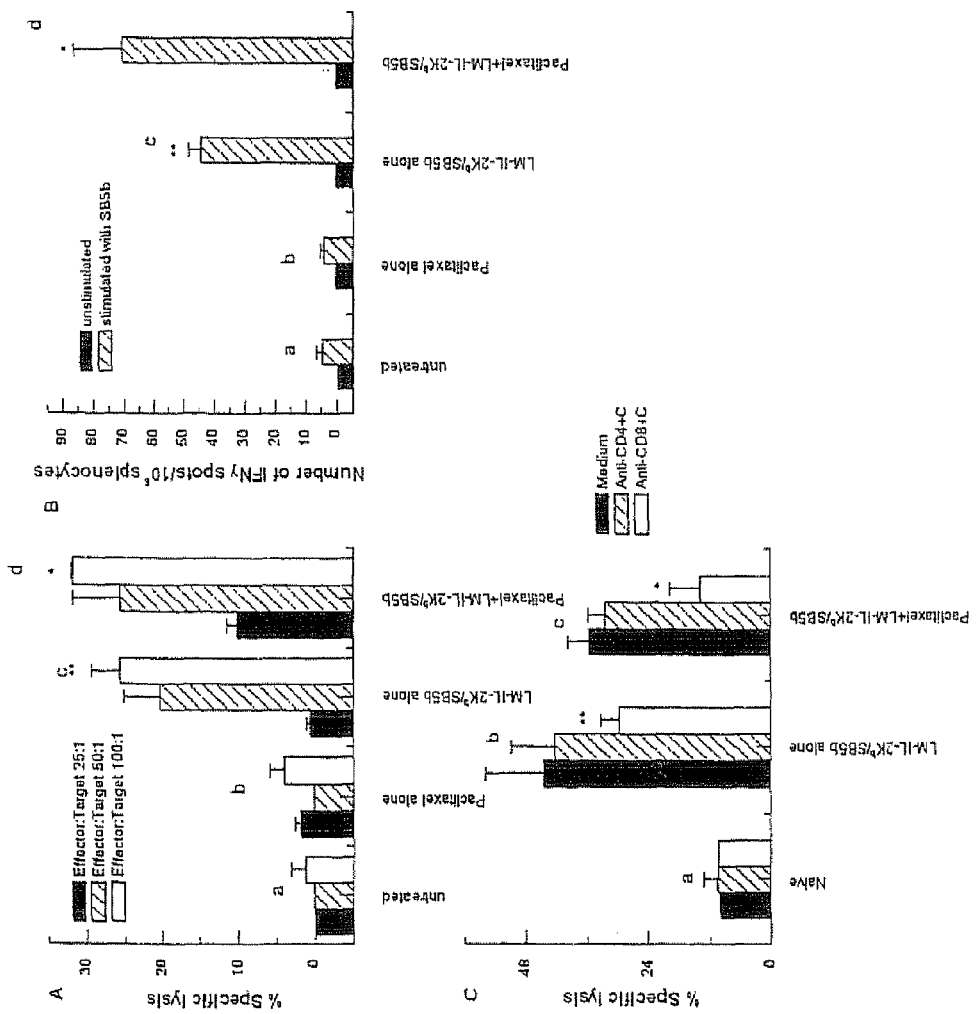
FIG. 4 depicts immunity to breast cancer in C3H/He mice receiving combined treatment with paclitaxel followed by immunization with LM-IL-2K$^b$/SB5b cells.

In FIG. 4(A), the same protocol as described in the legend to FIG. 3A was followed. Spleen cells from mice injected with paclitaxel and LM-IL-2K$^b$/SB5b cells followed by the injection of SB5b cells were co-incubated for 5 days with mitomycin C-treated SB5b cells (spleen cell: breast cancer ratio=30:1). At the end of the incubation, $^{51}$Cr-labeled SB5b cells were added and the specific cytotoxic activity was determined at varying E:T ratios in a standard 4 hr $^{51}$Cr-release assay.

*p<0.0005 for the specific release of the isotope from SB5b cells co-incubated with spleen cells from mice injected with paclitaxel, followed by LM-IL-2K$^b$/SB5b cells and SB5b cells [FIG. 4A—column d] relative to the release of isotope from SB5b cells co-incubated with spleen cells from mice injected with paclitaxel and SB5b cells alone [FIG. 4A—column b] or with SB5b cells alone [FIG. 4A—column a]. **p<0.005 for the specific release of isotope from SB5b cells co-incubated with spleen cells from mice injected with LM-IL-2K$^b$/SB5b cells and SB5b cells [FIG. 4A—column c], relative to the release of isotope from SB5b cells co-incubated with spleen cells from untreated mice injected with SB5b cells alone [FIG. 4A—column a] or with spleen cells from mice injected with paclitaxel and SB5b cells alone [FIG. 4A—column b]. Difference in the specific release of isotope from SB5b cells co-incubated with spleen cells from mice injected with paclitaxel and LM-IL-2K$^b$/SB5b cells and SB5b cells [FIG. 4A—column d], relative to the release of isotope from SB5b cells co-incubated with spleen cells from mice injected with LM-IL-2K$^b$/SB5b cells [FIG. 4A—column c], not significant.

In FIG. 4(B), C3H/He mice received single i.p. injection of (2.25 mg/kg) paclitaxel. Two days later, the mice were injected s.c. with 5×10⁶ LM-IL-2K$^b$/SB5b cells. Fourteen days afterward, the mice were injected into the fat pad of the breast with 1×10⁵ SB5b cells. Twelve days later, spleen cells from the mice were co-incubated for 18 hr with SB5b cells (E:T ratio=10:1) before they were analyzed in an ELISPOT-IFN-γ assay [FIG. 4B—column d]. As controls, spleen cells from untreated mice injected with SB5b cells alone [FIG. 4B—column a] or mice injected with paclitaxel followed by SB5b cells co-incubated with SB5b cells [FIG. 4B—column b] were substituted for spleen cells from mice injected with paclitaxel and LM-IL-2K$^b$/SB5b cells [FIG. 4B—column d]. As an additional control, spleen cells from the immunized or non-immunized mice were incubated in medium alone (control groups), *p<0.001 for the difference in number of spots from mice injected with paclitaxel and LM-IL-2K$^b$/SB5b cells [FIG. 4B—column d] and mice in the control groups [FIG. 4B—column a] and [FIG. 4B—column b]. **p<0.001 for the difference in number of spots in the group of mice injected with LM-IL-2K$^b$/SB5b cells followed by the injection of SB5b cells [FIG. 4B—column c] and mice in the control groups [FIG. 4B—columns a] and [b]. Other differences, not significant.

In FIG. 4(C), C3H/He mice (2/group) were injected i.p. with 2.25 mg/kg paclitaxel. Two days later, the mice were injected s.c. with 5×10⁶ LM-IL-2K$^b$/SB5b cells. Sixty-three days afterward, spleen cells from the immunized mice were co-incubated for 5 days with (mitomycin-C-treated) SB5b cells, mAbs for CD8+ or CD4+ cells and low tox rabbit complement (Pel Freeze, Rogers, Ark.) were added to the pooled spleen cell suspensions 1 hr before the cytotoxic activities toward $^{51}$Cr-labeled SB5b cells were determined (E:T=100:1) (FIG. 4C—column c). As controls, the same protocol was followed except that the mice were injected with the vaccine alone [FIG. 4B—column b] or the mice were not injected (FIG. 4B—column a). Values represent means±SD of triplicate determinations, *p<0.05 for the difference between the specific release of isotope in the groups treated with CD8+ mAbs and C and groups treated with CD4+ mAbs and C.

The results (FIG. 4A) indicated that the specific release of isotope from the labeled breast cancer cells was significantly increased, relative to that of the control, untreated group (p<0.005). Analogous results were obtained if the spleen cells were tested in ELISPOT IFN-γ assays (FIG. 4B). The number of spots developing in spleen cell cultures from immunized mice co-incubated with SB5b cells was significantly higher than that of spleen cell cultures from control non-immunized mice (p<0.001). An injection of paclitaxel before immunization had no significant effect upon the cytotoxicity assay or the number of spots developing in spleen cell cultures from mice injected with the vaccine. Antibody inhibition studies indicated that prior treatment of the spleen cell suspensions with CD8+ mAbs and C but not CD4+ mAbs and C significantly (p<0.005) inhibited the anti breast cancer cytotoxicity responses (FIG. 4C). Co-administration of paclitaxel had no significant effect upon either the cytotoxicity response or the number of IFN-γ spots in the ELISPOT assays.

The ELISPOT assays were performed in the following way. Responder (R) T cells from the spleens of C3H/HeJ mice immunized with the transfected cells were added into individual wells (1×10⁶ cells per well in 0.2 ml growth medium) of 96-well ELISPOT IFN-γ plates (B-D Pharmingen, ELISPOT Mouse IFN-gamma Set (Cat #551083)) coated with 100 μl of the capture Ab (5 g/ml in PBS). Stimulator (S) SB5b breast cancer cells were then added at an R:S ratio of 10:1. After incubation for 18 hr at 37°, the cells were removed by washing with PBS-Tween (0.05%). Detection antibodies (2 μg/ml) were then added to each well. The plates were incubated for 2 hrs at RT and the washing steps were repeated.

Afterward, streptavidin-peroxidase (Streptavidin-HRP, 5 g/ml) was added to the individual wells and the plates were washed four times with PBS-Tween and twice with PBS. One hundred μl of aminoethylcarbazole staining solution was added to each well to develop the spots. The reaction was stopped after 4-6 min with deionized water. The spots were counted by computer-assisted image analysis (Immunospot Series 2 analyzer: Cellular Technology Limited, Cleveland, Ohio).

Figure 7:
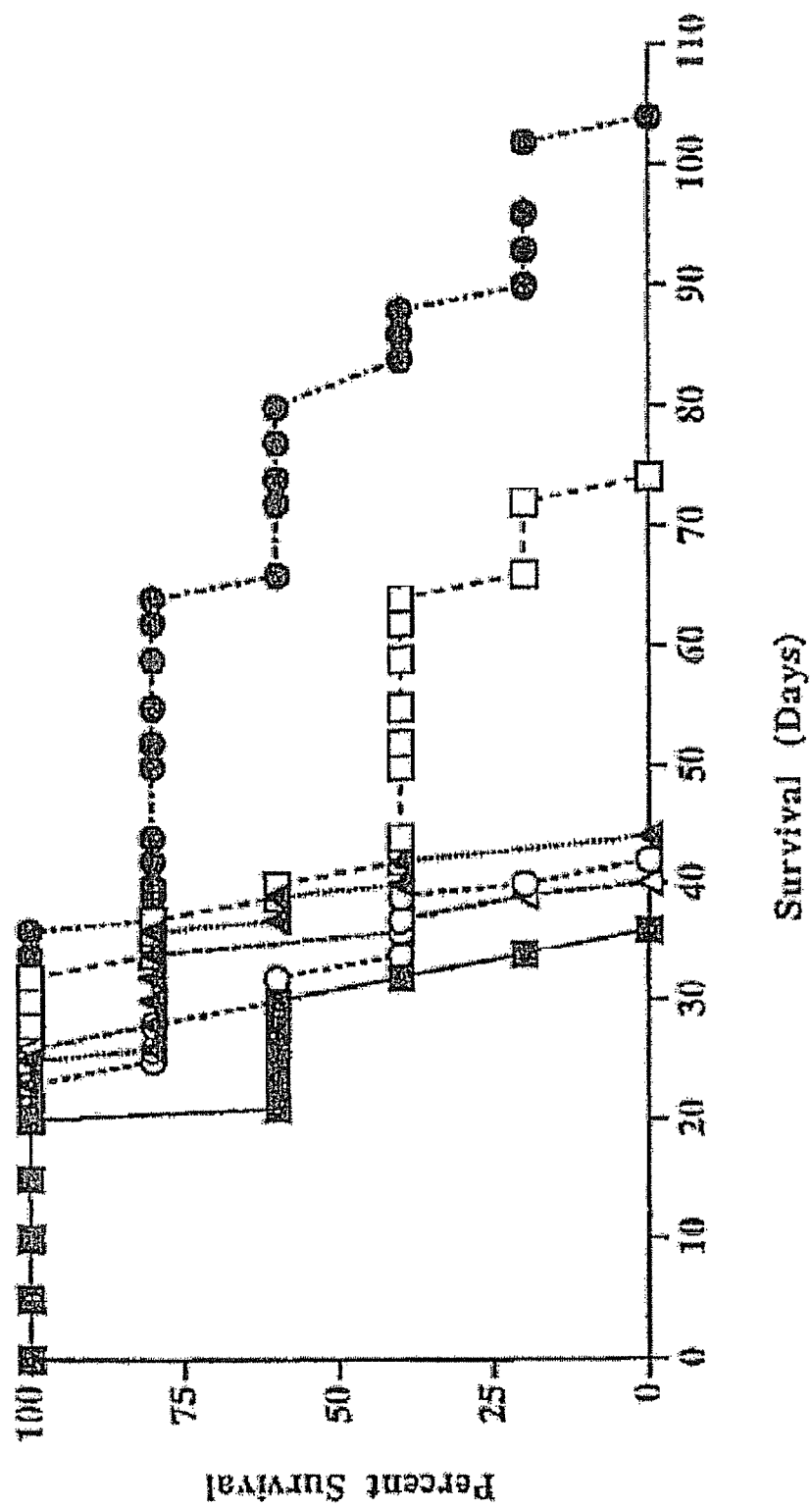
FIG. 7 shows survival statistics for C3H mice injected with SB-1 breast cancer cells (isolated from a breast neoplasm that arose spontaneously in a C3H/He mouse) and fibroblasts transfected with DNA from the same neoplasm (●), SB-1 tumor cells (■), cells modified to secrete IL-2 (Δ), cells modified to secrete IL-2 and to express H-2K$^b$ determinants (○), fibroblasts transfected with DNA from SB 1 cells (▲) and fibroblasts transfected with DNA from EO771 cells (□).

FIG. 7 provides survival statistics for C3H mice injected with SB-1 breast cancer cells. These data are in agreement with data of FIG. 3 discussed above.

Taken together the data presented in this Example show that immunity to the breast cancer was generated in C3H/HeJ mice immunized with a vaccine prepared by transfection of modified fibroblasts with genomic DNA-fragments from the breast cancer cells. Our prior experience (Sun T, Cancer Gene Therapy 1998; 5:110-8; deZoeten E, Gene Therapy 2002; 9:1163-72; de Zoeten E F, J Immunol 1998; 160:2915-22; Cohen E P. Trends in Molecular Medicine 2001; 7:175-8) indicated that tumor immunity failed to develop in mice immunized with nontransfected fibroblasts, or mice immunized with fibroblasts transfected with DNA from a heterologous tumor.

Example 6

Treatment of Breast Cancer with a Combination of Paclitaxel and Genomic DNA-Based Vaccine LM-IL-2K$^b$/SB5b The therapeutic effects of paclitaxel administered in combination with the DNA-based vaccine were investigated in mice with breast neoplasms derived from SB5b cells. Cancers were first established in the fat pad of the breast of C3H/He mice following a single injection of 1×10⁵ SB5b cells. Six days later, when the average tumor was approximately 3 mm, the mice received a single s.c. injection of 2.25 mg/kg paclitaxel. Six days afterward, the mice received the first of three s.c. injections at weekly intervals of 5×10⁶ LM-IL-2Kb/SB5b cells. As controls, the mice were injected into the fat pad with an equivalent number of SB5b breast cancer cells alone, with SB5b cells followed by a single injection of paclitaxel alone or with paclitaxel followed by the vaccine (FIG. 5(A)).

The experiment was terminated 47 days after injection of the breast cancer cells. Mean survival time±standard error (SE) is presented in FIG. 5(A): Mice injected with SB5b cells alone 27±2 days; mice injected with paclitaxel alone, 26±2 days, mice injected with LM-IL2K$^b$/SB5b cells, 27±2 days; mice injected with paclitaxel and LM-IL-2K$^b$/SB5b cells, 42±3 days.

*p<0.01 for the difference in survival of mice receiving the combined therapy and mice in any of the other groups.

Figure 5:
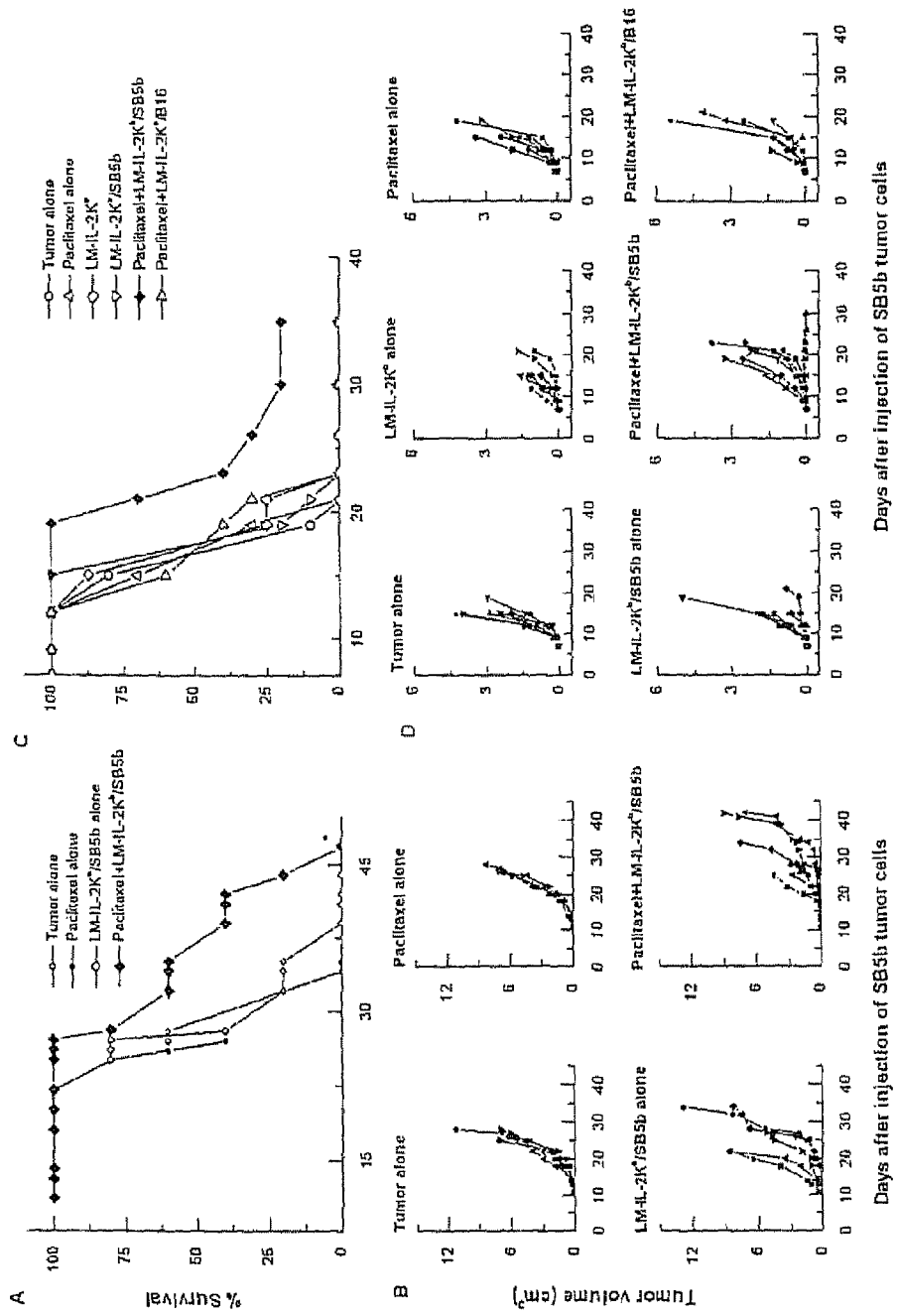
FIG. 5 depicts survival of C3H/He mice with breast cancer receiving combined therapy with paclitaxel and LM-IL-2K$^b$/SB5b cells.

In FIG. 5(B), the same protocol as described in (FIG. 5A) was followed. Tumor volumes were determined by the equation 0.5 l×w². Length and width were determined with a dial caliper.

In FIG. 5(C), C3H/He mice (10/group) were injected with SB5b cells followed by paclitaxel and LM-IL-2K$^b$/SB5b cells, according to the schedule described in (A). Additional controls included mice receiving paclitaxel alone, mice injected with (non transfected) LM-IL-2K$^b$ cells, mice injected with LM-IL2K$^b$/SB5b cells alone, and mice injected with paclitaxel and LM-IL2K$^b$/B16 cells.

*p<0.01 for the difference in survival of mice receiving the combined therapy and mice in any of the other groups.

In FIG. 5(D), the same protocol as described in (C) was followed. Tumor volumes were determined by the equation 0.5 l×w$^2$. Length and width were determined with a dial caliper.

As indicated (FIG. 5A), mice with established breast neoplasms that received the combination of paclitaxel followed by immunization with the transfected fibroblasts survived significantly (p<0.01) longer than mice in any of the other groups. The survival of mice with breast cancer treated with paclitaxel alone, or by immunotherapy alone, was not significantly different than that of untreated mice with breast cancer.

To determine if the therapeutic effects of the vaccine were specific, the experiment was repeated to include treatment of mice with breast cancer with a vaccine prepared by transfer of DNA-fragments from B16 melanoma cells into the modified fibroblasts (LM-IL-2Kb/B16 cells). As indicated (FIG. 5C), the survival of mice with breast cancer treated with a combination of paclitaxel and LM-IL-2Kb/B16 cells was not significantly different than that of untreated mice or mice treated with paclitaxel alone. Immunization with non-transfected modified fibroblasts (LM-IL-2Kb cells) had no significant therapeutic effect. Measurements of tumor growth in mice with breast cancer treated by the combined therapy were consistent with therapeutic outcome. Tumor growth was delayed in mice receiving the combined therapy, relative to that of mice in any of the other groups (FIGS. 5B and 5D).

The results of two independent spleen cell assays designed to detect the presence of CTLs reactive with SB5b cells were consistent with the enhanced survival of mice receiving the combined therapy. Mice with breast cancer were treated according to the same protocol with paclitaxel, followed by immunization with LM-IL-2Kb/SB5b cells. Seven days after the last injection of the vaccine, spleen cells from the immunized, tumor-bearing mice were tested in $^{51}$Cr-release cytotoxicity assays (FIG. 6(A)).

C3H/He mice (2 per group) were injected i.p. with 2.25 mg/kg paclitaxel. Six days later, the mice received the first of two s.c. injections at weekly intervals of 5×10$^6$ LM-IL-2K$^b$/SB5b cells. One week after the second injection, aliquots of a suspension of spleen cells from the immunized mice were tested in a standard $^{51}$Cr-release assay for the presence of CTLs reactive with SB5b cells at three different E:T ratios. As controls, the same protocol was followed except that the mice were injected with SB5b cells alone, with SB5b cells and paclitaxel alone, with SB5b cells and (non transfected) LM-IL-2K$^b$ cells, with SB5b cells and LM-IL-2K$^b$/SB5b cells, or with paclitaxel and LM-IL-2K$^b$/B16 cells. P<0.001 for the specific release of isotope in the group receiving the combined therapy and that of any of the other groups.

Figure 6:
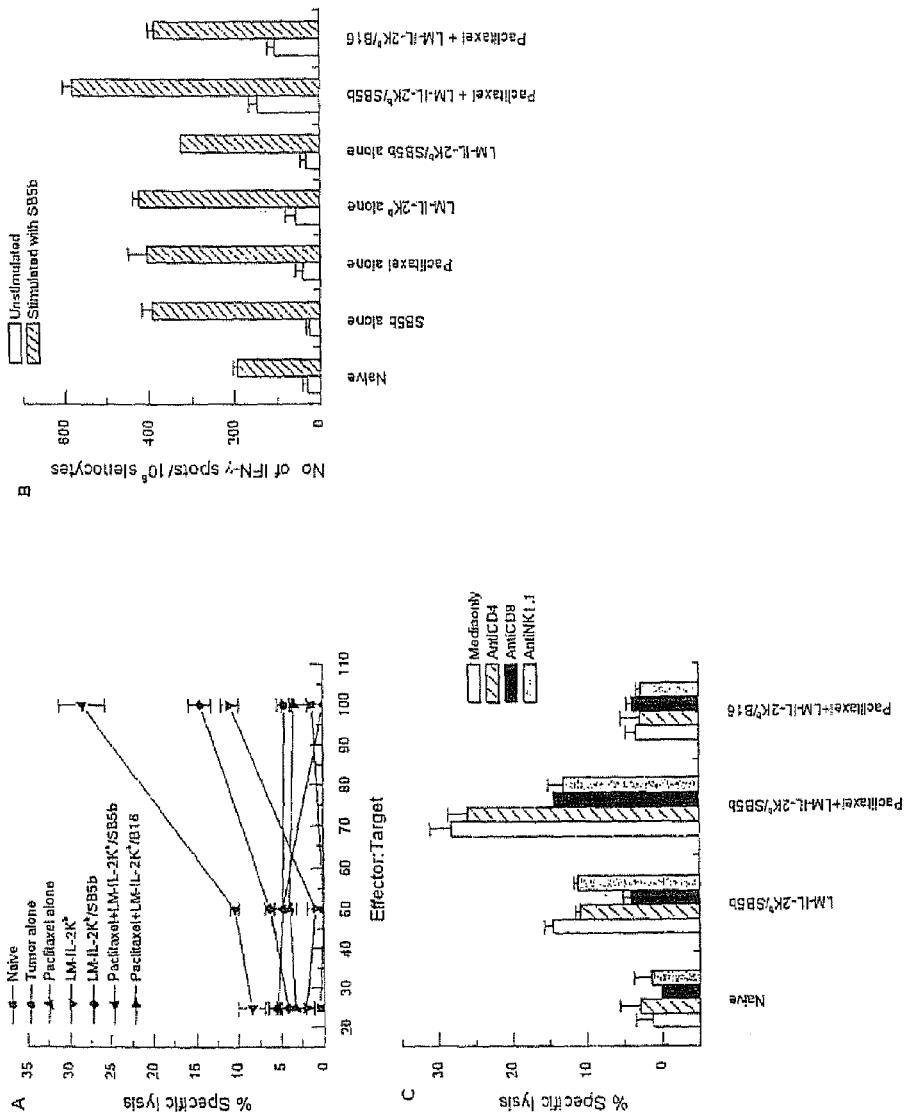
FIG. 6 depicts immunity to breast cancer in C3H/He mice receiving combined therapy with paclitaxel and LM-IL-2K$^b$/SB5b cells.

FIG. 6(B) shows results of ELISPOT IFN-γ assays in which C3H/He mice (2 per group) were injected i.p. with 2.25 mg/kg paclitaxel. Two days later, the mice received the first of two s.c. injections at weekly intervals of 5×10$^6$ LM-IL-2K$^b$/SB5b cells. One week after the second injection, aliquots of a suspension of spleen cells from the immunized mice were divided into two populations. One population was co-incubated for 18 hr with SB5b cells (ET ratio=10:1). One population was incubated for the same period without SB5b cells. At the end of the incubation, the cells were analyzed by ELISPOT IFN-γ assays. As controls, the same protocol was followed except that the mice were injected with an equivalent amount of paclitaxel alone, with equivalent numbers of (non transfected) LM-IL-2K$^b$ cells alone, with LM-IL-2K$^b$/SB5b cells alone, with paclitaxel and LM-IL-2K$^b$/B16 cells alone or the mice were injected with SB5b cells alone. *p<0.01 for the difference in the number of spots in the group injected with paclitaxel and LM-IL-2K$^b$/SB5b cells co-incubated with SB5b cells and in any of the other groups.

FIG. 6(C) shows results of Cr-release cytotoxicity assays in the presence of CD4+, CD8+ or NK1.1 antibodies. The same protocol described in FIG. 6A was followed except that antibodies for CD4+, CD8+ or NK1.1 determinants and C were added before the cytotoxicity assays were performed. P<0.001 for the differences in percent specific lysis of SB5b cells in the presence and absence of CD8+ and NK1.1 antibodies in the group injected with paclitaxel and LM-IL2K$^b$/SB5b cells.

As shown in FIG. 6A, the percent specific lysis from the group of mice receiving the combined therapy was significantly (p<0.001) higher than that of any of the other groups including spleen cells from mice immunized with the vaccine alone or mice immunized with paclitaxel and LM-IL-2Kb/B16 cells (p<0.001). Analogous results were obtained in ELISPOT IFN-γ assays. The highest number of spots was obtained if the spleen cells were from mice receiving the combined therapy (FIG. 6B). To determine the classes of cells mediating resistance to the tumor, mAbs for NK1.1, CD8+ or CD4+ determinants were added to the spleen cell suspensions before the 51Cr-release cytotoxicity assays were performed. As shown in FIG. 6C, the greatest inhibitory responses were in the groups treated with NK1.1, CD8+ mAbs.

In conclusion, data presented in Example 6 show that combing the administration of paclitaxel with immunotherapy with a unique DNA-based vaccine successfully prolonged the survival of mice with breast cancer.

Example 7

Isolation of Dendritic Cells

Peripheral blood mononuclear cells (PBMC) were obtained from a donor and were separated from other blood components by Ficoll separation. PBMCs were then suspended in AIM-V medium (10$^7$/ml) and incubated for 1 h at 37° C. in T75 flasks (Falcon/Becton Dickinson). Plastic-adherent cells were then cultured in AIM-V medium supplemented with 1,000 units/ml of IL-4 and 1,000 units/ml of granulocyte macrophage colony-stimulating factor for 6 days at 37° C./5% CO$_2$ in air. The DCs were then harvested on day 6 in cold Hanks' solution (Life Technologies), washed, and resuspended at a concentration of 2×10$^6$ cells per ml in AIM-V medium.

Example 8

Ex Vivo Anti-Tumor Response of Human Dc Recipient Cells

PCI-13/IL-2 cells, a transformed human cell line modified to secrete IL-2 were transfected in a manner similar to Example 4 with genomic DNA obtained from, an HLA-A2$^+$ squamous carcinoma cell line. The transfected PCI-13/IL-2 cells were subjected to UVB-induced apoptosis then fed to dendritic cells isolated from an HLA-A2$^+$ donor, which was then incubated with peripheral blood mononuclear cells from the same donor as the dendritic cells. Three T-cell lines were generated in 14-day cultures (T1, T2 and T3).

Each T-cell line was stimulated with a range of tumor cell targets in ELISPOT assays, as described in (Asai et al., Clin. Diagn. Lab. Immunol. 7: 145-154, 2000). Briefly, responder (R) T cells ($1\times10^3$ to $5\times10^3$) were plated in 96-well plates with nitrocellulose membrane inserts (Millipore) coated with 50 μl of the capture antibody (10 μg/ml in 1×PBS, clone MABI-DIK; MABTECH, Stockholm), Stimulator (S) cells were then added at the R:S ratio of 20:1. Stimulator cells were transformed PCI13/IL-2 cells, PCI-1 cells, OSC-19 cells and HR(HLA-A2$^+$ gastric carcinoma).

After a 24-h incubation, the cells were removed by washing the plates 6 times with 0.05% (wt/vol) Tween-20 in PBS (Fisher Scientific). The detection antibody (2 μg/ml, clone Mab7-B6-1; MABTECH) was added to each well. The plates were incubated for 2 h and the washing steps were repeated. After a 1-h incubation with avidin-peroxidase (Vectastain Elite Standard ABC kit; Vector Laboratories), the plates were washed. Aliquots (100 μl) of aminoethylcarbazole staining solution (Sigma) were added to each well to develop the spots. The reaction was stopped after 4-6 min by washing with water. The spots were counted with computer-assisted image analysis (ELISPOT 4.14.3, Zeiss).

Figure 8:
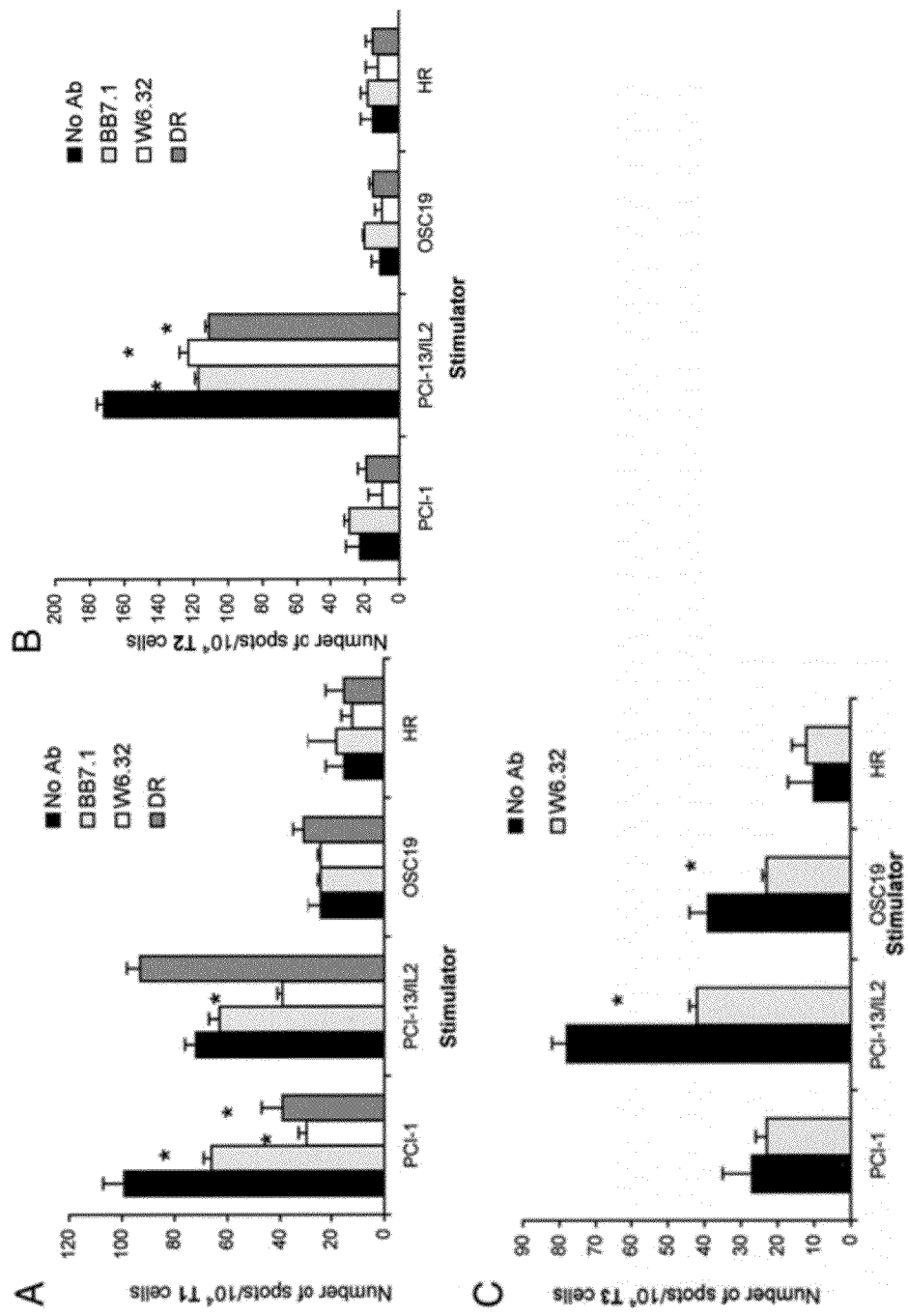
FIG. 8 shows an ex vivo anti-tumor response in three different human T cell lines.
Figure 9:
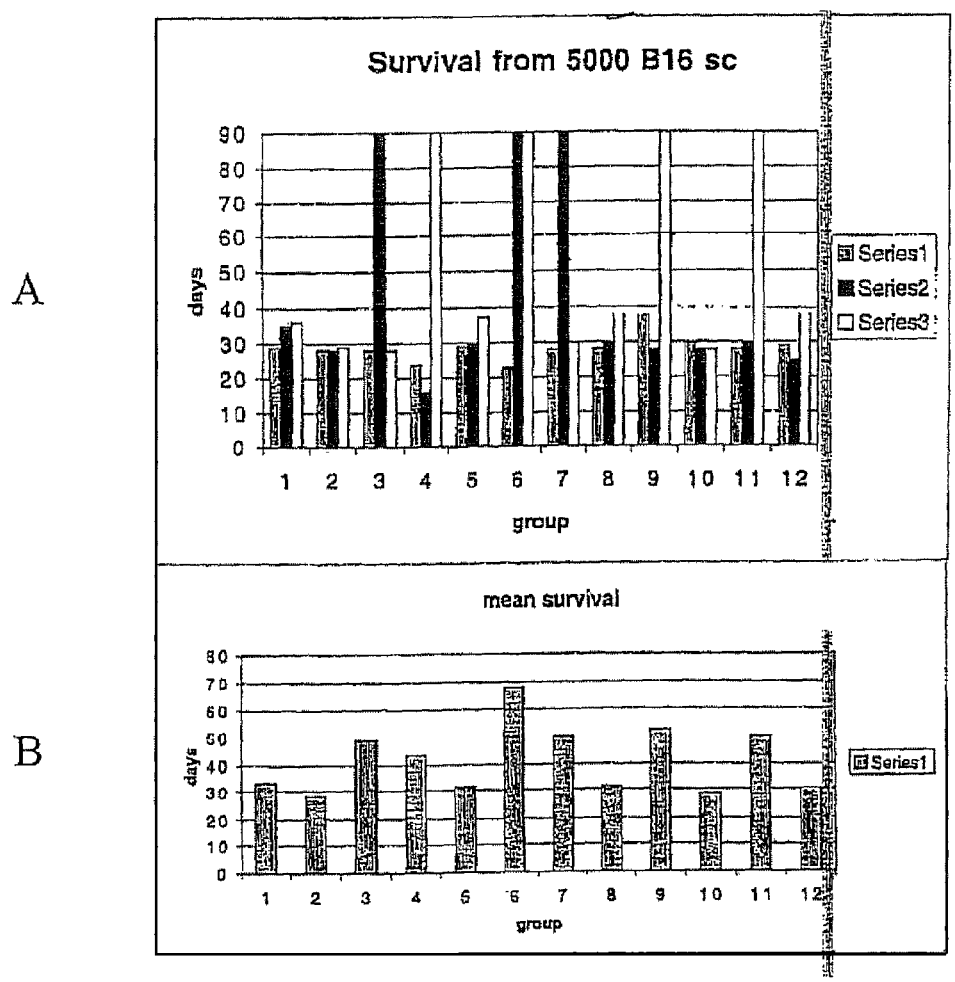
FIG. 9 shows survival (Panel A) and mean survival (Panel B) of mice immunized with an anti-melanoma vaccine.

FIG. 8A shows that T1 cells responded to PCI-1, the DNA donor, and to PCI-13/IL-2 cells. Each of these responses was inhibited ($p<0.01$; see asterisks) by anti-MHC Abs (anti-HLA-A2 antibodies), FIG. 8B shows that T2 cells responded only to PCI-13/IL-2 cells, with the response being blocked by anti-HLA-2 antibodies. FIG. 8C shows that T3 cells recognized OSC-19, the DNA donor, and PCI-13/IL-2 cells, with each of these responses being inhibited by anti-class I MHC Abs (anti-HLA-A2 antibodies). The stimulated T cells recognize the tumor cells from which the DNA was obtained to transfect the recipient cells. This shows that tumor epitopes encoded in tumor-DNA were expressed by the recipient cells and were able to induce tumor-specific T cells.

Example 9

Expansion and Enrichment of Immunogenic Recipient Cells Expressing Tumor Associated Antigens LM fibroblasts modified to secrete IL-2 and to express H-2K$^b$ determinants (as an allo stimulus) were transfected with genomic DNA from KMN205 cells, a squamous carcinoma cell line. The transfected cells were divided into ten pools, each pool consisting of $1\times10^3$ cells. The cell number in each pool was allowed to increase and cells from each pool were then tested for their capacity to induce an anti-tumor immune response.

C3H mice (syngeneic with KLN205 cells) were injected s.c. two times at weekly intervals with $5\times10^6$ transfected cells from each pool. Six days after the last injection, T cells from the spleens of the immunized mice were tested in a standard $^{51}$Cr-release assay for cytolytic activity toward KLN205 cells. The anti-tumor activity of the cells from pool number 9 greatly exceeded those of the other pools. Furthermore, cells from pool number 6 were without significant anti-tumor activity. These results indicate that dilution of the immunogenic cells may provide pools of cells of differing immunogenic properties.

Example 10

Production of Immunogenic Dendritic Cells from Mice

Dendritic cells, which are to be used as recipient cells, are generated from C57BL/6 mice, as described by Sallusto and Lanzavecchia (Sallusto & Lanzavecchia, J. Exp. Med. 179: 1109-1118, 1994) with modification. Briefly, PBMC isolated from mice suspended in AIM-V medium are incubated for 1 h at 37° C. in T75 flasks (Falcon/Becton Dickinson). Plastic-adherent cells are cultured in AIM-V medium supplemented with 1,000 units/ml of IL-4 and 1,000 units/ml of granulocyte macrophage colony-stimulating factor for 6 days at 37° C./5% CO2 in air.

The dendritic cells are then transfected with DNA derived from a syngeneic breast neoplasm arising in MTag mice, in a manner similar to that described in Example 8. MTag mice are transgenic for the polyomavirus middle T antigen under control of the mouse mammary tumor virus promoter/enhancer. The mice develop breast cancer by 12 weeks of age. The tumors develop in the epithelium of the breast and metastasize to regional lymph nodes, among other organs and tissues.

The transfected dendritic cells are then grown in culture in the presence of GM-CSF, CD40L and LPS to stimulate the dendritic cells to undergo maturation, as indicated by the increase in expression of class I and II MHC-determinants and co-stimulatory molecules. The functional status of the transfected dendritic cells is determined by their capacity to induce allogeneic T cell proliferation in mixed leukocyte reactions, in a manner similar to that described in Example 8.

Example 11

Testing of Immunogenic Dendritic Cells from Mice

The ability of the transfected dendritic cells to act as a vaccine is determined by measuring the time to first appearance of tumor and time of survival of immunized mice injected with varying numbers (range=$1\times10^3$ to $5\times10^5$) of the same breast cancer cells that provided the donor DNA. These results are compared to those of syngeneic mice injected with an equivalent number of breast cancer cells alone. Additional controls include mice injected with dendritic cells transfected with DNA from normal (non-neoplastic) liver cells, with dendritic cells transfected with DNA from an unrelated tumor (melanoma) or with non-DNA-transfected dendritic cells.

Example 12

Determination of the Proportion of Transgenic Cells that Express Tumor Associated Antigens In order to define the proportion of immunogenic dendritic cells from that express tumor associated antigens, limiting dilution assays are performed in combination with the application of Poisson statistics. Varying numbers (range=$5\times10^3$ to $1\times10^5$) of transfected dendritic cells are distributed to 20 replicate wells at each cell number. After further cell proliferation, naive C57BL/6 mice are immunized, with cells derived from individual wells. Three mice receive three injections of $5\times10^6$ cells at weekly intervals from each pool. One week after the last injection, the mice are challenged with an s.c. injection of $5\times10^3$ the same breast cancer cells that provided the donor DNA. Tumor growth and rates of survival of mice in each treatment group are determined. Inhibition of tumor growth is taken as an indication that the original well contained cells that expressed tumor associated antigen characteristic of breast cancer cells. Poisson statistics is used to determine the proportion of the transfected cells that induced immunity to the tumor. The results indicate that a vaccine enriched for transfected dendritic cells that express tumor associated antigens is likely to be more therapeutically effective than non-enriched cells.

Example 13

Enrichment of Immunogenic Dendritic Cells from Mice Expressing Tumor Associated Antigens In order to enrich dendritic recipient cells that express tumor associated antigens, dendritic cells transfected are divided into ten pools. Each of the ten pools is added to culture medium AIM-V to expand the cells of each pool. Aliquots from each pool are use to immunize C57BL/6 mice three times at weekly intervals. Spleen cells are then isolated one week later from the immunized mice and incubated for 24 hours with the donor breast cancer cells. The samples are then tested for T cell immunity to the tumor cells using ELISPOT, in a manner similar to that described in Example 8. Those pools leading to T cell immunity are then divided into ten new pools and the steps of expansion, immunization and T cell immunity testing are repeated.

Example 14

Identification of Genes Encoding Tumor Associated Antigens

Clonal immunogenic recipient cells are produced by repeated serial dilutions. Differentially expressed genes encoding tumor associated genes are identified by using an Affymetrix GeneChip Murine Genome U74 Set, which is a three Gene Chip® probe array capable of interrogating approximately 36,000 full-length mouse genes and EST clusters from the UniGene database.

RNA is isolation and purified from transfected and non-transfected recipient cells using the Rneasy Mini Kit. Biotin-labeled cRNA probes are prepared using the standard GeneChip® eukaryotic target labeling protocol (Affymetrix, Santa Clara, Calif.). The biotin-labeled cRNA probes generated from transfected and non-transfected recipient cells are then hybridized to separate oligonucleotide arrays, followed by binding to streptavidin-conjugated fluorescent marker. Detection of bound probe is achieved following laser excitation of the fluorescent marker and scanning of the resultant emission spectra using a scanning confocal laser microscope. The relative signal is measured for the transfected recipient cells at each oligomer (representing a single gene), and compared to the normalized signal obtained with a labeled cRNA from the non-transfected recipient cells.

Example 15

Identification of Expressed Tumor Associated Antigens

Figure 16:
FIG. 16 provides the size of DNA transfected into the modified fibroblasts.

We prepared cDNA expression libraries from SB5b cells, an Aden carcinoma of the breast that arose spontaneously in a C3H/He mouse in our animal colony. The libraries were constructed with a Lambda Zap vector, using a cDNA library kit (Stratagene). In brief, cDNAs greater than 0.5 kb were selected by size fractionation via gel filtration and directionally cloned into a pBK-CMV vector with an EcoRI restriction site on the 5' end and an XhoI site on the 3' end. The cDNA expression libraries yielded approximately $4\times10^5$ pfu/ug DNA with an individual cDNA insert. The size the cDNA transfected into the modified fibroblasts was between 0.5-7.0 kb (FIG. 16).

The library was co transfected into LM cells, a fibroblast cell line of C3H/He mouse origin, along with pHyg, a plasmid specifying resistance to hygromycin, used for selection (Ratio of cDNA:pHyg=10:1). After selection in medium containing sufficient quantities of hygromycin to kill one hundred percent of non-transfected cells, the surviving colonies (at least $2\times10^4$) were pooled and maintained as a cell line for use in the experiments. To augment the recipient cells' nonspecific immunogenic properties, the fibroblasts were modified before DNA-transfer to secrete IL-2 and to express allogeneic MHC class I-determinants ($H-2K^b$).

Since only a small proportion of the transfected cell population would be expected to have incorporated genes specifying TAA, we devised a new strategy to enrich the population for TAA-positive cells. We accomplished this by dividing the transfected cell-population into small pools (we used 96 well plates), and then expanding the cell number from each pool in vitro. We reasoned that if the starting inoculums were small ($1\times10^3$ cells), then the number of cells in each of the individual pools that expressed TAA would not be the same. After allowing the cell number to increase, and maintaining an aliquot of the expanded cell-suspension frozen/viable (for later use), cells from the expanded individual pools could then be tested in syngeneic C3H/He mice for their immunogenic properties against breast cancer. In this way, pools that induced breast cancer immunity to the greatest extent (immuno$^{high}$) could be identified and the frozen cells from that pool could be reestablished in culture. Immuno$^{high}$ cells would indicate the presence of a higher number of cells in the initial inoculum that expressed TAA. Further rounds of distribution of cells from the immuno$^{high}$ pools, (and for comparison, with pools that stimulated immunity to the least extent, immuno$^{low}$ pools) and the identification of pools that stimulated immunity to the greatest extent would lead to a progressive increase in the proportion of cells that expressed TAA. Our preliminary data, described below, support the validity of this approach. After sufficient rounds of enrichment, by comparing microarrays from immuno$^{high}$ and immuno$^{low}$ pools, candidate genes specifying breast cancer antigens can be identified. Cloned candidate genes can then be inserted into an expression vector and introduced into the fibroblast cell line. Verification of the immunogenic properties of the candidate gene can be accomplished by the induction of a therapeutic anti breast cancer immune response in immunized syngeneic mice susceptible to the tumor.

Figure 17:
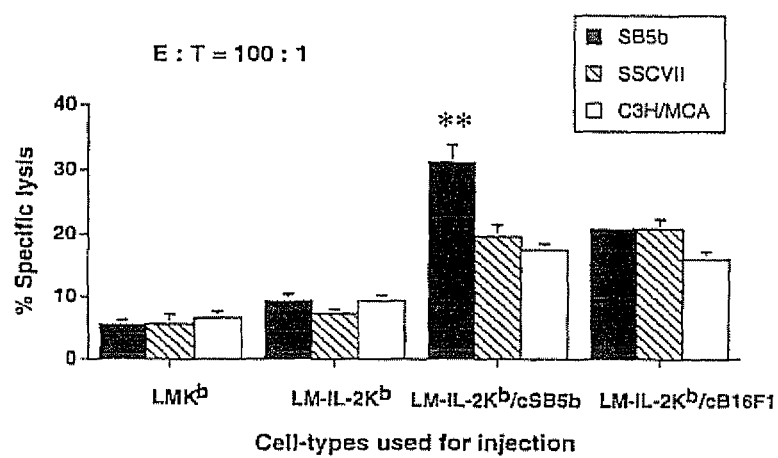
FIG. 17. C3H/He mice were injected s.c. three times at weekly intervals with 5×10$^6$ modified LM fibroblasts co-transfected with a cDNA expression library from SB5b cells (LM-IL-2K$^b$/cSB5b).

The first step was to determine the specificity of the immune response in C3H/He mice immunized with modified fibroblasts transfected with a cDNA library from breast cancer cells (SB5b). The results are presented in FIG. 17.

As additional controls, the same protocol was followed except that the mice were immunized with non transfected modified fibroblasts ($LMK^b$), with IL-2-secreting non transfected fibroblasts ($LM-IL-2K^b$), or with $LM-IL-2K^b$ cells transfected with a cDNA expression library from B16F1 melanoma cells ($LM-IL-2K^b/cB16F1$), a non cross reactive neoplasm. P<0.01 for differences in specific isotope release from SB5b cells in mice immunized with $LM-IL-2K^b$/SB5b cells versus any of the other groups. The results shown in FIG. 17 indicate that the anti-tumor immune response in mice immunized with $LM-IL-2K^b$/cSB5b was specific for SB5b cells.

Mice immunized with a vaccine prepared by cDNA-transfected cells from B16F1 melanoma failed to develop immunity to the breast cancer cells.

Figure 18:
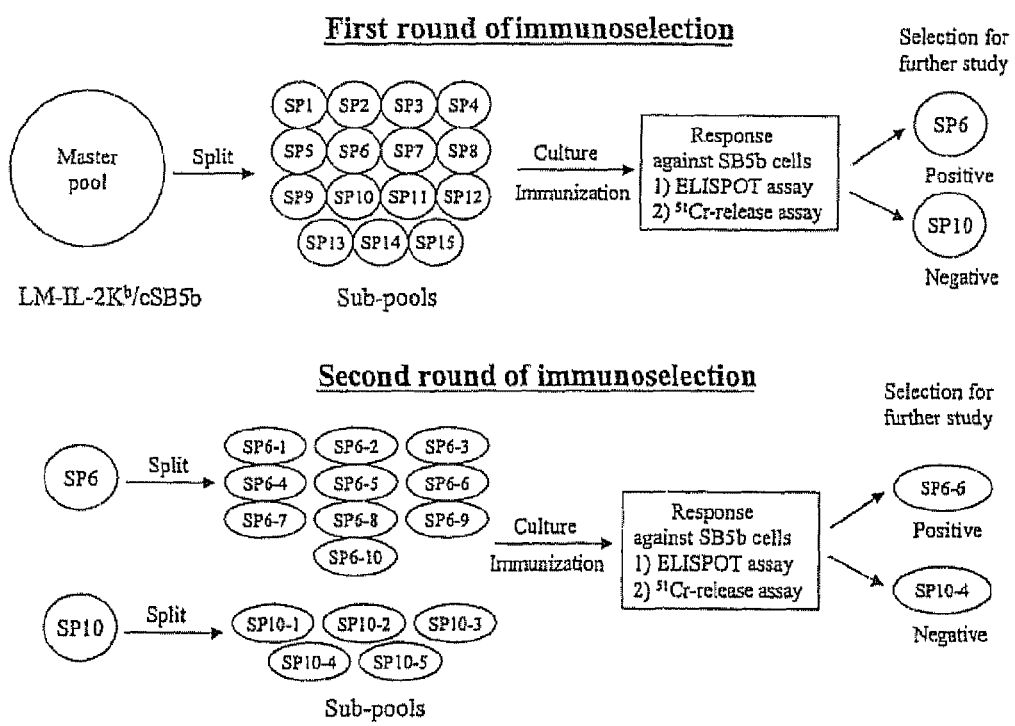
FIG. 18. The Master Pool of transfected cells (nonselected LM-IL-2K$^b$/cSB5b cells) was divided into fifteen subpools. Each subpool contained 1000 cells as the starting inoculum. The number of cells in the pools was expanded and a portion was maintained frozen/viable for later use. The remaining portions from each individual pools were used to immunize C3H/He mice. After immunization, spleen cells were tested by both ELISPOT and $^{51}$Cr-release cytotoxicity assays for reactivity against the SB5b breast cancer cells.

We next identified pools of transfected cells that stimulated immunity to SB5b breast cancer cells to the greatest (immuno$^{high}$), and least (immuno$^{low}$) extent. The schema is presented in FIG. 18

Figure 19:
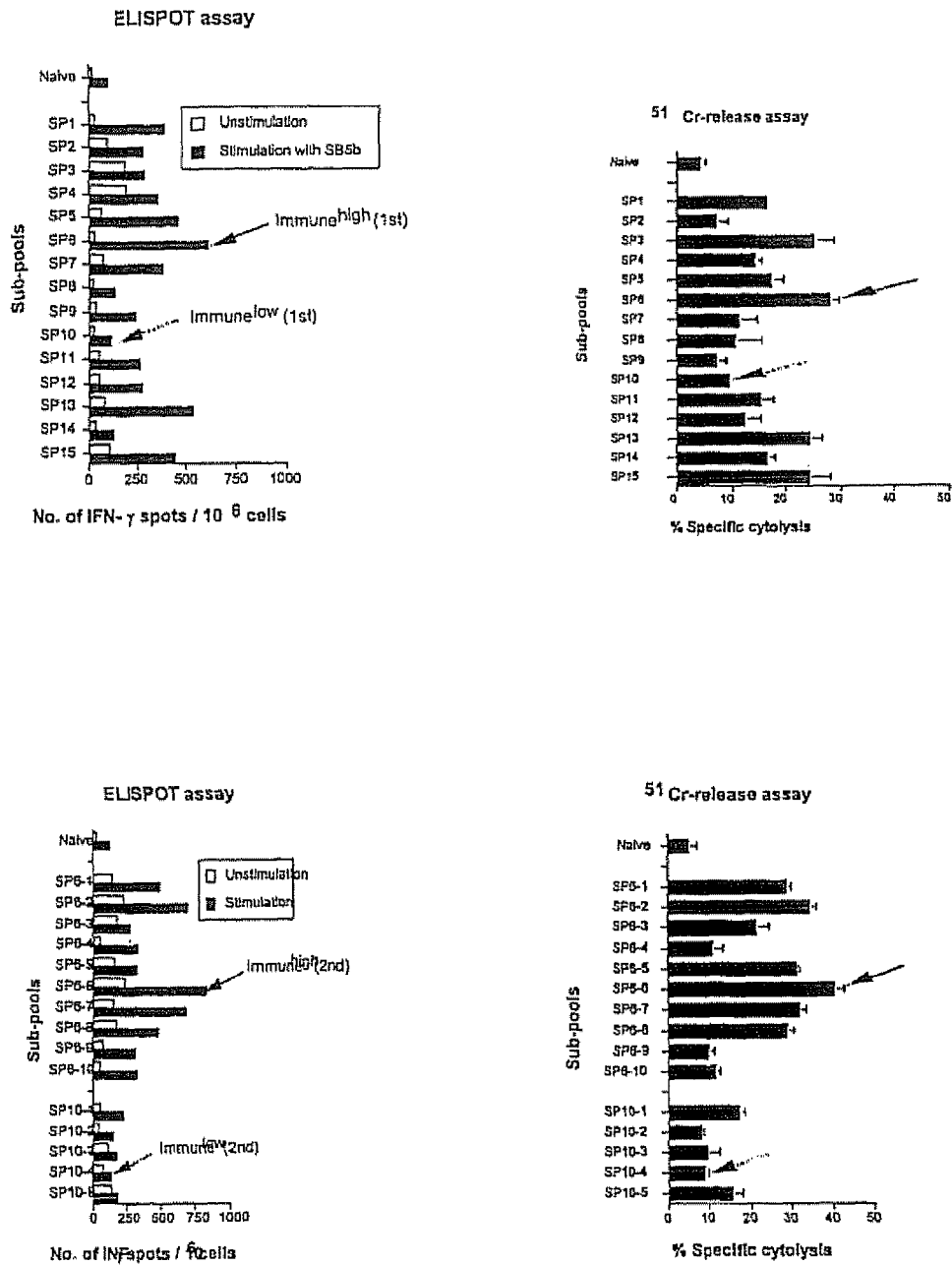
FIG. 19. Immunity to SB5b cells in mice immunized with cells from subpool (SP) 6 exceeded that of mice immunized with cells from any of the other pools, as determined by both ELISPOT and $^{51}$Cr-release cytotoxicity assays.

As indicated (FIG. 19, upper portion) immunity to SB5b cells in mice immunized with cells from subpool (SP) 6 exceeded that of mice immunized with cells from any of the other pools, as determined by both ELISPOT and $^{51}$Cr-release cytotoxicity assays. Subpool 6 was designated immuno$^{high}$. Cells from pool 10 stimulated immunity to SB5b cells to the least extent. It was designated immuno$^{low}$. Frozen/viable cells from each of these pools were recovered. Small aliquots ($1 \times 10^3$) were distributed in individual wells of a 96 well plate, and the procedure was repeated for a second round of immunoselection.

The results (FIG. 19, lower portion) indicate that by the second round of selection, the cytotoxic activity toward SB5b cells in mice immunized with cells from the immuno$^{high}$ pools was significantly (P<0.001) greater than that of cells from the immuno$^{low}$ pools.

Figure 20:
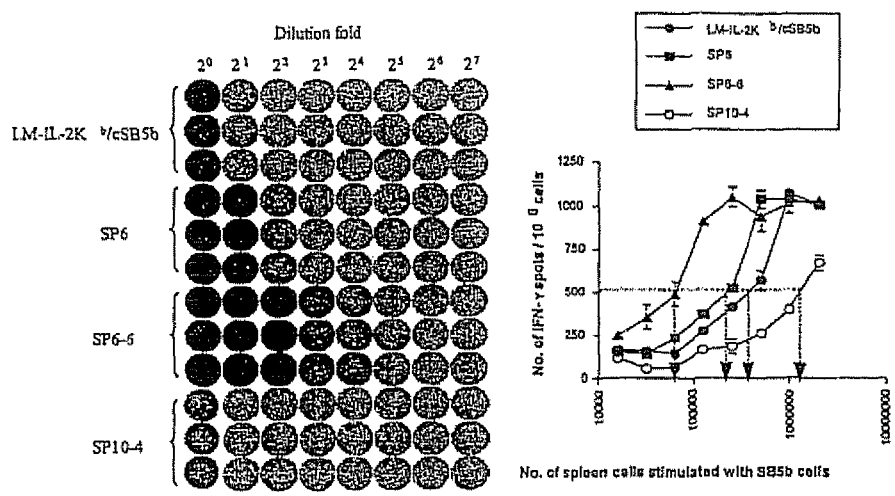
FIG. 20. Representative Elispot assay derived from the spleen of mice immunized with immuno$^{high}$ (SP6-6) cells from the second round of selection and immuno$^{low}$ (SP10-4) pools in comparison with cells from the non-selected Master Pool (LM-IL-2Kb/cSB5b).

A representative Elispot assay derived from the spleen cells of mice immunized with immuno$^{high}$ (SP6-6) cells from the second round of selection and immuno$^{low}$ (SP 10-4) pools, and, for comparison with cells from the non selected Master Pool (LM-IL-2Kb/cSB5b) is presented in the FIG. 20. Specifically, C3H/He mice were injected s.c. with $5 \times 10^6$ cells from the immuno$^{high}$ pool SP 6-6. One week after the last injection, spleen cells from the immunized mice were serially ten fold diluted and then tested in an ELISPOT assay for the presence of spleen cells reactive with SB5b cells. As control, the same procedure was followed except that cells from the immuno$^{low}$ pool SP 10-4 or from the non-selected Master Pool were substituted for cells from the immuno$^{high}$ pool. The right hand figure indicates the number of spleen cells from mice immunized with cells from the immuno$^{high}$ the immuno$^{low}$ or the Master Pool required to achieve one-half the maximum number of spots.

ELISPOT assays were performed as follows: Responder (R) T-cells ($1 \times 10^3$ to $5 \times 10^3$) from spleen cell cultures incubated 7 to 10 days with the transfected cells are plated in wells of 96-well plates with nitrocellulose membrane inserts (Millipore, Bedford, Mass.) coated with 50 µL of the capture antibody (10 µg/ml in 1×PBS; clone MABI-DIK; (Mabtech, Nacka, Sweden). Stimulator (S) cells (SB5b cells) are then added at the R:S ratio of 20:1. After 24 hr incubation, cells are removed by washing. The detection antibody (2 µg/ml) is added to each well. The plates are incubated for 2 hrs and the washing steps are repeated. Following 1 hr incubation with avidin-peroxidase, the plates are washed. Aliquots of (100 µL) of aminoethylcarbazole staining solution are added to each well to develop the spots. The reaction is stopped after 4-6 min with water. The spots are counted using computer-assisted image analysis (Zeiss ELISPOT 4.14.3. Jena, Germany). When experimental values are significantly different from the mean number of spots against non-pulsed cells (background values), as determined by a two-tailed Wilcoxon's rank sum test, the background values are subtracted from the experimental values. The coefficient of variation (CV) for the assay has been determined to be <15% (n=50). This strategy is expected to enhance the therapeutic benefits of the vaccine by enriching the cell-population for transfected cells that express TAA that characterize the breast cancer. The studies will further optimize the therapeutic effects in mice with established breast neoplasms.

The immunogenic properties of cells from the immuno$^{high}$ and immuno$^{low}$ pools were then tested for their immunoprotective properties in C3H/He mice, highly susceptible to the growth of the breast cancer cells. The results are presented in FIG. 21. Specifically, Cells from the immuno$^{high}$ and immuno$^{low}$ pools were tested for their immunogenic properties in C3H/He mice, susceptible to the growth of the breast cancer cells. The mice were injected s.c. three times at weekly intervals with $5 \times 10^6$ cells. One week afterward, the mice were injected into the fat pad of the breast with $1 \times 10^5$ SB5b breast cancer cells.

Figure 21:
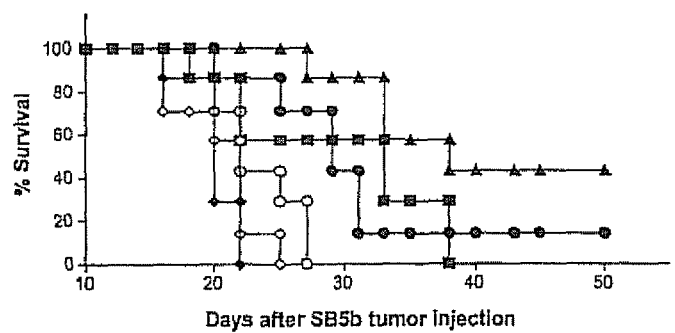
FIG. 21. Immunity to breast cancer in mice immunized with immuno$^{high}$ and immuno$^{low}$ sub-pools of transfected cells. The mice were injected s.c. three times at weekly intervals with 5×10$^6$ cells. One week afterward, the mice were injected into the fat pad of the breast with 1×10$^5$ SB5b breast cancer cells.

The results shown in FIG. 21 indicate that the survival of mice with breast cancer immunized with the immuno$^{high}$ pool (SP6-6) (from the second round) exceeded that of mice immunized with cells from any of the other pools including mice immunized with cells from the master pool LM-IL-2K$^b$/SB5b. (P<0.01). Mice with breast cancer immunized with cells from the immuno$^{low}$ pool (SP10-4) or with cells transfected with a cDNA library from B16F1 melanoma cells (LM-IL-2K$^b$/B16F1) failed to survive significantly longer than tumor-bearing mice injected with saline.

Example 16

Figure 22:
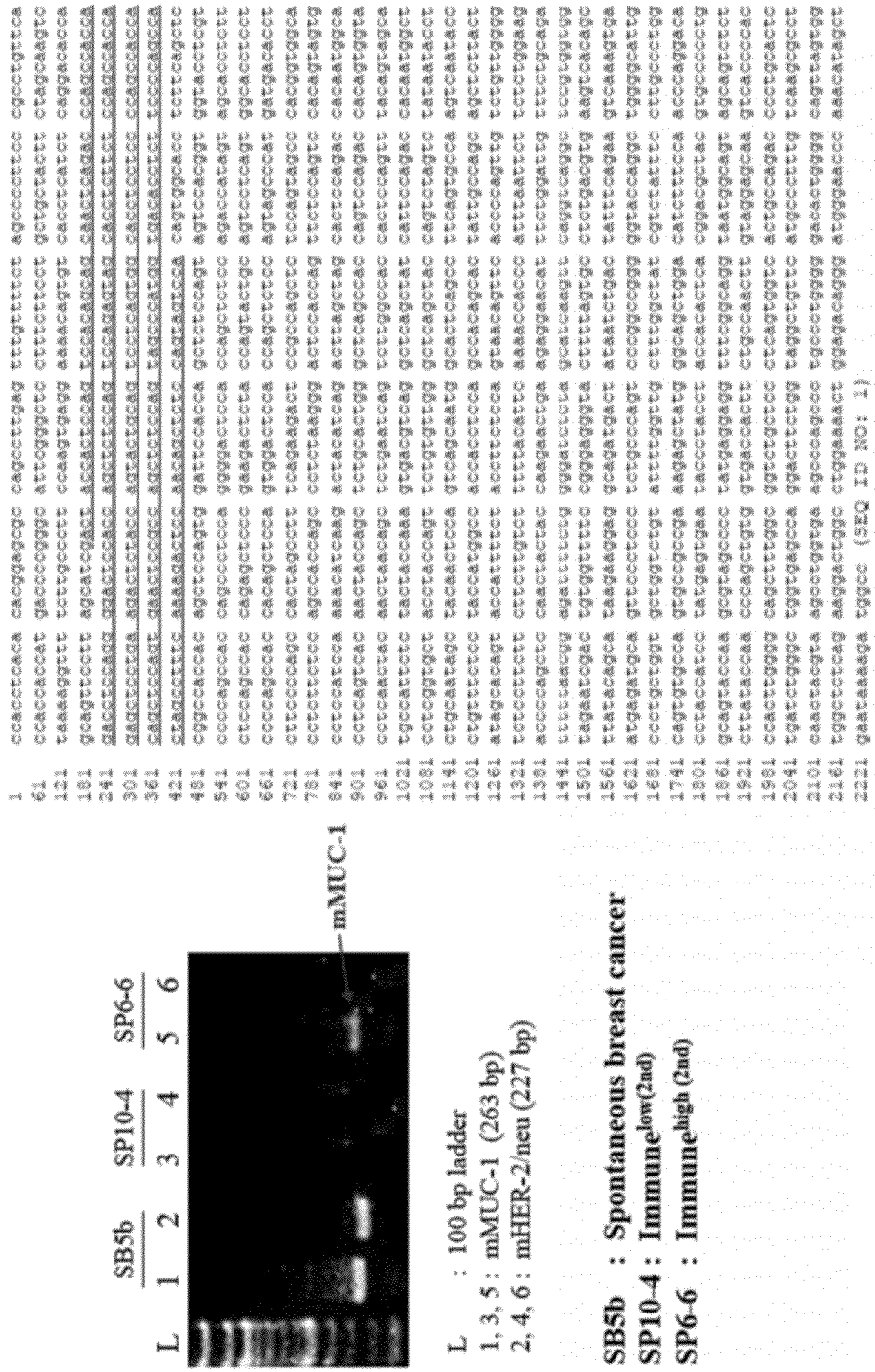
FIG. 22. RT-PCR for MUC-1, a known breast cancer antigen, was performed on extracts of the immuno$^{high}$ pool of transfected cells. The highlighted sequence indicates the portion of the molecule chosen for amplification. As controls, the same procedure was followed except that extracts of immuno$^{low}$ pool or non-enriched cell suspensions from the Master Pool were substituted for extracts from the immuno$^{high}$ pool. As an additional control, RT-PCR was performed to detect HER-2-neu.

Detection of Muc-1, a Known Breast Cancer Antigen, in Cells from the Immuno$^{high}$ Pool of cDNA-Transfected Cells RT-PCR was used to determine if cells from the immuno$^{high}$ pool specified Muc-1, a known breast cancer antigen. The results, presented in the FIG. 22, revealed the presence of Muc-1 both in SB5b breast cancer cells and in cells from the immuno$^{high}$ pool. Muc-1 was not detected by this method in cells from the immuno$^{low}$ pool. An analogous procedure was used to detect the presence of HER-2/neu. As indicated in FIG. 22, HER-2/neu was detected in SB5b cells, but not in either the immuno or the immuno$^{low}$ pool.

Figure 23:
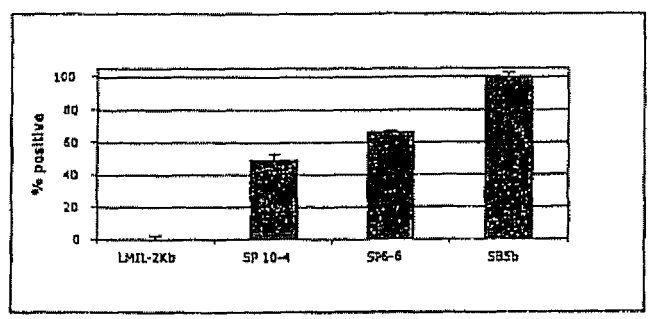
FIG. 23. 1×10$^6$ transfected fibroblasts from the immuno$^{high}$ (SP 6-6) pool, and for comparison non-transfected modified fibroblasts (LM-IL-2K$^b$) and cells from the immuno$^{low}$ pool (SP 10-4), together with the SB5b breast cancer cells were washed with PBS. The cells were then permeabilized with 1 ml of Cytofix/Cytoperm™ (from BD Bioscience, San Diego, Calif.) at 4° C. for 20 min in the dark followed by additional washings. 1 ug of Muc-1 antibody (2 ul in 0.5 mg/ml) (anti-hamster Muc-1; CT2) was added to stain each cell type for 30 min at 4° C. After washing, FITC labeled anti-hamster IgG was added for 30 min at 4° C. After additional washes, the cells were analyzed by flow cytometry.

A monoclonal antibody for the cytoplasmic domain of Muc-1 was used to determine the relative staining intensity of cells from the immuno$^{high}$ and immuno$^{low}$ pools of transfected cells. The results are presented in the FIG. 23 which shows that the staining intensity of cells in the immuno$^{high}$ pool (SP 6-6) was significantly (P<0.01) higher than that of cells from the immuno$^{low}$ pool (SP 10-4). Non-transfected cells (LM-IL-2K$^b$) cells failed to stain. The staining intensity of SB5b breast cancer cells, the source of cDNA used to transfect LM-IL-2K$^b$ cells, exceeded that of any of the other cell-types.

Example 17

Strategy for Identification Genes Specifying Therapeutic Breast Cancer Antigens

An oligonucleotide-based Affymetrix Mouse Genome 430 2.0 GeneChip Array can be used for identification of the antigens. Cells are collected from five experimental groups: initial master pool of transfected cells, selected sub pools of immuno$^{high}$ and immuno$^{low}$ cells, breast cancer cells alone and non transfected fibroblasts. Each experimental group is technically replicated three times starting from 3 separate labeling reactions per RNA sample. Total cellular RNA is isolated with the use of RNeasy columns (Qiagen) according to the manufacturer's protocol. All labeling reactions and hybridizations are carried out according to the standard GeneChip® eukaryotic target labeling protocol (Affymetrix). Briefly, 1-5 µg total cellular RNA per sample is used to synthesize the double-stranded cDNA, which then will be transcribed in vitro in the presence of biotinylated dNTPs. Biotinylated target cRNA will be fragmented and brought up in hybridization mix. Successful labeling of all the samples (a minimum of 15 µg of IVT product per sample) is followed by the test array hybridizations. Test hybridizations is performed with the use of "Test3" arrays (Affymetrix) to ensure quality of the biotinylated target. (Test3 array contains probe sets corresponding to commonly expressed genes from the human, mouse, rat, and yeast genomes along with prokaryotic control genes.) Successful test hybridizations indicating efficient cRNA amplification and strong target hybridization activity is followed by actual experimental hybridizations. Hybridizations are followed by binding to streptavidin-conjugated fluorescent marker. Detection of bound probe will be achieved following laser excitation of the fluorescent marker and scanning of the resultant emission spectra using a scanning confocal laser microscope.

Data acquisition is performed using Affymetrix GeneChip Operating Software Package. Collected hybridization images is subjected to quality control to remove from analysis arrays failed to meet criteria both suggested by Affymetrix and developed internally. These quality requirements include: low Q-noise (1-10); low background (less than a 100); sample dependant percent of probes, detected as present (20-50% for mammals); 3'/5' ratio of no more than 3; hybridization efficiency defined by intensities detected for the spike control probe sets (preferably higher than 2,000 fluorescent units); minimal deviation of scaling factors for the whole set of arrays to be analyzed.

Expression profiles of the cells derived from each selected sub pool (immuno$^{high}$ and immune$^{low}$) are compared to the transcriptional profile of the initial super pool of transfected cells. Hybridization intensity values collected from all experimental samples are subjected to background correction, normalization, and statistical significance analysis with the use of S+ArrayAnalyser statistical software package. Identified statistically significant differentially expressed transcripts will be initially annotated with the use of the NetAffx Analysis Center according to the most up to date version of Gene Ontology Database. More advanced functional annotation is performed with the use of the Pathway Assist software package.

Changes in the transcript expression levels as detected by Affymetrix experiments are verified by real-time PCR Reactions are performed in a Perkin-Elmer/-Applied Biosystems ABI PRISM 770 Sequence Detection system. Primers are designed for each selected gene, based on the sequence information available through the Affymetrix NetAffx web-based resource. Primer design is performed using Primer Express 1.5 software. The primers are validated, standardized, and used on cDNA prepared from test samples.

Figure 24:
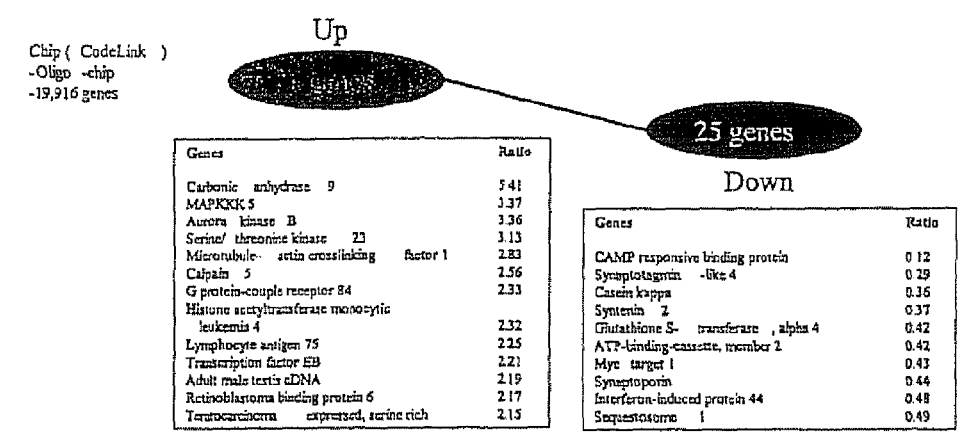
FIG. 24. Comparison of gene expression in immuno$^{high}$ and immuno$^{low}$ pools of transfected cells.

As shown in FIG. 24, the primary objective is to use the enrichment strategy to identify genes specifying therapeutic breast cancer antigens. Microarrays were performed on immuno$^{high}$ and immuno$^{low}$ cell pools to detect differences in gene expression between to two pools.

Figure 25:
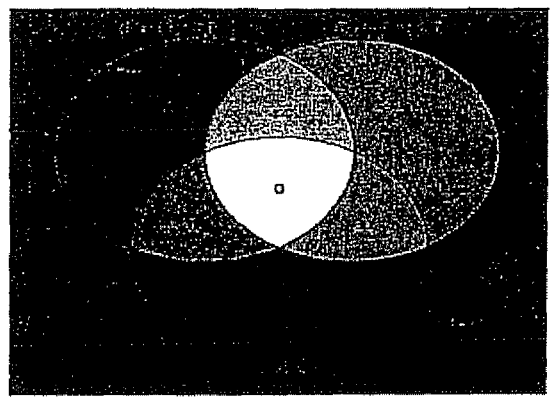
FIG. 25. Number of genes over-expressed in immuno$^{high}$ and immuno$^{low}$ pools.

Data in FIG. 25 compare differences in gene expression in immuno$^{high}$ pools and immuno$^{low}$ pools as well as the non-transfected modified fibroblasts used as recipients of cDNA from the breast cancer cells (SB5b). One hundred forty one identifiable genes were overexpressed in cells from the immuno$^{high}$ pool of transfected cells.

Ontologic classification of genes over-expressed by immune$^{high}$ cells and several candidate genes chosen for further study are presented in the following Table.

| GenBank # | Gene name | Ratio |
|---|---|---|
| Receptor activity | | |
| NM 030721 | G-protein-couple receptor 84 | 2.4 |
| NM 46590 | Olfactory receptor Mor1 | 2.3 |
| NM 009107 | Retinoid receptor X gamma | 2.0 |

-continued

| GenBank # | Gene name | Ratio |
|---|---|---|
| RNA/DNA binding | | |
| NM 011247 | Retinoblastoma binding protein 6 | 2.2 |
| NM 011585 | Cytotoxic granule-associated RNA-binding protein | 2.4 |
| NM 011549 | Transcription factor EB | 2.1 |
| Metabolism | | |
| NM 139305 | Carbonic anhydrase 9 | 5.4 |
| NM 007955 | Protein tyrosine phosphatase receptor type V | 2.3 |
| A1593846 | MAPKK5 | 3.4 |
| Cell constituent | | |
| NM 00729 | Procollagen, type XI, alpha 1 | 2.1 |
| Others | | |
| AA120189 | Aurora kinase | 3.4 |
| BG074447 | Rap guanine nucleotide exchange factor 1 | 3.3 |
| CANDIDATE GENES | | |
| AK006529 | *Mus musculus* adult male testis | |
| NM 013825 | Lymphocyte antigen 75 | |
| NM 019643 | Teratocarcinoma expressed, serine rich | |
| NM 011247 | Retinoblastoma binding protein 6 | |

Legend:
Candidate genes are those chosen initially for further study to verify their immunotherapeutic properties.

Example 18

Immunotherapy of Breast Cancer with Cellular Vaccines that Express Defined Breast Cancer Antigens Treatment protocols will be used to test the immunotherapeutic properties of fibroblasts modified to express identified TAA in mice with established breast cancer. Tumors will be established in syngeneic C3H/He or BALB/c mice as appropriate susceptible to the growth of the syngeneic breast cancer cells. The mice will be treated with a cDNA-based vaccine that expresses defined TAA. We will use cells transfected with cDNA specifying TAA that were found by ex vivo analyses (ELISPOT and $^{51}$Cr-release cytotoxicity assays) to stimulate immunity to the breast cancer to the greatest extent.

On day 0, breast cancer cells are injected into the fat pad of the breast. The number of tumor cells to be used in these experiments will be determined by the results of the prior studies. If, for example, the treatment deterred growth of $2 \times 10^6$ cells and prevented the growth of $1 \times 10^6$ cells, $1 \times 10^6$ cells would be used. Thus, as the size of the tumor progressed after implantation, we can determine the point at which the burden exceeds the therapy.

On days 1, 2, 5, 10 and 15 after injection of the breast cancer cells, the mice will be immunized by s.c. injections of the vaccine. After four immunizations, two animals from each group will be sacrificed. Spleen cell suspensions will be tested in both ELISPOT and $^{51}$Cr-release cytotoxicity assays from labeled breast cancer cells, used as targets. As a control, naive mice will be euthanized and their spleen cells will be tested in the same manner. This will provide the "before treatment" data since the mice are inbred. Survival will be measured in days post treatment. Our preliminary data and prior experience indicate that the treatment of mice with smaller tumor burdens will be successful. It is also expected that by allowing the tumor to increase in size, to grow unchecked for a number of days, the burden will eventually become be too large to be purged by the immune system. Nevertheless, even if no group remains tumor free, there will be a difference in the time to first appearance of the tumor mass in the treated group, and in overall survival.

The increased survival of mice in the groups receiving therapy should correlate with the delay in time until the measurable tumor first appears. These experiments will provide greater insight into the capacity of treatment with vaccines that express defined antigens to affect existing tumors and the maximum size of the tumor burden that can be successfully treated by immunization with the vaccines. Control groups including mice treated with cDNA transfected cells from melanoma will included to determine the specificity of the response. As an additional control, the mice will be treated according to the same protocol with non-transfected fibroblasts. Untreated animals injected with the breast cancer cells alone will form the base for evaluation of the therapeutic response. We plan to test at least ten individual, defined TAA by this approach. Our expectation is that the immunotherapeutic properties of each of the TAA will not be the same.

Example 19

Immunotherapy of Breast Cancer with Cellular Vaccines that Express Multiple Defined Breast Cancer Antigens As noted previously, the metastatic spread and aggressiveness of the growth of cancer cells in the patient results from the varied genotype of cells within the malignant cell population. Numerous random mutations generate subpopulations of cancer cells that are capable of invasion and metastasis. Others changes lead to the appearance of cancer cells that able to resist drugs commonly used for chemotherapy.

It is likely that multiple altered and dysregulated genes specifying weakly immunogenic TAA are present in cancer cells. Immunization with a vaccine, therefore, that expresses multiple TAA may be more successful in eliminating a greater proportion of the malignant cell population than a vaccine that expresses a single TAA. Although the major thrust of this proposal is the identification of therapeutic breast cancer TAA, we will determine the immunotherapeutic properties of vaccines that express multiple defined TAA. In Section 2.2, we described vaccines that expressed multiple TAA. We will compare the immunotherapeutic properties of vaccines that express multiple defined TAA with those that express a single TAA, using the following the protocol outlined above. These experiments will determine the relative immunotherapeutic properties of single epitope vaccines with multiple epitope vaccines. One hundred percent of the transfected cells are expected to express the defined antigens chosen for study.

Example 20

Identification of the Cell Types Activated for Immunity to Breast Cancer in Mice Immunized with cDNA Transfected Cells that Express Defined TAA The cell types mediating the rejection of neoplasms in mice with breast cancer treated with cDNA-transfected cells that express defined TAA have not been defined. Conceivably, different TAA stimulate different classes of immune-effector cells. To investigate this question, naive syngeneic mice will first be depleted of specific T cell subsets by i.p. injections of anti CD4 monoclonal antibody (GK1.5 rat hybridoma), anti CD8 monoclonal antibody (83-23-5 mouse hybridoma) or NK/LAK antibody (asialo GM1). The depleted mice will then be injected into the fat pad of the breast with syngeneic breast cancer cells, followed by immunization with the vaccines that express defined TAA.

The extent of T cell-depletion will be determined by FACS analysis. (Our prior experience indicates that more than 99 percent of the relevant T cell subtype can be depleted from the mice by this approach.) C3H/He mice will be injected into the fat pad of the breast with $5\times10^4$ syngeneic SB5b cells. The tumors will be allowed to grow to approximately 5 mm$^3$ before beginning treatment with the vaccine. As controls, additional naive mice are injected with an irrelevant, isotype-specific monoclonal antibody according to the same schedule, or with an equivalent numbers of breast cancer cells alone. The survival of mice in the groups injected with breast cancer alone and the irrelevant monoclonal antibody form the reference against which the effect of cell depletion is measured. We analyze the cell types mediating resistance to the breast cancer for ten defined breast cancer TAA.

This approach defines the cell types mediating tumor rejection in mice immunized with vaccines that express defined TAA. It further outlines the parameters of the therapeutic benefits of the vaccines in the treatment of mice with breast cancer. It characterizes the immunologic underpinning responsible for the vaccines' beneficial effects.

Example 21

Creation of a Hierarchy of Breast Cancer Antigens Based on their Relative Immunotherapeutic Properties In his classic paper, Gilboa described four categories of tumor antigens. The antigens were divided into "patient specific (incidental mutated gene products)," "tumor-specific" (mutated related to the oncogenic process)," "tissue restricted," (e.g., MAGE) and "Others," that included differentiation antigens such as gp100. We wish to apply the strategy outlined in this proposal to create a hierarchy of TAA that stimulate immunity to breast cancer. The hierarchy is based upon the antigen stimulates immunity to breast cancer to the greatest and to the least extent. We determine the relative immunogenic properties of each prototype TAA by both ex vivo (ELISPOT and $^{51}$Cr-release assays) and in vivo studies designed to determine the vaccines' immunotherapeutic properties in tumor-bearing mice. Our long-term objective is to develop a vaccination strategy that can be of benefit to breast cancer patients. Our expectation is that not all breast cancer TAA will be equally efficacious in promoting breast cancer immunity. The results of this important investigation will enable us to describe the basic characteristics of the desired TAA. It will provide a guide for the vaccines that can be used most effectively in the clinical studies to follow.

Example 22

Analysis by Limiting Dilution to Determine the Proportion of Transfected Fibroblasts That Express Breast Cancer Antigens It is likely that a subpopulation of cells incorporated therapeutically relevant genes that specified antigens associated with the breast cancer cells. We will use an assay based on limiting dilution and the application of Poisson statistics to determine the proportion of the transfected cell-population that induced the anti tumor response. (Poisson distribution is a statistical function that describes how objects are distributed at random. For instance, when different numbers of transfected cells are distributed into a series of culture wells, some wells will receive no TAA-positive cells, some will receive one TAA-positive cell, some two, and so on. From the Poisson distribution it is known that there is on average one TAA-positive cell per well when the frequency of negative wells is 37%). Varying numbers (range=$5\times10^3$ to $1\times10^5$) of immuno$^{high}$ and immuno$^{low}$ cells are distributed to 20 replicate wells at each cell number.

The plates are incubated for five days at 37° C. under standard cell culture conditions, to allow the cells to proliferate. Afterward, cells from individual wells are transferred to culture flasks. After further cell proliferation, naïve C3H/He mice are immunized with cells derived from individual wells. The mice receive three injections at weekly intervals of $5\times10^6$ cells. There are three mice in each group. One week after the last injection, the mice are challenged by an injection of $5\times10^3$ SB5b cells. Inhibition of tumor growth and the induction of spleen cell-mediated immunity to the breast cancer cells can be used as an indication of the relative proportion of cells in the transfected cell population that expressed TAA.

Figure 26:
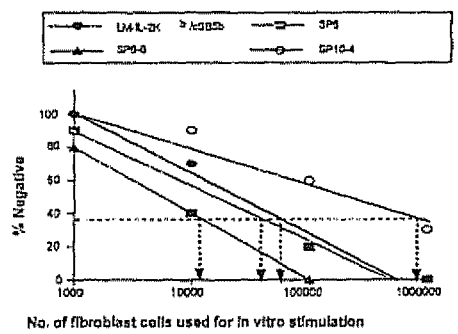
FIG. 26. Frequency of antigen-positive cells in immuno$^{high}$ sub pools of transfected cells.

As shown in FIG. 26, the analysis indicates that approximately 1 in 10,000 cells in the immuno$^{high}$ pool SP6-6 expressed breast cancer TAA. This assay defines the proportion of transfected cells that express "therapeutically relevant" TAA (promote tumor regression) that characterize the breast cancer cells. The studies determine the fundamental basis of the therapeutic effects in mice with breast cancer. It tests the hypothesis that a vaccine composed mainly of DNA transfectants that express tumor antigens is likely to be more therapeutically effective than one containing DNA transfectants that express few relevant tumor antigens.

Example 23

Testing Vaccines that Express Defined Tumor Antigens for Toxicity, Including the Possible Generation of Systemic or Organ Specific Autoimmune Disease in Vaccinated Animals No evidence of toxic effects in mice injected with DNA-based vaccines was detected in our previous experiments. The animals lived their anticipated normal, expected life spans without evidence of disease. As described, the vaccine, which expresses allogeneic determinants, like other allografts was rejected. In this study, vaccines are prepared that express defined TAA. One hundred percent of the transfected cells express the defined TAA chosen for analysis. Conceivably, immunization with a strongly potent vaccine can result in the generation of autoimmunity in the breast, and elsewhere. We can carry out additional experiments to investigate this important question. To determine if mice immunized with the DNA-based vaccines that express defined TAA develop autoimmune disease, we can carry out the following assays: for signs of generalized autoimmunity, we can prepare H and E sections of skin, brain, thyroid, heart, liver, kidney, breast, lung, stomach, and ovary. The microscopic sections can be examined for signs of inflammation, as characterized primarily by mononuclear cell infiltrates. The presence of immune complexes can be determined by standard immunohistochemical staining. To detect the presence of autoantibody to a diffuse antigen, we can assay for the presence of anti nuclear antibody (ANA) as well as antibodies to desmoglein 3, expressed by keratinocytes in the skin. To detect the presence of autoantibody to an organ specific antigen, we can perform assays for antibodies for thyroid peroxidase, thyroglobulin, and thyrotropin receptor. We can carry out these assays in animals immunized for each of the vaccines investigated in this study. In each instance, the animals are maintained through their anticipated life spans in the event delayed toxic effects appear.

The lack of autoantibodies or cellular infiltrates is strong evidence that the vaccine is not toxic and does not induce autoimmune disease.

It is likely that those breast cancer antigens that have been identified represent only a small proportion of the total array of TAA within the tumor cell population. Until now, the identification of breast cancer antigens has depended upon their relative over expression and altered molecular characteristics in tumor cells, when compared to non-malignant cells from the tumor-bearing host. In this innovative approach, we describe a new method for the identification of breast TAA. Our expectation is that anti tumor immune responses following immunization with vaccines that specify defined, highly immunogenic breast cancer antigens may exceed those of vaccines prepared from unfractionated tumors. This approach can become an important adjunct to conventional therapy in the treatment of breast cancer patients.

Example 24

Cytokine-Secretion by LM Mouse Fibroblasts Transduced with PZipNeoSVIL-2, Retroviral Vector Specifying IL-2

Among other advantages, the use of a fibroblast cell line as the recipient of DNA from the SCC enables the recipient cells to be conveniently modified in advance of DNA-transfer to augment their nonspecific immunogenic properties. In this instance, the fibroblasts, of C3H/He mouse origin, were modified to secrete IL-2 and to express additional allogeneic MI-IC class I-determinants (described, below). Allogeneic MHC class I-determinants are strong immune adjuvants and ensure that the vaccine will be rejected (Ostrand-Rosenberg S, J Immunol 1990; 144:4068-71; Fearon E R, Cancer Res 1988; 48: 2975-80; Nabel G J, Proc Natl Acad Sci USA 1996; 93: 15388-93; DeBniyne L. Cancer Immunol Immunother 1996; 43:180-9).

A replication-defective retroviral vector (pZipNeoSVIL-2) was used to modify the cells to secrete IL-2. The vector specified the gene for human IL-2 along with a gene (neo$^r$), which conferred resistance to the neomycin analog 6418. (Like mouse IL-2, human IL-2 stimulates the proliferation and maturation of mouse T cells.) After selection in growth medium containing sufficient quantities of G418 to kill one hundred percent of non-transduced cells (600 µg/ml), the surviving colonies were pooled and maintained as a cell line (LM-IL-2 cells). An analysis by ELISA of the culture supernatants of LM-IL-2 cells indicated that $10^6$ retrovirally-transduced cells formed 196 pg IL-2/ml/$10^6$ cells/48 hrs. The culture supernatants of LM fibroblasts transduced with the IL-2 negative vector pZipNeoSV (X), like that of non-transduced LM cells, failed to form detectable quantities of IL-2. Every third passage, the transduced cells were placed in medium containing 600 µg/ml G418. Under these circumstances, equivalent quantities of IL-2 were detected in the culture supernatants of cells transduced with pZipNeoSVIL-2 for more than six months of continuous culture. The generation time of transduced and non-transduced fibroblasts, approximately 24 hrs in each instance, were equivalent. The introduction of genomic DNA-fragments from the SCC into the IL-2-secreting cells did not affect the quantity of IL-2-secreted (these data are not presented).

Example 25

Modification of LM Fibroblasts to Express Allogeneic MHC class I (H-2K$^b$)-Determinants The SCC used in the study originated in DBA/2 mice (H-2$^d$). H-2K$^b$-determinants are allogeneic in this mouse strain. To further augment their immunogenic properties, the IL-2-secreting fibroblasts (of C3H/He mouse origin (H-2$^k$) were also modified to express H-2K$^b$-determinants. A plasmid, pBR327H-2K$^b$, specifying H-2K$^b$-determinants was used for this purpose. LM-IL-2 cells were co-transfected with pBR327H-2K$^b$ DNA along with the vector pBabePuro (confers resistance to puromycin), used for selection. A 10:1 ratio of pBR327H-2K$^b$ to pBabePuro was used to ensure that the cells that took up pBabePuro DNA incorporated pBR327H-2K$^b$ DNA as well. After selection in medium containing sufficient quantities of puromycin to kill one hundred percent of non-transduced cells, the surviving colonies were pooled and maintained as cell line (LM-IL-2K$^b$ cells).

Quantitative immunofluorescence measurements with PE-labeled mAbs for mouse H-2K$^b$ determinants were used to measure expression of the class I-determinants. As a control, aliquots of the puromycin-resistant cell suspension were incubated with PE-conjugated IgG2a isotype Ig.

1×10$^6$ LM fibroblasts transduced with the plasmid pBR327H-2K$^b$ (LM-IL-2K$^b$ cells) suspended in 100 ul PBS were incubated for 1 hr at 37° with PE-conjugated H-2K$^b$, H-2K$^k$ B7.1 (CD 80) or I-A mAbs. As controls, the same procedure was followed except that (non-transduced) LM cells, LM-IL-2K$^b$ cells transfected with DNA-fragments from KLN205 cells (LM-IL-2K$^b$/KLN, Master pool)) or LM-IL-2K$^b$/KLN cells from sub pools after three rounds (3°) of immune selection were substituted for LM-IL-2K$^b$ cells. As an additional control, PE-conjugated IgG2a isotype Ig was substituted for the mAbs. After incubation, the cells were washed and analyzed for fluorescent staining by flow cytofluorometry. Dark-shaded area: Cells stained with PE-conjugated anti-H-2K$^b$, H-2K$^k$, B7.1 or I-A mAbs. Light line: Cells stained with PE-conjugated isotype Ig.

The results (FIG. 10) indicated that more than 99 percent of the transduced fibroblasts stained positively (MFI at least ten fold greater than cells stained with PE-conjugated isotype Ig, taken as background). Under similar conditions, non-transduced LM cells (of C3H/He mouse origin, H-2$^k$) or fibroblasts stained with PE-conjugated isotype Ig failed to stain above background. The introduction of DNA from KLN205 cells into the transduced fibroblasts did not affect the intensity of immunofluorescent staining. The expression of H-2K$^b$-determinants by the transduced cells was a stable property. The staining intensity was essentially unchanged after three months of continuous culture.

An analogous procedure was used to further characterize the cells used as DNA-recipients. The modified fibroblasts were stained with PE-labeled mAbs for H-2K$^k$ class I-determinants or with PE-labeled mAbs for the co-stimulatory molecule B7.1 or I-A class II MHC determinants. The results indicated that the fibroblasts expressed H-2K$^k$ determinants constitutively (MFI 10.9±1.1). Both transduced and non-transduced LM cells also expressed B7.1, but not I-A determinants (MFIs 4.6±0.7, 0.9±0.8 and 1.8±0.7 respectively). The expression of MHC class I-determinants and the co-stimulatory molecule by LM cells was consistent with various reports indicating that fibroblasts, like dendritic cells, are efficient antigen presenting cells (Alberg A J, J Clin Oncol 2005; 23:3175-85; Morse M A, Cancer Res 2005; 65:553-61; Hirschowitz E A, 3 Clin Oncol. 2004; 22:2808-15; Raez L E, J Clin Oncol 2004; 22:2800-7).

Example 26

Figure 11:
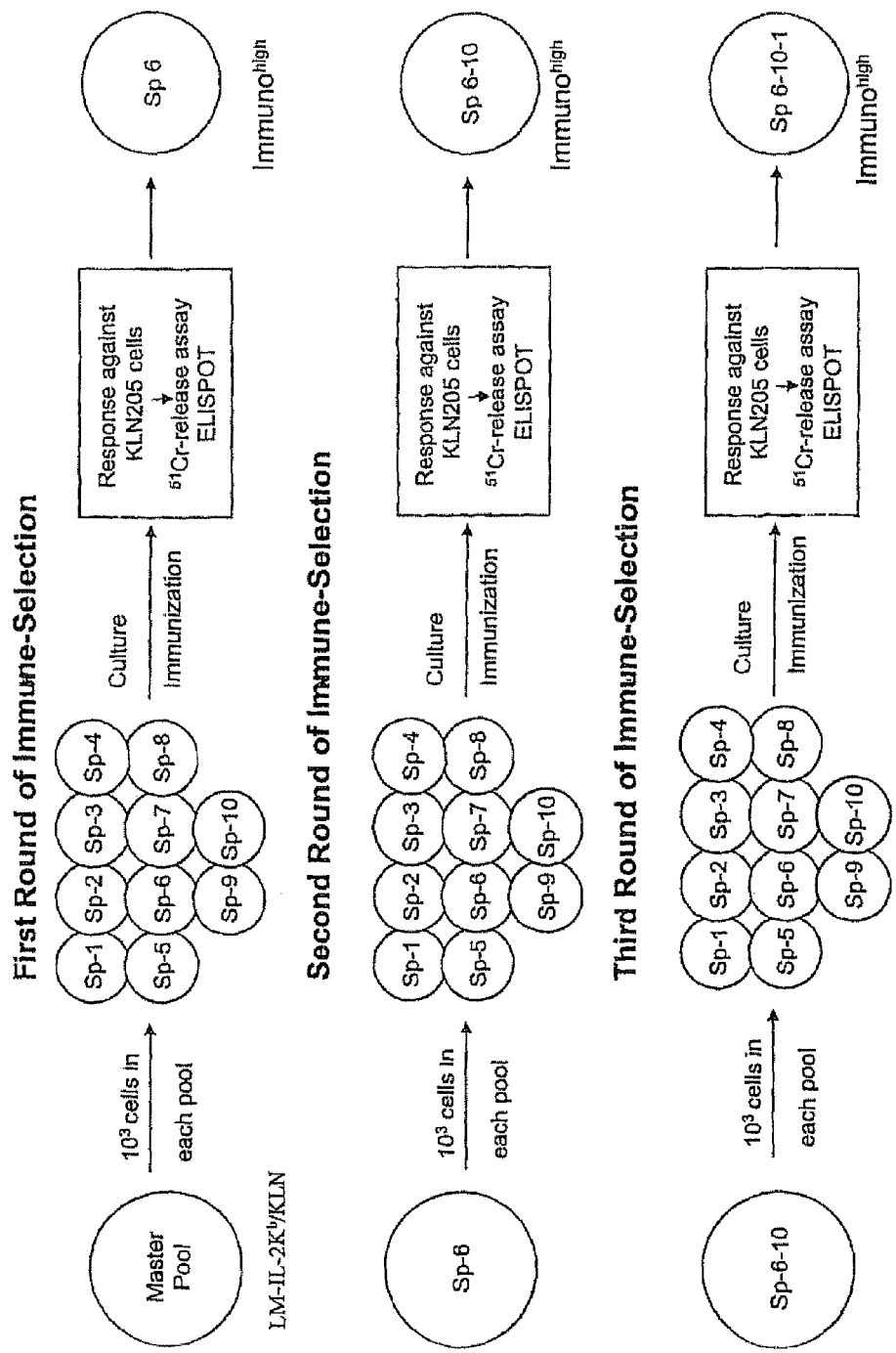
FIG. 11 is schematic of the strategy used to enrich LM-IL-2K$^b$/KLN cells for cells that induce immunity to KLN205 cells in DBA/2 mice.

Strategy for the Enrichment of the Cellular Vaccine for Cells that Induce Immunity to Squamous Carcinoma in DBA/2 Mice and Identification of Highly Immunogenic (immuno$^{high}$) Pools of Transfected Cells A cellular vaccine for SCC was prepared by transfer of 25 kb DNA-fragments from KLN205 cells into LM-IL-2K$^b$ cells. A novel enrichment strategy was devised since only a small proportion of the transfected cell population would be expected to induce the anti tumor immune response in the immunized mice. The strategy, outlined in FIG. 11, was designed to enrich the transfected cell-population for cells that induced immunity to the SCC. LM-IL-2 cells were transfected with sheared DNA-fragments from KLN205 cells, along with a plasmid (pHyg) conferring resistance to hygromycin B, used for selection, as described. After selection, small aliquots (1×10$^3$) of the transfected cells were added to each of ten wells of a 96 well plate. The cells were cultured under standard conditions. A portion of the expanded cell population was maintained frozen/viable. The remaining portion was used to immunize DBA/2 mice. Spleen cells from mice immunized with cells from the individual pools were then tested by $^{51}$Cr-release cytotoxicity and ELISPOT IFN-γ assays for their immunogenic properties against KLN205 cells. The objective was to identify the pool that stimulated immunity to KLN205 cells to the greatest (Immuno$^{high}$) and least (Immuno$^{low}$) extent. Frozen/viable cells from the Immuno$^{high}$ and the Immuno$^{low}$ pools were reestablished in culture. Small aliquots (1×10$^3$) of cells from each of these pools were then added to each of ten wells of a 96 well plate and the process was repeated for two additional rounds of immune selection. Master pool=LM-IL-2K$^b$/KLN cells before immune selection. Sp-6-10=LM-IL-2K$^b$/KLN cells from subpool 6 after two rounds of immune selection. Sp-6-10-1=LM-IL-2K$^b$/KLN cells from subpool 6 after three rounds of immune selection.

Small aliquots of the transfected cell-population were added to individual wells of a 96 well plate. We reasoned that if the starting inoculums were sufficiently small, then some pools would contain greater numbers of highly immunogenic cells than others. Pools containing greater numbers of immunogenic cells could be identified by their heightened immunogenic properties against KLN205 cells in immunized DBA/2 mice. To test this strategy, we added 1×10$^3$ transfected cells to each of ten wells of a 96 well cell culture plate. As the cell number increased, cells from individual pools were transferred to progressively larger cell culture plates, and then flasks. After the number of cells from individual wells had increased to about 5×10$^7$, a portion of the expanded cell population from each pool was collected and maintained frozen/viable. The remaining portion was used to immunize naïve DBA/2 mice. After immunization, two independent means (ELISPOT-IFN-γ and $^{51}$Cr-release cytotoxicity assays) were used to identify pools that stimulated spleen cell-mediated immunity toward KLN205 cells to the greatest (immuno$^{high}$) and least (immuno$^{low}$) extent.

Figure 12:
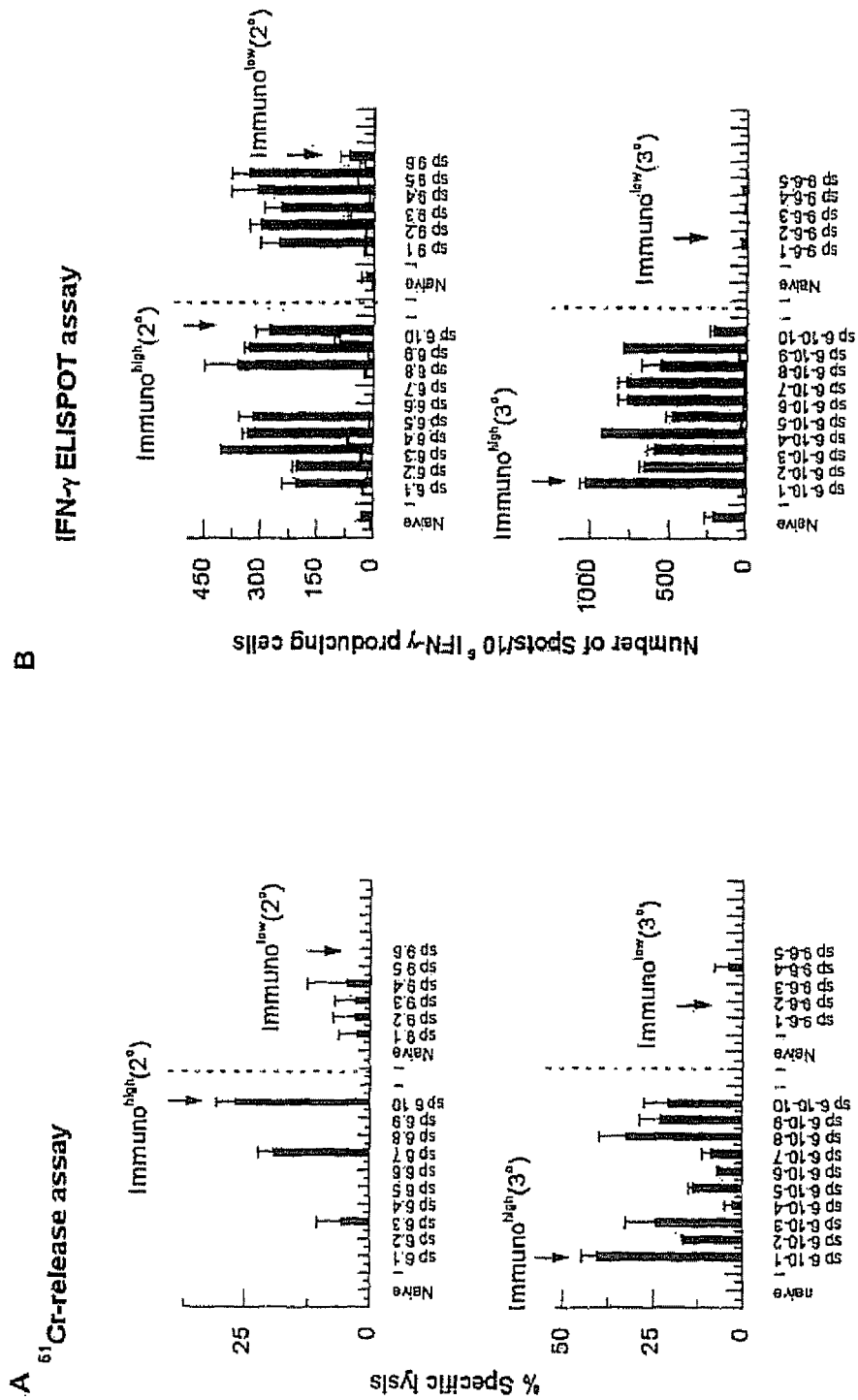
FIG. 12 shows screening of various pools of LM-IL-2K$^b$/KLN cells for cells that induce immunity to KLN205 cells to the greatest (Immuno$^{high}$) and least (Immuno$^{low}$) extent.

As shown in FIG. 12A, DBA/2 mice received two s.c. injections at weekly intervals of 4×10$^6$ cells from individual pools of LM-IL-2K$^b$/KLN cells. One week after the second injection, spleen cells from mice immunized with cells from the individual pools were co-incubated for 5 days with (mitomycin C-treated) KLN205 cells (E:T ratio=30:1). Afterward, $^{51}$Cr-labeled KLN205 cells were added and the specific cytotoxic activity was determined in a standard 4 hr $^{51}$Cr-release assay.

The same procedure as described in (12A) was followed for FIG. 12B, except that the spleen cells were co-incubated for 18 hr with (mitomycin C-treated) KLN205 cells (E:T ratio=10:1) before they were analyzed in ELISPOT-IFN-γ assays. As controls, spleen cells from naïve mice were substituted for spleen cells mice immunized with the transfected cells.

Immuno$^{high}$ (2°)=Pool selected for further analysis after two rounds of immune selection. Immuno$^{low}$ (2°)=Pool selected for further analysis after two rounds of immune selection. Immuno$^{high}$ (3°)=Pool selected for further analysis after three rounds of immune selection. Immuno$^{low}$(3°)=Pool selected for further analysis after three rounds of immune selection. The results (FIG. 12) indicated that after the first round of selection the immunogenic properties of transfected cells derived from each pool were not the same. The immunogenic properties of transfected cells from subpool (sp) 6-10-1 exceeded those of any of the other pools (sp 6-10-1=immuno$^{high}$). In a similar manner, cells from sp 9-6-2 stimulated immunity to KLN205 cells to the least extent (sp 9-6-2=immuno$^{low}$). Frozen/viable cells from each of these pools were recovered and the procedure was repeated for two additional rounds of immunoselection, using 1×10$^3$ transfected cells as the starting inoculums in each instance.

Figure 13:
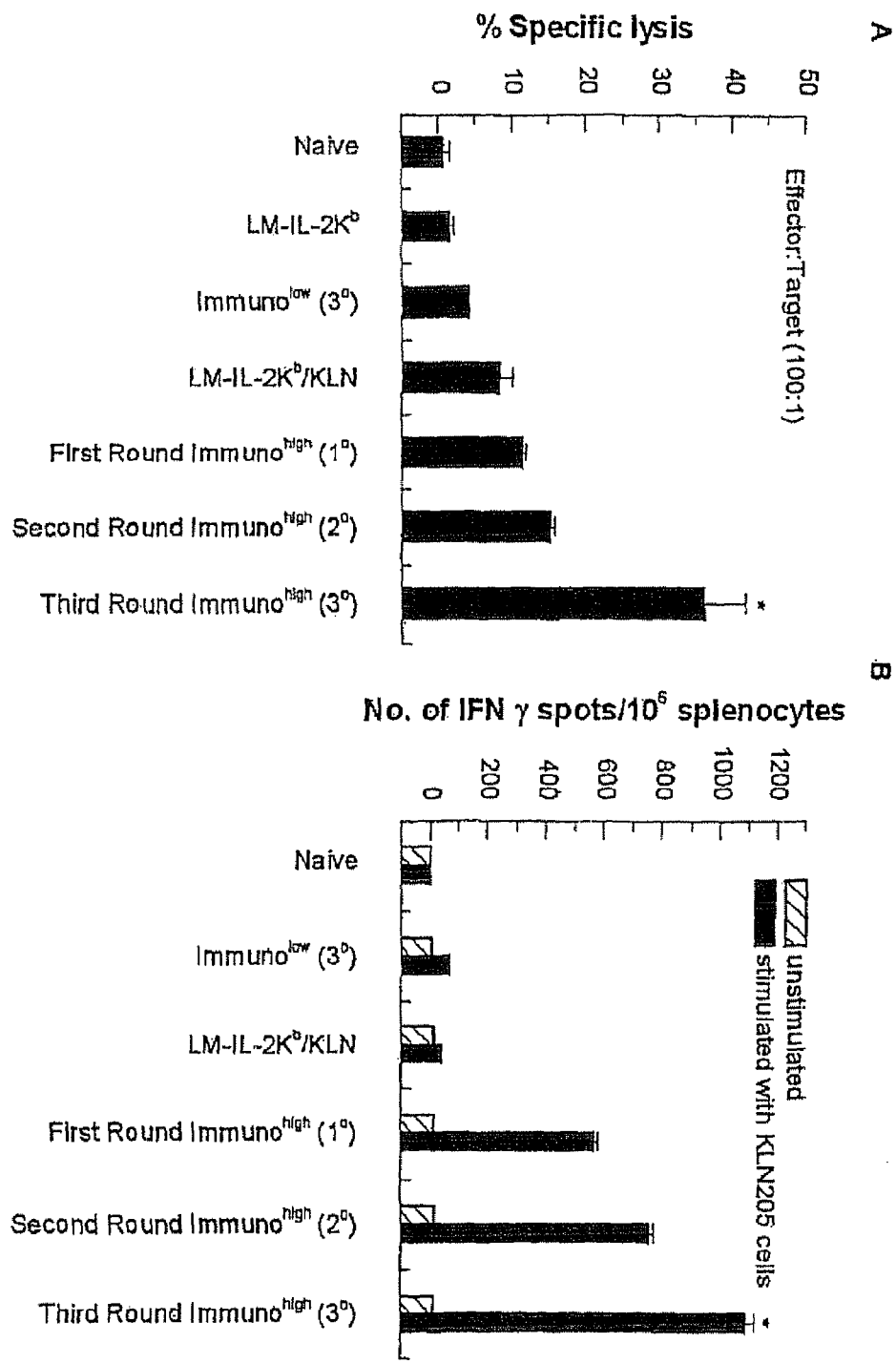
FIG. 13 shows comparison of The Immunogenic Properties of Immuno$^{high}$ Pools of LM-IL-2K$^B$/KLN cells after one, two or three rounds of immune selection.

The strategy resulted in a progressive increase in the immunogenic properties of the cells from the immuno$^{high}$ pools (FIG. 13).

As seen in FIG. 13A, DBA/2 mice were injected s.c. two times at weekly intervals with 4×10$^6$ cells from the Immuno-$^{high}$ subpool (sp) 6-10-1, taken after three rounds (3°) of immune selection. One week later, spleen cells from the immunized mice were co-incubated for 5 days with (mitomycin C-treated) KLN205 cells (E:T ratio=30:1). At the end of the incubation, $^{51}$Cr-labeled KLN205 cells were added and the specific cytotoxic activity toward the labeled cells was determined in a standard 4 hr $^{51}$Cr-release assay. For comparison, the same procedure was followed except that cells taken after one (1°) or two (2°) rounds of immune selection were substituted for cells taken after three rounds (3°) of immune selection. As controls, cells from the non-selected Master Pool or from non-transfected LM-IL-2K$^b$ cells were substituted for transfected cells from the third round of immune selection. As an additional control, cells from the Immuno$^{low}$ pool after three rounds of selection were substituted for cells from the Immuno$^{high}$ pools.

p<0.005 for the specific release of isotope from KLN205 cells co-incubated with spleen cells from mice immunized with cells from the Immuno$^{high}$ (3°) pool and spleen cells from mice immunized with cells from the Immuno$^{high}$ (2°) or Immuno$^{high}$ (1°) pools or with cells from the (non selected) Master Pool. p<0.001 for the specific release of isotope from KLN205 cells co-incubated with spleen cells from mice immunized with cells from the Immuno$^{high}$ (3°) pool and the spleen cells from mice immunized with cells from the Immune$^{low}$ (3°) pool or mice immunized with non-transfected cells.

The same procedure as described in FIG. 13A, was followed in FIG. 13B, except that spleen cells from mice immunized with cells from the various pools were co-incubated for 18 hr with (mitomycin-C-treated) KLN205 cells (E:T ratio=10:1) before they were analyzed in ELISPOT-IFN-γ assays. p<0.001 for the number of spots developing in the group co-incubated with spleen cells from mice immunized with cells from the Immuno$^{high}$ (3°) pool and cells from any of the other pools.

Figure 10:
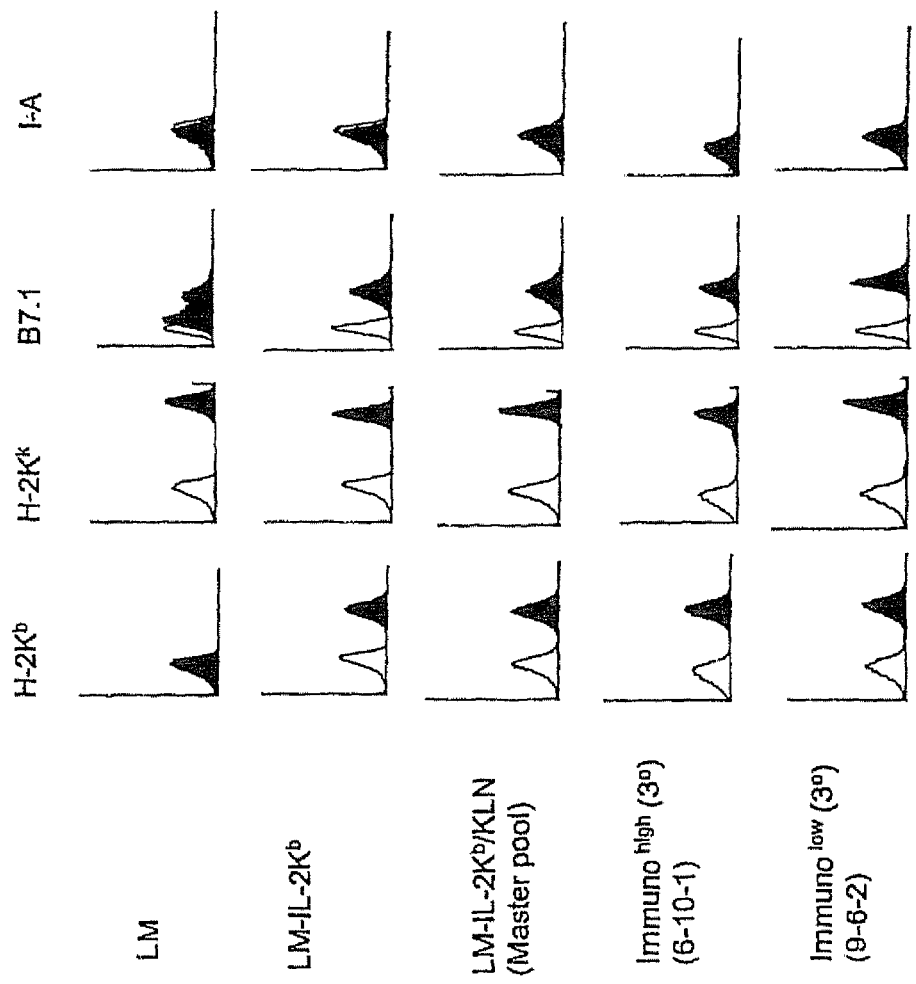
FIG. 10 depicts expression of H-2K$^b$-determinants by LM fibroblasts transduced with pBR327H-2K$^b$, a plasmid vector specifying H-2K$^b$-determinants.

By the second round of immune selection, as determined by $^{51}$Cr-release cytotoxicity and ELISPOT-IFN-γ assays, the immunogenic properties toward KLN205 cells in mice immunized with cells from the immuno$^{high}$ pool sp 6-10 were clearly (p<0.001) greater than those of cells from the initial non selected (Master Pool) or from the immuno$^{low}$ pool sp 9-6. By the third round, the immunogenic properties of cells from the immune$^{high}$ pool were higher than cells from any of the other pools. Cells from the immuno$^{low}$ pools failed to stimulate immunity to KLN205 cells in DBA/2 mice, and presumably contained an insufficient number of immunogenic cells. The expression of MHC class I-determinants of cells from the immuno$^{high}$ and immuno$^{low}$ pools of transfected cells were equivalent (FIG. 10).

Example 27

Tumor Growth was Inhibited and Survival was Prolonged in DBA/2 Mice Immunized with Cells from the immuno$^{high}$ Pool of Transfected Cells To determine if the immunogenic properties of the immuno$^{high}$ pool of transfected cells, as revealed by in vitro measurements, could be extended to mice with SCC, DBA/2 mice were injected s.c. two times at weekly intervals with 4×10$^6$ cells from the immuno$^{high}$ pool (3°). One week later, the mice received a single challenging s.c. injection of 1×10$^6$ KLN205 cells. As controls, the same procedure was followed except that cells from the immuno$^{high}$ pool after the first (1°) or second round (2°) of immunoselection were substituted for cells from the immuno$^{high}$ pool (3°). As additional controls, cells from the nonselected Master Pool or from the immuno$^{low}$ subpool (sp 9-6-2) were substituted for cells from the immuno$^{high}$ pool.

Figure 15:
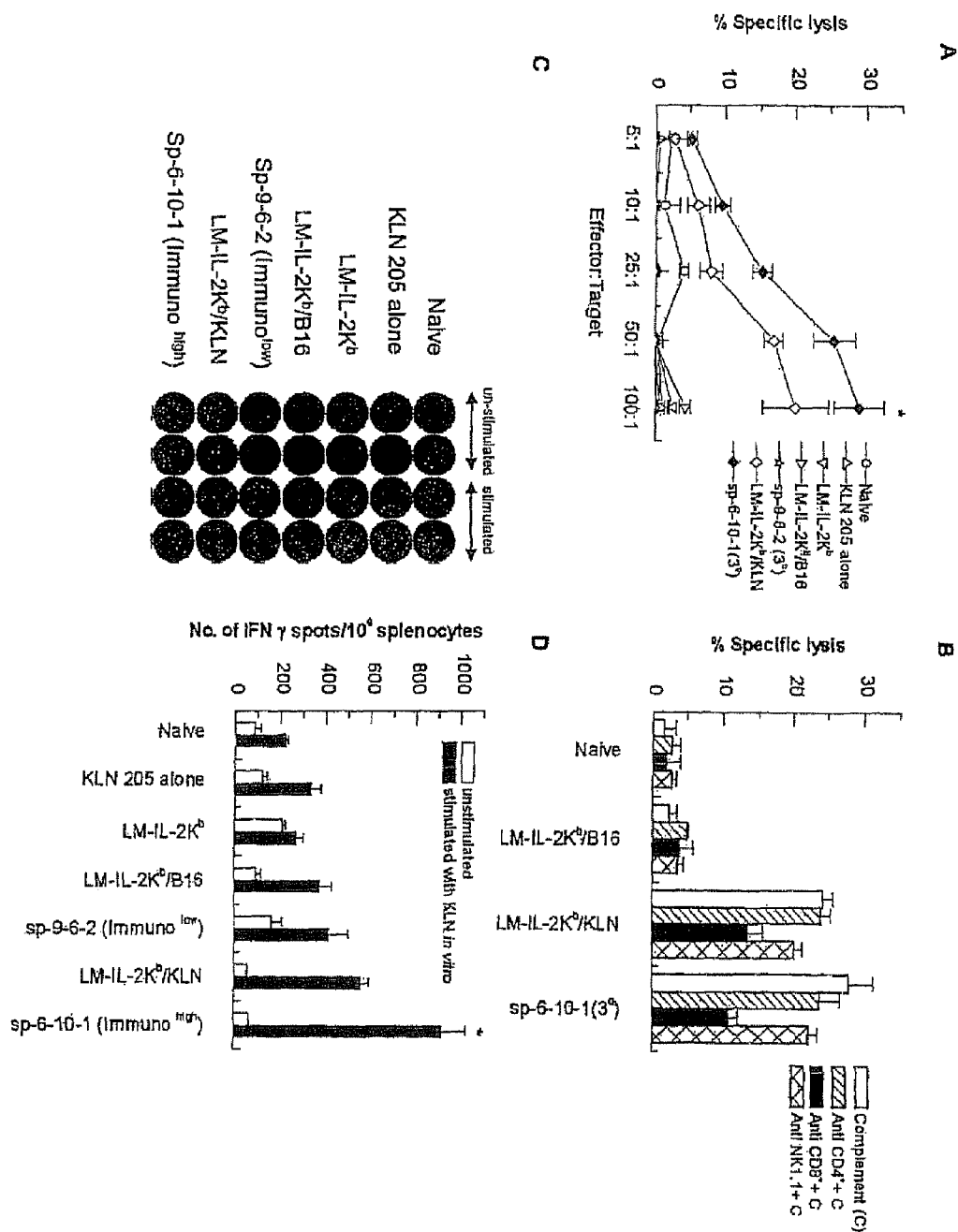
FIG. 15 shows that mAbs for CD8+ cells inhibit the cytotoxic activity toward KLN205 cells in tumor-bearing DBA/2 mice immunized with cells from the Immuno$^{high}$ (3°) pool (sp 6-10-1).

FIG. 15A shows results of the cytotoxicity tests, DBA/2 mice were injected s.c. with 1×10$^6$ KLN205 cells. Six days later, the mice received the first of two injections at weekly intervals of 4×10$^6$ cells from the Immuno$^{high}$ (3°) pool (6-10-1). One week later, spleen cells from the immunized tumor-bearing mice were co-incubated for 5 days with (mitomycin-C-treated) KLN205 cells. At the end of the incubation, $^{51}$Cr-labeled KLN205 cells were added at varying E:T ratios and the percent specific lysis were determined. As controls, the same procedure was followed except that the mice were immunized with (non transfected) LM-IL-2K$^b$ cells, with LM-IL-2K$^b$/B16 cells, with cells from the Immuno$^{low}$ pool sp-9-6-2 (3°), or with cells from the (non selected) Master Pool (LM-IL-2K$^b$/KLN). As addition controls, the mice were injected with KLN205 cells alone or the mice were not injected (naïve). p<0.001 for the specific release of isotope from KLN205 cells co-incubated with spleen cells from mice immunized with cells from the Immuno$^{high}$ (3°) pool (sp-6-10-1) and KLN205 cells co-incubated with spleen cells from mice immunized with cells from any of the other groups excepting mice immunized with cells from the Master pool (LM-IL-2K$^b$/KLN). p<0.05 for the specific release of isotope from KLN205 co-incubated with spleen cells from mice injected with cells from the Immuno$^{high}$ (3°) pool (sp-6-10-1) and mice immunized with cells from the Master pool.

FIG. 15B presents results of antibody inhibition procedure. The same procedure described in 6A was followed except that mAbs for CD4+, CD8+ or NK1.1 determinants, plus C, were added to the mixed cell cultures one hr before the cytotoxicity determinations were performed.

The same protocol described in 15A was followed in FIG. 15C, except that spleen cells from the immunized mice were co-incubated for 18 hr with KLN205 cells (E:T ratio=10:1) before they were analyzed in ELISPOT-IFN-γ assays. As controls, spleen cells from mice injected with (non-transfected) LM-IL-2K$^b$ cells, LM-IL-2K$^b$/B16 cells, or spleen cells from non-immunized mice were substituted for spleen cells from mice immunized with cells from the Immuno$^{high}$ (3°) pool. The ELISPOT plates from both stimulated (incubated with KLN205 cells) and unstimulated (incubated without KLN205 cells) cultures are presented.

FIG. 15D presents results of determination of the number of spots presented in 15C. p<0.005 for the difference in the number of spots in the group of mice immunized with cells from the Immune$^{high}$ (3°) pool sp 6-10-1 and mice immunized with cells from the Immuno$^{low}$ (3°) pool sp 9-6-2 or with cells from the (non selected) Master pool. p<0.001 for the difference in the number of spots in the group of mice immunized with cells from the Immuno$^{high}$ (3°) pool sp 6-10-1 and mice immunized with non transfected LM-IL-2K$^b$ cells, with LM-IL-2K$^b$/B16 cells, or mice injected with KLN205 cells alone.

The results (FIG. 15A) indicate that mice immunized with cells from the immuno$^{high}$ pools followed by the challenging injection of KLN205 cells survived significantly longer (p<0.001) than mice immunized with cells from any of the control groups. Eight of ten mice in the group immunized with cells from the immuno$^{high}$ pool) (3°) (sp6-10-1) survived more than 80 days, without evidence of disease. Lesser immunogenic properties were detected if the mice were immunized with cells after the first or second round of immunoselection. Six of 10 mice immunized with cells from immuno$^{high}$ pool after two rounds of immune selection followed by the injection of KLN205 cells survived more than 80 days, without evidence of disease. Fewer numbers of mice immunized with cells from the immuno$^{high}$ pool after the first round of selection or with cells from the non-selected Master pool survived more than 80 days. None of the mice immunized with cells from the immuno$^{low}$ pool or mice injected with PBS before the injection of KLN205 cells survived longer than 65 days. (p<0.001 for survival of mice immunized with immuno$^{high}$ pool (3°) versus mice immunized with cells from the immuno$^{low}$ pool or mice injected with PBS.)

Measurements of tumor growth in mice immunized with cells from the immuno$^{high}$ pool were consistent with survival. The greatest inhibition of tumor growth was in mice immunized with cells from the immuno$^{high}$ pool (sp 6-10-1) after three rounds of immune selection.

Thus, by successive rounds of immunoselection, the immunogenic properties of the transfected cell populations increased, as determined by both in vitro and in vivo measurements.

Example 28

Treatment of Mice with Established SCC by Immunization with Cells from the immuno$^{high}$ Pool of Transfected Cells The immunotherapeutic properties of transfected cells from the immune$^{high}$ pool were also investigated in tumor-bearing DBA/2 mice, highly susceptible to the growth of KLN205 cells.

Figure 14:
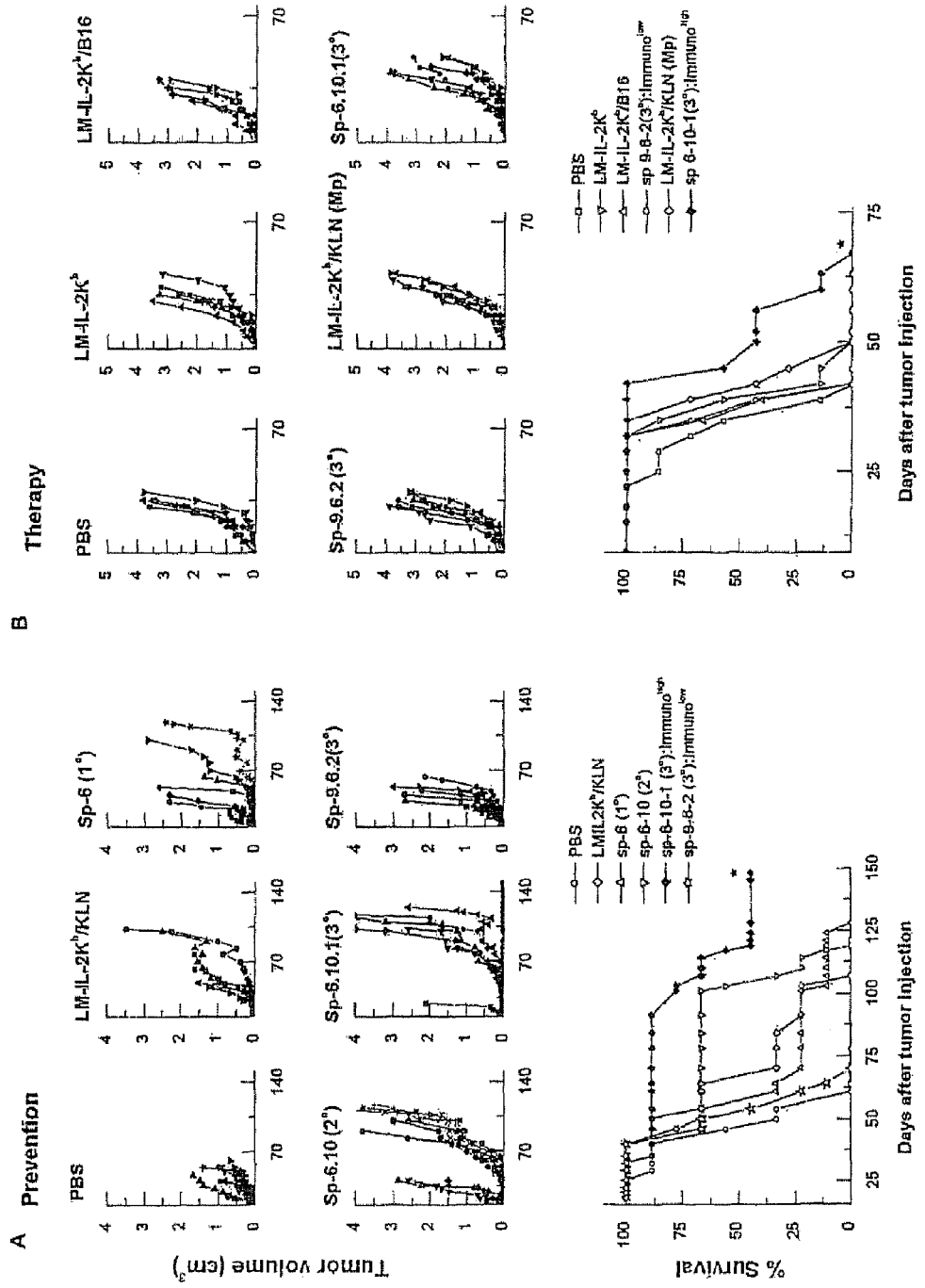
FIG. 14. Survival of tumor-bearing DBA/2 mice immunized with cells from the Immuno$^{high}$ (3°) pool of transfected cells.

As shown in FIG. 14A, DBA/2 mice were injected s.c. two times at weekly intervals with 4×10$^6$ cells from the Immuno$^{high}$ (3°) pool (sp-6-10-1 (3°)). One week after the last immunization, the mice were injected s.c with 1×10$^6$ KLN205 cells. As controls, cells from the Immuno$^{high}$ (1°) pool (sp-6), the Immuno$^{high}$ (2°) pool (sp-6-10), from the non-selected Master Pool (LM-IL-2K$^b$/KLN) or non-transfected (LM-IL-2K$^b$) cells were substituted for cells from the Immuno$^{high}$ (3°) pool. As an additional control, the mice were injected with PBS before they were injected with KLN205 cells. Tumor volumes were determined by the formula 0.5 length×width$^2$. (Length and width were determined with a dial caliper.) Mean survival time±standard error (SE): Mice immunized with KLN205 cells alone, 44±3.5 days; mice immunized with LM-IL-2K$^b$ cells (Master pool) 74±5.8 days; mice immunized with cells from the Immune$^{high}$ (1°) pool, 66±9.0 days; mice immunized with cells from the Immuno$^{high}$ (2°) pool, 88±10.5 days; mice immunized with cells from the Immuno$^{high}$ (3°) pool, 99±14.5 days; mice immunized with cells from the Immuno$^{low}$ (3°) pool, 52±2.7 days. p<0.001 for the difference in survival of mice immunized with cells from the Immuno$^{high}$ (3°) pool and any of the other groups except mice immunized with cells from the Immuno$^{high}$ (2°) pool where p for the difference in survival of mice immunized with cells from the two pools was p<0.01.

For therapeutic treatment, DBA/2 mice were first injected s.c. with 1×10$^6$ KLN205 cells (FIG. 14B). Six days later, the tumor-bearing mice received the first of two weekly s.c. injections 4×10$^6$ cells from the Immuno$^{high}$ (3°) pool (sp6-10-1). As controls, the same procedure was followed except that cells from the Immuno$^{low}$ (3°) pool (sp-9-6-2), LM-IL-2K$^b$/KLN cells from the Master Pool (LM-IL-2K$^b$/KLN, Mp), non-transfected LM-IL-2K$^b$ cells or LM-IL-2K$^b$ cells transfected with DNA from B16 melanoma cells (LM-IL-2K$^b$/B16) were substituted for cells from the Immune$^{high}$ sp-6-10-1 (3°) pool. Tumor volumes were determined by the equation 0.5l×w$^2$. Mean survival time±standard error (SE): Mice injected with KLN205 cells alone, 33±7.7 days; mice immunized with LM-IL-2K$^b$ cells, 34±8.7 days, mice immunized with LM-IL-2K$^b$/B16 cells, 35.2±5.3 days; mice immunized with cells from the Immuno$^{low}$ (sp-9-6-2)(3°) pool, 36.1±7.1 days; mice immunized with LM-IL-2K$^b$/KLN cells (Mp), 39±7.4 days; mice immunized with cells from the Immuno$^{high}$ (sp-6-10-1) (3°) pool, 50±6.9 days. p<0.01 for the difference in survival of mice immunized with cells from the Immuno$^{high}$ (3°) pool (sp 6-10-1) and any of the other groups.

Tumors were first established in immunocompetent naïve DBA/2 mice by an s.c. injector of KLN205 cells. One week later, when the tumor at the injection site reached a size of approximately 3-5 mm, the mice received the first of two s.c. injections at weekly intervals of 4×10$^6$ cells from the immuno$^{high}$ pool (3°) (sp 6-10-1). As controls, the same protocol was followed except that the mice were injected with cells from the immune$^{low}$ pool (sp 9-6-2), with cells from the (non selected). Master pool, with non-transfected modified fibroblasts (LM-IL-2K$^b$ cells), with PBS, or, as a specificity control, with LM-IL-2K$^b$ cells transfected with DNA-fragments from B16 melanoma cells (LM-IL-2K$^b$/B16).

As indicated, (FIG. 14B), tumor-bearing mice treated solely by immunization with cells from the immuno$^{high}$ pool (3°) survived significantly (p<0.01) longer than tumor-bearing mice treated by immunization with cells from any of the other pools. The survival of tumor-bearing mice immunized with cells from the immuno$^{low}$ pool or with cells transfected with DNA from the melanoma cells were not significantly different than those of tumor-bearing mice injected with PBS. Measurements of tumor growth in mice treated with the various cell constructs were consistent with the heightened immunotherapeutic properties of the immuno$^{high}$ pool (FIG. 14B).

Example 29

CD8+ T Cells Mediated Immunity Toward KLN25 Cells in Tumor-Bearing DBA/2 Mice Immunized with Transfected Cells from the immuno$^{high}$ Pool (sp 6-10-1 (3°)

MAbs were used to determine the classes of cells mediating resistance to SCC in tumor-bearing DBA/2 mice immunized with the transfected cells. As a first step, mice with established (3-5 mm) neoplasms received the first of two weekly s.c. injections of 4×10$^6$ transfected cells from the immuno$^{high}$ pool (3°) (sp 6-10-1). One week later, spleen cells from the immunized tumor-bearing mice were analyzed for the presence of cytotoxic cells, at varying effector: target (E:T) ratios. As controls, the tumor-bearing mice were injected with cells from the non selected Master Pool, with cells from the immuno$^{low}$ pool (sp-9-6-2 (3° or with non transfected LM-IL-2K$^b$ cells. As indicated (FIG. 15A), the cytotoxic reactions of greatest magnitude were in mice immunized with cells from the immuno$^{high}$ pool (3°). Lesser responses were present in mice immunized with the non-selected Master Pool (p<0.001). The responses in mice immunized with cells from the immuno$^{low}$ pool or with non-transfected cells were not significantly different than those of tumor-bearing mice injected with PBS. Analogous results were obtained if the analyses were performed by ELISPOT-IFN-γ assays (FIG. 15C).

The effect of monoclonal antibodies for CD8+, CD4+ and NK1.1 cells on the cytotoxicity reactions were next used to determine the cell types activated for immunity to KLN205 cells in tumor-bearing mice immunized with cells from the immuno$^{high}$ pool (3°). The results (FIG. 15B) indicated that the addition of CD8+ antibodies and Complement (C) to the spleen cell suspensions inhibited the cytotoxic reaction toward KLN205 cells to the greatest extent. Lesser effects were observed if CD4+ or NK1.1 mAbs were added. As a specificity control, tumor-bearing DBA/2 mice were immunized with LM-IL-2K$^b$ cells transfected with DNA from B16 melanoma cells (LM-IL-2K$^b$/B16). An analysis of the spleen cell-mediated immunity toward KLN205 cells in these mice failed to indicate the presence of immunity toward KLN205 cells.

Various clinical trials are in progress, designed to test immune-based therapies (Morse M A, Cancer Res 2005; 65:553-61; Hirschowitz E A, J Clin Oncol. 2004; 22:2808-15; Raez L E, J Clin Oncol 2004; 22:2800-7; Chang G C, Cancer 2005; 103:763-71). In lung cancer, determinants such as survivin (Xiang R, Cancer Res 2005; 65:553-61), p185 (HER-2/neu) (Akita K M, Jpn J. Cancer Res 2002; 93:1007-12), epidermal growth factor (Gonzalez G, Ann Oncol 2003; 14:461-6), p53 (Wang T, Lung Cancer 2001; 34:363-74) among others (Chang G C, Cancer 2005; 103:763-71; Hirschowitz E A, J Clin Oncol 2004; 22:2808-15) were identified as potential targets of immune-mediated attack. It is likely that these are only a few of a potentially large number of TAA. Cancer cells are notoriously genetically unstable (Peltomaki P, Cancer Res 199.3; 53: 5853-5; Gonzalez-Zulueta M, Cancer Res 1993; 53: 5620-3; Risinger J I, Cancer Res 1993; 53: 5100-3; Han H-J, Cancer Res 1993; 53: 5087-9; Bavoux C, Cancer Res 2005; 65:325-30; Takahashi Y, Mol Carcinog 2005; 42:150-8).

An additional important advantage was that the vaccine could be prepared from microgram amounts of amounts of tumor tissue. Forty μg of DNA, derived from approximately 10$^7$ cells, (4 mm tumor) was sufficient. As the transferred DNA spontaneously integrates into the genome of the recipient cells, and is replicated as the cells divide, the number of vaccine cells could be readily expanded for multiple rounds of therapy. The ability to prepare an effective vaccine from such small neoplasms provides an opportunity to prepare vaccines from patients with minimal disease after conventional therapy.

However, only an undefined, small proportion of the transfected cells was expected to have incorporated DNA-fragments specifying TAA. Several lines of evidence indicated that the strategy designed to enrich the transfected cell population for highly immunogenic cells resulted in an increase in the vaccine's immunotherapeutic properties. Both cytotoxicity and ELISPOT-IFN-γ assays revealed a progressive increase in the immunogenic properties of the selected cell pools. By the third round of immune-selection, the percent specific lysis of KLN205 cells from mice immunized with cells from the immuno$^{high}$ pool was more than three fold greater than that of mice immunized with cells from the non-selected (Master) pool.

Analogous results were obtained if the anti tumor immune responses were tested by ELISPOT-IFN-γ assays. Furthermore, tumor-bearing mice treated solely by immunization with cells from the immune$^{high}$ pool (3°) survived significantly longer than mice in various control groups, including mice treated by immunization with fibroblasts transfected with DNA from B16F1 cells, a melanoma cell line. It is conceivable that the immunogenic properties of the vaccine could be further enhanced by additional rounds of immune selection. As the transfected cells failed to express syngeneic MHC class I-determinants, cross priming may have been responsible for the induction of immunity to the SCC (Donnelly J J, J Immunol 2005; 175:633-9; Bohnenkamp H R, Cell Immunol 2004; 231:112-25).

The cells in the highly immunogenic pool expressed an array of undefined antigens associated with the squamous carcinoma cells. TAA expressed by the transfected cells were not identified. The identification of TAA expressed by the patient's neoplasm may not be required to generate a vaccine that can be used effectively in patient therapy. Nevertheless, strategies disclosed herein permit the identification of such antigens.

The strategy reported here raises the possibility that an analogous approach can be used to generate a vaccine of enhanced effectiveness that can become part of the overall management of patients with non small cell lung cancer and other histologic types of cancer as well.

The invention claimed is:

1. A method of identifying one or more tumor associated antigens of a target tumor comprising the steps of:
   (a) transfecting genomic or cDNA from cells of a target tumor into recipient cells expressing at least one MHC determinant that is allogeneic to a plurality of recipient animals;
   (b) diluting a suspension of the transfected recipient cells into a plurality of cell pools;
   (c) expanding the cells of the plurality of cell pools of step (b);
   (d) immunizing each of the recipient animals with a portion of each of the expanded cell pools of step (c);
   (e) isolating spleen cells from the recipient animals immunized according to step (d);
   (f) incubating the isolated spleen cells with the target tumor cells;
   (g) detecting an immune response of the spleen cells to the target tumor cells and identifying the cell pool that generates the highest level of immune response (the immuno$^{high}$ pool) and the cell pool that generates the lowest level of immune response (the immuno$^{low}$ pool);
   (h) optionally enriching the immuno$^{high}$ pool by repeating step (b) to step (g) with the immuno$^{high}$ pool;
   (i) isolating RNA from the cells of the immuno$^{high}$ pool and from control cells;
   (j) performing microarray analysis on RNA isolated from the cells of the immuno$^{high}$ pool and RNA isolated from the control cells; and
   (k) identifying one or more genes expressed at increased levels in the cells from the immuno$^{high}$ pool as compared to the control cells,
   wherein the one or more genes identified are tumor associated antigens of the target tumor.

2. The method of claim 1, wherein the control cells are cells of the immuno$^{low}$ pool.

3. The method of claim 1, wherein the recipient cells further express a cytokine.

4. The method of claim 3, wherein the cytokine is IL-2.

5. The method of claim 1, wherein the recipient cells are fibroblasts.

6. The method of claim 1, wherein the target tumor is a solid tumor or a hematological tumor.

7. The method of claim 6, wherein the target tumor is melanoma, lymphoma, plasmacytoma, sarcoma, glioma, thymoma, leukemia, breast cancer, squamous carcinoma, prostate cancer, colon cancer, esophageal cancer, brain cancer, lung cancer, ovarian cancer, cervical cancer, or hepatoma.

8. The method of claim 7, wherein the target tumor is breast cancer, lung cancer or squamous carcinoma.

9. The method of claim 1, wherein the immune response is detected in step (g) by Elispot IFN-gamma assay or $^{51}$Cr-release assay.

10. The method of claim 1, wherein the suspension of transfected recipient cells are diluted in step (b) to a cell density from about $1 \times 10^3$ to about $1 \times 10^5$ cells in each cell pool.

11. The method of claim 10, wherein the suspension of transfected recipient cells are diluted in step (b) to a cell density of about $1 \times 10^3$ cells in each cell pool.

* * * * *